(12) United States Patent
da Costa e Silva et al.

(10) Patent No.: US 7,439,417 B2
(45) Date of Patent: Oct. 21, 2008

(54) TRANSCRIPTION FACTOR STRESS-RELATED PROTEINS AND METHODS OF USE IN PLANTS

(75) Inventors: Oswaldo da Costa e Silva, Neustadt (DE); Nocha Van Thielen, Durham, NC (US); Ruoying Chen, Apex, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/805,623

(22) Filed: May 24, 2007

(65) Prior Publication Data

US 2008/0052792 A1    Feb. 28, 2008

Related U.S. Application Data

(60) Continuation of application No. 11/564,883, filed on Nov. 30, 2006, which is a division of application No. 10/168,846, filed as application No. PCT/US00/34972 on Dec. 22, 2000, now Pat. No. 7,164,057.

(60) Provisional application No. 60/171,745, filed on Dec. 22, 1999.

(51) Int. Cl.
    C12N 15/82    (2006.01)
    C12N 15/29    (2006.01)
    A01H 5/00     (2006.01)
    A01H 5/10     (2006.01)

(52) U.S. Cl. .................. 800/289; 435/419; 435/468; 800/298; 536/23.6

(58) Field of Classification Search .................. None
See application file for complete search history.

(56) References Cited

U.S. PATENT DOCUMENTS 6,077,994 A * 6/2000 Coupland et al. ........... 800/290

* cited by examiner

*Primary Examiner*—Cynthia Collins
(74) *Attorney, Agent, or Firm*—Patricia A. McDaniels

(57) ABSTRACT

A transgenic plant transformed by a transcription factor stress-related protein (TFSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated TFSRP, and isolated nucleic acid coding TFSRP, and vectors and host cells containing the latter. Further provided are methods of producing transgenic plants expressing TFSRP, methods of increasing expression of other genes of interest using the TFSRP, methods of identifying novel TFSRP, and methods of modifying the expression of TFSRP in plants.

17 Claims, 29 Drawing Sheets

FIGURE 1A

Nucleotide sequence of the partial CABF-1 from *Physcomitrella patens* (SEQ ID NO:1)

GCACCAGCGAATCCGTCTCCGCCTCCGCCTTCTGCACGCGTGGTTGTGGTCGACCTC
TCGCCGGAGCAACAGGAAACTAATCCCTTTTCCAGCACTAAACGATTGAAGCAATTT
TTTTTTTCTTGTGAACTGCTCACTCTCTCTGTTATGAGGGGATTCGAAGCTTGAAA
GTTATGAGCTGAAGGTTGAGGACACGTAAGCACCAGAGGACGATCATACTACAATT
AACCCTTGCGGGGAAAAGCCCAGGCAAAATAGGACGGATGGCCGACAGTTACGGCC
ACAACGCAGGTTCACCCGAGAGCAGCCCGCATTCTGATAACGAGTCCGGCGGCCAT
TACCGTGATCAGGACGCTTCTGTACGGGAGCAAGACCGGTTTTGCCCATCGCAAAT
GTGAGCCGAATCATGAAGAAAGCATTGCCATCTAATGCGAAGATATCGAAAGACGC
CAAAGAGACTGTGCAGGAGTGCGTATCCGAGTTCATCAGTTTCATTACTGGTGAGGC
GTCCGACAAGTGTCAGAGGGAAAAGAGGAAGACGATCAACGGGGATGACTTGCTGT
GGGCCATGAGTACTCTTGGTTTTGAAGATTATGTGGAACCTCTGAAGGTGTACCTAC
ACAAGTATCGTGAACTGGAGGGGGAGAAGGCCTCTATGGCCAAGGGTGGTGATCAA
GCAGGG

FIGURE 1B

Nucleotide sequence of the partial DBF-1 from *Physcomitrella patens* (SEQ ID NO:2)

GGCACGAGGCTTGATGATGATCATGCACTAGCTTCTGCAAAGTGCCAGGCTTTAGCA
CGTCTACTTCCCAAGTTACAGCAAGGTGGCCATCGCACATTGATATTCAGCCAGTGG
ACAAGCATGCTGGATATTTTAGAATGGGCTCTTGACGTCATGGGTTTTTCTTACACTC
GCCTAGATGGAAGCACTCAAGTAAGTGAACGCCAAACCCTAGTGGACGAGTTCAAC
AATGACCCTAGCATATTTGTGTTTCTCCTGTCTACTCGAGCTGGAGGTCAAGGTCTA
AATTTAACAGGAGCAGACACAGTCATTTTACATGATTTGGACTTCAATCCCCAAATG
GATCGACAGGCTGAGGATCGCTGTCATCGGATTGGCCAGTCTAAACCTGTTACGATA

FIGURE 1B (con't)

TACCGACTTGTAACAAAAGATACGGTCGATGAAAGTATATACAAGATAGCCCAACA

GAAGCTGGTCCTCGATGCGGCAGTTCTTGAANGAAAAGAGTCATCCTCTGATCTTAA

TGATG

FIGURE 1C

Nucleotide sequence of the partial CBF-1 from *Physcomitrella patens* (SEQ ID NO:3)

GGCACGAGCTGATACTAATTGCACGAGGTTTTCTCAAATGTGTTTTTGGGTACAGGA

AGGTGGAGGGGAATTTGTAAGTGACAGAGACGTGGTGGGAGTGGGAGGAGTGTGA

GGAATCGAGCTAGCACCTAAAGGATTTCGGGGTGAAGGAAGGTGCGATTGAAGGCG

TGCATGAAATTTTGACGCAGCGGGTTGAATCGGAAGGAGTTTTCAGCAGCTGGAAA

GTACCTTCGAGGGTTGATTCATCCAAAGTTTCCATGTGATATGGCTTCAAAGTATCC

GCGAAAATGTAGAGAGCACGCATCACCTGGAGTTGGTGGCAGGGAATCTACGCATC

GCTTTGATTCAAGGTCGCAGTCGTATTCGTTCTCGGAGAAACCTTACCACCGTCGTC

GCCGGGATGCGTTTCGTGATATGATCAGCGATTTGGTGCATCAGCCTTCCGACACTG

CCGTGCCTGGTTTCAGGGGAGTGCGCTATCGTCAGAAACTGAACAAGTACGTGACA

GAGATTCGGCCCACGAGGTGCTCGAAGAAAATTTGGCTTGGGACGTATGACACTGC

AGAGGAAGCAGCGCGTGCCTTTGACATCGGAAATTTGTGTTGTAAGAAAAACCTGC

CGCTCAACTTTCCGGATTCGACTCAGATGTTGCAGAGAATCTCGTCGAAATTGACCC

CCGAAGCGCAACGAAAAGCCATCGCGACGCTGGCGAAGGACGTAGTGCGAATGGA

AAATGACAGGTCGAAGTTGGGTGGCGGTAACCTGACTACCACAGAGCCCCCGGTCC

ATTCCGAGCCTATTACTCAACACCTTGCAGCAGCTGAGATTCGCGCGGTCACGTACA

TTGAACAGCCCCTGGAAATTGTCTACGGAGTGGAAGAATCGGCGACGGCCATGTCG

GTAACGGAAGCAAATGCGCGCGATAACCACTCTTGGAGTTGGGACTTGGGCAAAGT

GATCCTTGATGACGAGCTCTCTGAAATTCCTAACTTCGTCGGAG

FIGURE 1D

Nucleotide sequence of the partial HDZ-1 from *Physcomitrella patens* (SEQ ID NO:4)

GGCACGAGGGCAAGAGGGGATAGAGACTTGAAAGGAAAGGGAGGGAAGGGTGTAA
GGAGGCCCACGGGCAGGGTCAAGGTGTCCAATGCACCTGCAAGATCAGGAAGCTTG
AAGTAGATCAGGGAAAAAACGATGGTAGTCCCTAGTTTACCCGCCTTCGGAGGACA
GAACGCCATGCTCAGACGCAACATTGACAACAACACCGACACTCTGATTTCTCTGCT
TCAAGGGTCCTGCTCCCCTCGCGTGAGCATGCAACAAGGATATGTTGCAGTGCCGCG
TTCATCGGAGAGTCTCGAAAACATGATGGGGGCTTGTGGGCAAAAACTGCCTTACTT
TTCGTCATTTGATGGGCCGAGTGTAGAAGAGCAAGAGGATGTCGACGAAGGTATCG
ACGAATTCGCACACCACGTGGAGAAAAGGAGGAGATTGTCATTAGAACAAGTGCG
ATCATTAGAACGGAATTTTGAAGTGGAAAACAAGCTTGAGCCCGAGAGGAAAATGC
AACTAGCTAAGGAGCTTGGACTGCAACCTCGTCAAGTGGCGGTGTGGTTCCAGAAT
AGACGGGCAAGGTGGAAAACCAAACAGCTCGAGCGCGACTACGAGACCCTGAAGA
AAGCCTACGACAGGCTTAAAGCAGACTTCGAAGCCGTTACTCTAGACACAAGTGCT
CTTAAAGCTGAGGTGAGTCGCCTCAAGGGAATCTCTAATGCACGACGTCAAGCCCG
CCGAATTCGTTCAGGGCAAGTGTGACACAACGAGTCACCCTGCCTCCCCTGCGCAAT
CGGAGAGGTCCGACATTGTGTCATCGAGGAATCGCACAACTCCTACCATACATGTGG
ATCCCGTGGCACCCGAGGAAGCCGGCGCTCACTTAACCATGAGCTCGGATAGCAAT
TCCAGCGAGGTCATGGACGCTGATAGCCCTCGCACGAGCCACACCAGCGCTAGTAG
GAGCACTTTGTCCACAAGTGTGGTGCAGCCTGACGAGGGCCTGGGAGTGGCCCAGT
ACCCCCACTTTTCTCCCGAAAACTTCGTGGGTCCCAATATGCCAGAGATTTGCGCTG
ATCAGTCACTTGCATCTCAAGTGAAGCTGGAAGAGATCCACAGCTTCAATCCCGACC
AAACCTTCCTGCTCTTGCCCAACTGGTGGGATTGGGCTTGATTCGTTTCTTCATCTGT
ACCCATACACTTTTTCCTTGAATCCAAGTTGAATTCACTTTAGGCAGTGTTTTTCAC

FIGURE 1D (con't)

GATGTACCACTTGTTATTCTTCCACCATGTGCAATCCAACGTCAANCAAAGTTGCAC

ATCGGCGATCATTGGTGACGATGTCGAGCATCGATCGTCACATGC

FIGURE 1E

Nucleotide sequence of the partial ZF-1 from *Physcomitrella patens* (SEQ ID NO:5)

GCACGAGCTCGGTTGTGGAAGCTGTCTCGTGGCTTCTTCCGCACCCTAAGATCTCGA

CCAACTCTATTATCAGAGGCAGCGCTGCAGCCGACGAGATGGGTTCGTCGCCTTTCC

ACGACCGGCCCTTTAGTCCCAAGCCCAAGAAACAGAAGGTTGAATTGCCCGCGGAC

ATATTCTCTGATGTGGACCCTTTCCTAGACTTGGACGATGCAACCGTTACCGGAATT

CAACCCGACAGCTTGGTACCAGTCCATATGCCAGAATGCTCCGAGGACACGGATTC

GCTTGCTCACTCCATGGACCCTTCGTTTACTAAATTTCCTCTCTCGGCGAAGAGCGGT

TACAGCTATGGCACATCTACCCTTACTCAGAGCATTTCTTGTTCGTCTCTAGATGCCG

CCGTTGTTCCAGACTCCAGTCTCAGCGACATTTCCACACCCTACCTAGACTCACAAA

GCTCCCAAGATATGTCAGCTCGCCTGCCACACCAGACTGGAGGTCCCATTGACACCG

TCGACCGTGAAGCTCGCGTGTTGCGCTACAAGGAGAAGAGGCAGAAGCGCAAGTTT

GAGAAAACAATTCGCTATGCATCAAGGAAGGCATATGCTGAGAGCCGGCCGAGGAT

CAAAGGAAGGTTCGCTAAGAGAACTGATTCCGACATGGAGCAGTTTGGCTCAGTGG

ACTCAAGTTTCGGAGTGGTTCCAAGTTTTTGAGTTTTCTTGTGTATTGGAGTCTCCAT

CGAGCAAGGTCATCTGAAATGGAAAGCTGCTGTGTAACATAGAGGAGCTGCTGTAA

GAACTGTGTAGAGCCATCCAAGTGGTGAAGCACCTGAAAAAGTGGCAGCAATGTAA

ATTGTTCAGACTCTCAATGGTCACCAGTACCAAGTCATGCCATTCTATAATCCCTTTC

AGAACACGATTAAATGCCTTGTGGACAGTACAGGATGTAGTCAGAGTTCTAGTAGT

GGTTTTTTTCTATTTTTCTTTTTGTTGATTGAGAGCTTTCGGAACGGTGAGAACTTCGT

GGCGCGAATCCTCTGTCCTGCGATCGTTATGATGCAGCGAATTCTTCCGATCTTGAT

FIGURE 1E (con't)

GTATTTCAACACTTCCATAATGCTCTTGGATTTTTGGGTCATTTCCTCAGAAGGTGTT

GAGCTAACAAAAAAAAAA

FIGURE 1F

Nucleotide sequence of the nucleotide partial LZ-1 from *Physcomitrella patens* (SEQ ID NO:6)

CTTCAAAGAACTCGGCAACAGCAGGGTCTATACCTTGGACCTGGTTCGTACAGTGAC

CAAAATGGTCAGTCGGGTGGAGTTGGTGGAGCAAACGCATATAGTTCAGGAGCTGC

TGCATTTGACCTGGAGTATGCAAGGTGGGTTGAAGATCATACCCGGCAGATGAGTG

AGCTCCGGGTGGCCCTACAGGCTCATGTCGCTGACGCTGATTTACGATTACTAGTGG

ATGGGAGTATGGCCCACTATGACGACCTCTTTCGGCTCAAGGACGCTGCTGCAAAAG

CCGACGTGTTTCATCTCGTGTCCGGCATGTGGAAAACTCCTGCAGAGCGATGCTTTG

TATGGATTGGAGGCTGCCGACCCTCTGAGTTACT

FIGURE 1G

Nucleotide sequence of the partial CABF-2 from *Physcomitrella patens* (SEQ ID NO:7)

CATCCTGGCGCCGTCATGCCTTTACAGATGCACTACCCGCAAGCCCAGCAACAGATG

ATGCCGCAGCTTGGTGATCAGCAGATGCAGCCGCAGCTTCATTATCAGCAAATTCAG

AAACAGCAGCTGTCCCAGTTCTGGCAGCAGCAAATGCAGGAAATGGAGCAAGTCAA

TGATTTTAAGACCCATCAGCTACCACTGGCACGCATCAAAAAAATCATGAAGTCGG

ATGAAGATGTTAAGATGATCGCAGCCGAAGCTCCAGTGCTGTTTTCAAAAGCTTGTG

AGATGTTTATTTTAGAATTGACACTGCGCTCTTGGATTCATACGGAGGAAAATAAGC

GAAGGACACTACAAAGAAATGATATTGCAGGGGCTATCACTAGGGGAGACATCTTC

GACTTTCTTGTTGACATCGTTCCACGTGACGAGTTGAAGGAAGAAGATTTGGGTGTG

CCATGGAC

FIGURE 2A

Nucleotide sequence of the full-length CABF-1 from *Physcomitrella patens* (SEQ ID NO:8)

GGCACCAGCGAATCCGTCTCCGCCTCCGCCTTCTGCACGCGTGGTTGTGGTCGACCT
CTCGCCGGAGCAACAGGAAACTAATCCCTTTTCCAGCACTAAACGATTGAAGCAATT
TTTTTTTTCTTGTGAACTGCTCACTCTCTCTGTTATGAGGGGATTCGAAGCTTGAA
AGTTATGAGCTGAAGGTTGAGGACACGTAAGAGCGAAGGACGATCATACTACAATT
AACCCTTGCGGGGAAAAGCCCAGGCAAAATAGGACGGATGGCCGACAGTTACGGCC
ACAACGCAGGTTCACCCGAGAGCAGCCCGCATTCTGATAACGAGTCCGGCGGCCAT
TACCGTGATCAGGACGCTTCTGTACGGGAGCAAGACCGGTTTTGCCCATCGCAAAT
GTGAGCCGAATCATGAAGAAAGCATTGCCATCTAATGCGAAGATATCGAAAGACGC
CAAAGAGACTGTGCAGGAGTGCGTATCCGAGTTCATCAGTTTCATTACTGGTGAGGC
GTCCGACAAGTGTCAGAGGGAAAAGAGGAAGACGATCAACGGGGATGACTTGCTGT
GGGCCATGAGTACTCTTGGTTTTGAAGATTATGTGGAACCTCTGAAGGTGTACCTAC
ACAAGTATCGTGAACTGGAGGGGGAGAAGGCCTCTATGGCCAAGGGTGGTGATCAG
CAGGGAGGAAAAGAGAGCAACCAAGGAGGTATGGGGTCGATGGGCATGGCAGGCG
GAATCAACGGCATGAACGGAACGATGAACGGGAACATGCATGGGCATGGAATTCCC
GTATCGATGCAGATGATGCAACAGCCGTACGCGCAGCAGGCACCTCCGGGGATGAT
ATATTCTCCTCATCAAATGATGCCGCAATACCAGATGCCGATGCAGTCTGGTGGAAA
CCAACCCCGCGGAGTGTAAGAGTTTTCACTGGCAGGAGGCTTTGGAAGTGGGGATA
TTGTCGACAGCGTGATGGGGTGTTTGGAGCATGGGCAGGGCATTATGGTGCTGTTG
AAACAGTGATGGGTGGGTCATGTGAAGTGTTGGCGACTGTTGAATGATGAAAACAT
AGAAGTGATGTCGTTGAAGCTCGGGGAGTTTCAAGTGAAAGGAGGAGCACTTTTTG
TTTGGAAAGGAGCGTACCGGGTCTGGCAGTGTACATTCTGAATGATAGTTATCTGTG
CTGATTTTTCTTGGCCTTGGCAATACGAGGGGGTTGAATATTTTGCTTTGAATTCGTT
GACATTTCAACCTTTTCTATGTGAAAAGGCTCTGTAGGATGCAAGATAAGGAAAGAC
ATGCAGATTGATAAAAAAAAAAAAAAAAAAAAAAAAAAAAAAAAAAA

FIGURE 2B

Nucleotide sequence of the full-length DBF-1 from *Physcomitrella patens* (SEQ ID NO:9)

GCCCTTATCCCGGGCGATGGTGCGTTCGAGATCGTAAGGTTGCCGACGAAGGCGTA
ACTTGGAAGTCCTCTGTGTCCCGGCGATGTCCCAATGTTGGCCCGATTTTCTGTTTT

FIGURE 2B (con't)

```
AGCGAGCTGTGGGCTAGTTTGTGGGTATGATCCGGGGAATGAGACGAGATGTCTGT
CTGAGTGAGACCACTCTAGGGGCTGTTGGAGGATGAGGAGGGAAGCGCAGAAGTTG
GCCATTCTTTTCAGTGACTGGACTCTGTGCGAGTGGTCAGCTTTCGGGAGCTGCTGTT
GCATTGACCGGTGATTCTTTCGAGATCGTAGAGACAGCAGCTGGCAAGGGTTTTGGG
AGGCTTTTCAAATGAAGGGCATTCAAGAGCTTTCAGATGATGAAGATTATATTCCGC
CTGTCAATGCATCGCGATATTTCAACAGGGGCAAAGCGCTCTCAAAGACATCATCCA
ATCATGCCAATGGAAATGGAAATCCAAACGGAACGAGTTTTGGAGTTTCAACTTCTT
CAGCAAGTGACTCTGACAAAGATAAGAAATCCGAAGTTTCAGGTTCTTTACTAAGCG
ATTCTGGCAAGAATCAAAAGTCCGTTACTGAATTGGATTCGTTCGCATTTAACCGCA
AGTCCAGAATTGCCAAGCGACCTATCGAGCTACTCGAAGACGAGGAGGACGTGGAC
GTTGGAGCTGCAAAGGTTGTAGACATTGAGCCGACTAACGGAAACAAGAGGCGGAG
ACGGTATCACACCATCGAAGACAGTGACGATGAAGAGTTGGATGAGAAGAAATCGT
TTGGTGATAATCTGACCCCAGGAACGGAAATCGATCAATGTGCAGCCGATGAATCCT
TAGCAAAAGGTTGCAGGATTTAGAGCACCGGGCAGTTTCTGGCCGTAATCGCCTG
GTTCAAATTTTGTCAGATTCCGATGAAGAAGAAGAGGAAGAAGTAAATCCCATAAC
CATCACCCTACAAAGGTGTGACCAGATTGCAGCATCATTGCGAGAAGAGCTGCAGG
CCAGCAGTTCAAGTGATAACTCGGTTAATGAAGATCGTTATGCAGAGGTTGATGTAG
CAGCAGCAAAAATTGTGAGCCAGGCAGATGTCTGTGCAGCTTGTGGCATTGCCGAG
AATGATACACAACGAATGCTCAAGCCATATCAGCTTGTAGGCGTCAATTTCATGCTG
CTACTTCACCGCAAACATGTTGGGGGTGCAGTTGCGTATCTTGCCCTTCTGAAACAT
CTTGATGGAGATGCTGGTCCTCATCTTTTAGTTGCACCTGCTTCTCTTTTAGAAAACT
GGCAAAGAGAACTCAAGAAGTGGTGTCCTGCATTTAAGGTGGAGCTCTATCATGGC
TCAGGAAGGGCAGCTTTAAACAGGAGGCTTCAGTATGCTGCAAAATCTAAAGGGCC
TGCACCCTTTAACGTGATGCTGACGTGCTACTCCCTTTTGAGAGGCAGAGTGCTCA
GACAAAAGATGACCGCAAATTCCTTAAGAAATGGAATTGGCGCTGTGTGGTTATGG
```

FIGURE 2B (con't, page 2)

ACGAGGCTCATCTTTTGAAGGACAGAAGCAGCTTTCGCAGCAAAAAGTTGCGAGAT
ATAGCTCACAAAGCAATTCAAAGACTGATGCTGACTGGTACTCCACTCCAGAACGAT
TTGCAGGAGCTATGGTCACTTCTGGAGTTCATGATGCCTGATGTGTTCAACACAAAT
GGCGTTGATTTAGATCAATATCTGGGAACCAGGAACGATACCTCAGGGATTGTTGTG
CAGGATACGAACTTGATGACTCGGATCAAAGGAATACTAGGACCTTTTGTATTACGG
AGAATGAAAACTGATGTTATGCGCCAGCTTGTATCAAAGATTCAGGAGGTGGAGTG
TGTGGAGATGCTAGACGAGCAATCAATGGCATATAAAAAGCTGTAATGAGTATA
GAGCCCTTGCTGAGTCCGCACGTGCCGCTAAAGCTGCAAAGAAATCCTCAGTTAGC
GTAGTAGATGTCCTTCCTCGTCGACAAGTGACCAATATCTTTACTCAATTGAGAAAG
GTCAAGAAATTGGCTAAGAAATTTCATCCATTAGGAGTTTTTGGATATGAATGCGAT
TTGCAGCGTGTGGAGGAAGAATTGACTAGTTACAGCGATTTTGACCTCCACAAGTTG
TGTATTCAATATGGAGGCGCTGCGGGAGGGCAAGGAAAGCTTGATGATGATCATGC
ACTAGCTTCTGCAAAGTGCCAGGCTTTAGCACGTCTACTTCCCAAGTTACAGCAAGG
TGGCCATCGCACATTGATATTCAGCCAGTGGACAAGCATGCTGGATATTTAGAATG
GGCTCTTGACGTCATGGGTTTTCTTACACTCGCCTAGATGGAAGCACTCAAGTAAG
TGAACGCCAAACCCTAGTGGACGAGTTCAACAATGACCCTAGCATATTTGTGTTTCT
CCTGTCTACTCGAGCTGGAGGTCAAGGTCTAAATTTAACAGGAGCAGACACAGTCAT
TTTACATGATTTGGACTTCAATCCCCAAATGGATCGACAGGCTGAGGATCGCTGTCA
TCGGATTGGCCAGTCTAAACCTGTTACGATATACCGACTTGTAACAAAAGATACGGT
CGATGAAAGTATATACAAGATAGCCCAACAGAAGCTGGTCCTCGATGCGGCAGTTC
TTGAAGGAAAGAGTCATCCTCTGATCTTAATGATGGTGATGCTCGCACGATGGGTG
AAATTCTTTCTGCATTATTGGATGTTCCACCGACATGATCCTGGAGTCCAGAACACA
TTTTTAATTTATTTTCATTATCTTTATCTGGCACTGCGAGAAAGCTCGTTAACGCAAG
GGC

FIGURE 2C

Nucleotide sequence of the full-length DBF-1 variant from *Physcomitrella patens* (SEQ ID NO:22)

GCCCTTATCCCGGGCGATGGTGCGTTCGAGATCGTAAGGTTGCCGACGAAGGCGTA

ACTTGGAAGTCCTCTGTGTCCCGGCGATGTCCCAATGTTGGCCCGATTTTCTGTTTTT

AGCGAGCTGTGGGCTAGTTTGTGGGTATGATCCGGGGAATGAGACGAGATGTCTGT

CTGAGTGAGACCACTCTAGGGGCTGTTGGAGGATGAGGAGGGAAGCGCAGAAGTTG

GCCATTCTTTTCAGTGACTGGACTCTGTGCGAGTGGTCAGCTTTCGGGAGCTGCTGTT

GCATTGACCGGTGATTCTTTCGAGATCGTAGAGACAGCAGCTGGCAAGGGTTTTGGG

AGGCTTTTCAAATGAAGGGCATTCAAGAGCTTTCAGATGATGAAGATTATATTCCGC

CTGTCAATGCATCGCGATATTTCAACAGGGGCAAAGCGCTCTCAAAGACATCATCCA

ATCATGCCAATGGAAATGGAAATCCAAACGGAACGAGTTTTGGAGTTTCAACTTCTT

CAGCAAGTGACTCTGACAAAGATAAGAAATCCGAAGTTTCAGGTTCTTTACTAAGCG

ATTCTGGCAAGAATCAAAAGTCCGTTACTGAATTGGATTCGTTCGCATTTAACCGCA

AGTCCAGAATTGCCAAGCGACCTATCGAGCTACTCGAAGACGAGGAGGACGTGGAC

GTTGGAGCTGCAAAGGTTGTAGACATTGAGCCGACTAACGGAAACAAGAGGCGGAG

ACGGTATCACACCATCGAAGACAGTGACGATGAAGAGTTGGATGAGAAGAAATCGT

TTGGTGATAATCTGACCCCAGGAACGGAAATCGATCAATGTGCAGCCGATGAATCCT

TAGCAAAAAGGTTGCAGGATTTAGAGCACCGGGCAGTTTCTGGCCGTAATCGCCTG

GTTCAAATTTTGTCAGATTCCGATGAAGAAGAAGAGGAAGAAGTAAATCCCATAAC

CATCACCCTACAAAGGTGTGACCAGATTGCAGCATCATTGCGAGAAGAGCTGCAGG

CCAGCAGTTCAAGTGATAACTCGGTTAATGAAGATCGTTATGCAGAGGTTGATGTAG

CAGCAGCAAAAATTGTGAGCCAGGCAGATGTCTGTGCAGCTTGTGGCATTGCCGAG

AATGATACACAACGAATGCTCAAGCCATATCAGCTTGTAGGCGTCAATTTCATGCTG

CTACTTCACCGCAAACATGTTGGGGGTGGCAGTTGCGTATCTTGCCCTTCTGAAACA

FIGURE 2C (con't)

TCTTGATGGAGATGCTGGTCCTCATCTTTTAGTTGCACCTGCTTCTCTTTTAGAAAAC
TGGCAAAGAGAACTCAAGAAGTGGTGTCCTGCATTTAAGGTGGAGCTCTATCATGG
CTCAGGAAGGGCAGCTTTAAACAGGAGGCTTCAGTATGCTGCAAAATCTAAAGGGC
CTGCACCCTTTAACGTGATGCTGACGTGCTACTCCCTTTTGAGAGGCAGAGTGCTC
AGACAAAAGATGACCGCAAATTCCTTAAGAAATGGAATTGGCGCTGTGTGGTTATG
GACGAGGCTCATCTTTTGAAGGACAGAAGCAGCTTTCGCAGCAAAAAGTTGCGAGA
TATAGCTCACAAAGCAATTCAAAGACTGATGCTGACTGGTACTCCACTCCAGAACGA
TTTGCAGGAGCTATGGTCACTTCTGGAGTTCATGATGCCTGATGTGTTCAACACAAA
TGGCGTTGATTTAGATCAATATCTGGGAACCAGGAACGATACCTCAGGGATTGTTGT
GCAGGATACGAACTTGATGACTCGGATCAAAGGAATACTAGGACCTTTTGTATTACG
GAGAATGAAAACTGATGTTATGCGCCAGCTTGTATCAAAGATTCAGGAGGTGGAGT
GTGTGGAGATGCTAGACGAGCAATCAATGGCATATAAAAAGCTGTGAATGAGTAT
AGAGCCCTTGCTGAGTCCGCACGTGCCGCTAAAGCTGCAAAGAAATCCTCAGTTAG
CGTAGTAGATGTCCTTCCTCGTCGACAAGTGACCAATATCTTTACTCAATTGAGAAA
GTCAAGAAATTGGCTAAGAAATTTCATCCATTAGGAGTTTTTGGATATGAATGCGAT
TTGCAGCGTGTGGAGGAAGAATTGACTAGTTACAGCGATTTTGACCTCCACAAGTTG
TGTATTCAATATGGAGGCGCTGCGGGAGGGCAAGGAAAGCTTGATGATGATCATGC
ACTAGCTTCTGCAAAGTGCCAGGCTTTAGCACGTCTACTTCCCAAGTTACAGCAAGG
TGGCCATCGCACATTGATATTCAGCCAGTGGACAAGCATGCTGGATATTTTAGAATG
GGCTCTTGACGTCATGGGTTTTTCTTACACTCGCCTAGATGGAAGCACTCAAGTAAG
TGAACGCCAAACCCTAGTGGACGAGTTCAACAATGACCCTAGCATATTTGTGTTTCT
CCTGTCTACTCGAGCTGGAGGTCAAGGTCTAAATTTAACAGGAGCAGACACAGTCAT
TTTACATGATTTGGACTTCAATCCCCAAATGGATCGACAGGCTGAGGATCGCTGTCA
TCGGATTGGCCAGTCTAAACCTGTTACGATATACCGACTTGTAACAAAAGATACGGT
CGATGAAAGTATATACAAGATAGCCCAACAGAAGCTGGTCCTCGATGCGGCAGTTC

FIGURE 2C (con't, page 2)

TTGAAGGAAAAGAGTCATCCTCTGATCTTAATGATGGTGATGCTCGCACGATGGGTG

AAATTCTTTCTGCATTATTGGATGTTCCACCGACATGATCCTGGAGTCCAGAACACA

TTTTTAATTTATTTTCATTATCTTTATCTGGCACTGCGAGAAAGCTCGTTAACGCAAG

GGC

FIGURE 2D

Nucleotide sequence of the full-length CBF-1 from *Physcomitrella patens* (SEQ ID NO:10)

GGCAGTGAGCGCAACGCAATTAATGTGAGTTAGCTCACTCATTAGGCACCCCAGGCT

TTACACTTTATGCTTCCGGCTCGTATGTTGTGTGGAATTGTGAGCGGATAACAATTTC

ACACAGGAAACAGCTATGACCATGATTACGCCAAGCTCGAAATTAACCCTCACTAA

AGGGAACAAAAGCTGGAGCTCCACCGCGGTGGCGGCCGCTCTAGAACTAGTGGATC

CCCCGGGCTGCAGGAATTCGGCACCAGAGGATTTCGGGGTGAAGGAAGGTGCGATT

GAAGGCGTGCATGAAATTTTGACGCAGCGGGTTGAATCGGAAGGAGTTTTCAGCAG

CTGGAAAGTACCTTCGAGGGTTGATTCATCCAAAGTTTCCATGTGATATGGCTTCAA

AGTATCCGCGAAAATGTAGAGAGCACGCATCACCTGGAGTTGGTGGCAGGGAATCT

ACGCATCGCTTTGATTCAAGGTCGCAGTCGTATTCGTTCTCGGAGAAACCTTACCAC

CGTCGTCGCCGGGATGCGTTTCGTGATATGATCAGCGATTTGGTGCATCAGCCTTCC

GACACTGCCGTGCCTGGTTTCAGGGGAGTGCGCTATCGTCAGAAACTGAACAAGTA

CGTGACAGAGATTCGGCCCACGAGGTGCTCGAAGAAATTTGGCTTGGGACGTATG

ACACTGCAGAGGAAGCAGCGCGTGCCTTTGACATCGGAAATTTGTGTTGTAAGAAA

AACCTGCCGCTCAACTTTCCGGATTCGACTCAGATGTTGCAGAGAATCTCGTCGAAA

TTGACCCCCGAAGCGCAACGAAAAGCCATCGCGACGCTGGCGAAGGACGTAGTGCG

AATGGAAAATGACAGGTCGAAGTTGGGTGGCGGTAACCTGACTACCACAGAGCCCC

CGGTCCATTCCGAGCCTATTACTCAACACCTTGCAGCAGCTGAGATTCGCGCGGTCA

CGTACATTGAACAGCCCCTGGAAATTGTCTACGGAGTGGAAGAATCGGCGACGGCC

FIGURE 2D (con't)

ATGTCGGTAACGGAAGCAAATGCGCGATAACCACTCTTGGAGTTGGGACTTGGG

CAAAGTGATCCTTGATGACGAGCTCTCTGAAATTCCTAACTTCGTCGGAGAACTAGA

TCACGAGGCTATGGATTTCAGTAGTCATGGAGAGGTTTACTACCACCATTATGACTC

TCAGTGAGTCCTACAAGCATATTTTCAACTAGTCAACATCCTCAGTAGATTTAGTCC

ATTACTTTCTGTGTCAGAGCCACGCCTGCGGCTTAGACCGGGAAAGCTTGTATAAAC

TGTAAATTGAGCTCTCGTAGACATGATGTAACACCCAATCACCTGTAAACCCCCAG

CTTGAGATCACAAGGAGTAGAAAACCTGATAGCTTCAAGAGTTTCAACCAAAAAAA

AAAAAAAAAAA

FIGURE 2E

Nucleotide sequence of the full-length HDZ-1 from *Physcomitrella patens* (SEQ ID NO:11)

GCCCTTATCCCGGGCACGAGGGCAAGAGGGGATAGAGACTTGAAAGGAAAGGGGA

GGGAAGGGTGTAAGGAGGCCCACGGGCAGGGTCAAGGTGTCCAATGCACCTGCAAG

ATCAGGAAGCTTGAAGTAGATCAGGGAAAAAACGATGGTAGTCCCTAGTTTACCCG

CCTTCGGAGGACAGAACGCCATGCTCAGACGCAACATTGACAACAACACCGACACT

CTGATTTCTCTGCTTCAAGGGTCCTGCTCCCTCGCGTGAGCATGCAACAAGTGCCG

CGTTCATCGGAGAGTCTCGAAAACATGATGGGGGCTTGTGGGCAAAAACTGCCTTA

CTTTTCGTCATTTGATGGGCCGAGTGTAGAAGAGCAAGAGGATGTCGACGAAGGTA

TCGACGAATTCGCACACCACGTGGAGAAAAGAGGAGATTGTCATTAGAACAAGTG

CGATCATTAGAACGGAATTTTGAAGTGGAAAACAAGCTTGAGCCCGAGAGGAAAAT

GCAACTAGCTAAGGAGCTTGGACTGCGACCTCGTCAAGTGGCGGTGTGGTTCCAGA

ATAGACGGGCAAGGTGGAAAACCAAACAGCTCGAGCACGACTACGAGACCCTGAA

GAAAGCCTACGACAGGCTTAAAGCAGACTTCGAAGCCGTTACTCTAGACACAAATG

CTCTTAAAGCTGAGGTGAGTCGCCTCAAGGGAATCTCTAATGACGACGTCAAGCCCG

CCGAATTCGTTCAGGGCAAGTGTGACACAACGAGTCACCCTGCCTCCCCTGCGCAAT

FIGURE 2E (con't)

CGGAGAGGTCCGACATTGTGTCATCGAGGAATCGCACAACTCCTACCATACATGTGG

ATCCCGTGGCACCCGAGGAAGCCGGCGCTCACTTAACCATGAGCTCGGATAGCAAT

TCCAGCGAGGTCATGGACGCTGATAGCCCTCGCACGAGCCACACCAGCGCTAGTAG

GAGCACTTTGTCCACAAGTGTGGTGCAGCCTGACGAGGGCCTGGGAGTGGCCCAGT

ACCCCACTTTTCTCCCGAAAACTTCGTGGGTCCCAATATGCCAGAGATTTGCGCTG

ATCAGTCACTTGCATCTCAAGTGAAGCTGGAAGAGATCCACAGCTTCAATCCCGACC

AAACCTTCCTGCTCTTGCCCAACTGGTGGGATTGGGCTTGATTCGTTTCTTCATCTGT

ACCCATACACTTTTTCCTTGAATCCAAGTTGAATTCACTTTAGGCAGTGTTTTTTCAC

GATGTACCACTTGTTATTCTTCCACCATGTGCAATCCAACGTCAACCAAAGTTGCAC

CATCGGCGTTAACGCAAGGGC

FIGURE 2F

Nucleotide sequence of the full-length ZF-1 from *Physcomitrella patens* (SEQ ID NO:12)

GAGGAGGGAGTTGGAATCTAGGAGACGTGCATGTGCTGTGGGAGGAATTCTCTGGG

GATTTCGAGGCCTTGTTGTATGTTGTTCAGTAAAGGGAGTAGCTTTTTCCACTTGAAG

GGGCTGGTGCTGCTGTTGTTGCAAGTCTTTTGACATTGAAAGAGGCGGGGTTGCACG

CCCCGGTGTGAGGAAGAGTCTTGTAGTAGGTGGGTTGTGTTGTGCCGTGGTATAGTA

TGCCGAAGCCTTGTGATGCATGCCATGTTTCCAGCGCGGCGGTGTTCTGCCGAGCGG

ACGCTGCCTACCTGTGCGTAGGCTGCGATGGGAAGGTCCACGGGGCCAACAAACTA

GCGTCTCGACACGAGCGCGTGTGGATGTGCGAAGTGTGCGAGGTTGCTCCAGCCGT

GGTGACCTGCAAGGCGGATGCGGCTTCTCTCTGTGTGGCCTGTGACACAGACATCCA

CTCCGCCAACCCGCTAGCGCAGCGTCACGAGAGAGTGCCGGTGACACCTCTGTTCG

AGAGTGCGAGTCCTTTGCGTGGGCCAGATTTCTGCGTGTTGGTGTCAGAGAATGGGT

GCCATGATCTGCTGAAGGGCTGTGAGGACGCCTCGGTTGTGGAAGCTGTCTCGTGGC

TTCTTCCGCACCCTAAGATCTCGACCAACTCTATTATCAGAGGCAGCGCTGCAGCCG

FIGURE 2F (con't)

ACGAGATGGGTTCGTCGCCTTTCCACGACCGGCCCTTTAGTCCCAAGCCCAAGAAAC

AGAAGGTTGAATTGCCCGCGGACATATTCTCTGATGTGGACCCTTTCCTAGACTTGG

ACGATGCAACCGTTACCGGAATTCAACCCGACAGCTTGGTACCAGTCCATATGCCAG

AATGCTCCGAGGACACGGATTCGCTTGCTCACTCCATGGACCCTTCGTTTACTAAAT

TTCCTCTCTCGGCGAAGAGCGGTTACAGCTATGGCACATCTACCCTTACTCAGAGCA

TTTCTTGTTCGTCTCTAGATGCCGCCGTTGTTCCAGACTCCAGTCTCAGCGACATTTC

CACACCCTACCTAGACTCACAAAGCTCCCAAGATATGTCAGCTCGCCTGCCACACCA

GACTGGAGGTCCCATTGACACCGTCGACCGTGAAGCTCGCGTGTTGCGCTACAAGG

AGAAGAGGCAGAAGCGCAAGTTTGAGAAAACAATTCGCTATGCATCAAGGAAGGC

ATATGCTGAGAGCCGGCCGAGGATCAAAGGAAGGTTCGCTAAGAGAACTGATTCCG

ACATGGAGCAGTTTGGCTCAGTGGACTCAAGTTTCGGAGTGGTTCCAAGTTTTTGAG

TTTTCTTGTGTATTGGAGTCTCCATCGAGCAAGGTC

FIGURE 2G

Nucleotide sequence of the full-length LZ-1 from *Physcomitrella patens* (SEQ ID NO:13)

GCCCTTATCCCGGGTGCTCTGGCAGTGGGACGGATTTGGAAGCAACAGGAGGTGGG

CTTGTTGAGCTGCGGAGTATGGAAAAAAGCGGGAAGGTGACGTGAGAGCTGGAATG

ATGGCCGAGTGAGCGTGTTTGTTTTGAGGGGGTAATTAGATGGGAAGATAGAGGTC

GGATGAGTCTGGGCGGTTTGCGTAGAGACGTCGAGGAAAAGGAAAGTGGCGAGGTG

TAGGATCTTGGTGGATTTTTCTCCCCTGAAGCTAGAGACTTCCGGTGCAGAATGTGG

TTAAATGGAACTCAACAGGTGGAATTCATGACATGGAAACCTACTGGGTCTTGTTTG

GAATACAATCTCACGCTGTCGGCTTCTCTTTACGTCATTTTCTTAGGTTCAGAGATAT

AGTAGAAAGGTTTGTGGAATTATCAAGATGGGTGACAACAGTGCAAGTGCAAGGAC

GGATTCATCTTCTGACATGGACGGTGATGCGAAGTTGGATGATGGGCAGCACTTAGC

TAGTGGCGGTGGAAACTCAAACGATTCCAGTCTCGAAACTGGAACGAAGAATGGCG

FIGURE 2G (con't)

ATTCTAAGGTACTAAGGCGGTTAGCACAAAATCGTGAGGCAGCCCGAAAAAGTAGG

CTCAGAAAAAGGCATATGTGCAGCAGTTGGAGTCCAGCCGCATAAAGCTGAACCA

ACTCGAGCAAGAGCTTCAAAGAACTCGGCAACAGCAGGGTCTATACCTTGGACCTG

GTTCGTACAGTGACCAAAATGGTCAGTCGGGTGGAGTTGGTGGAGCAAACGCATAT

AGTTCAGGAGCTGCTGCATTTGACCTGGAGTATGCAAGGTGGGTTGAAGATCATACC

CGGCAGATGAGTGAGCTCCGGGTGGCCCTACAGGCTCATGTCGCTGACGCTGATTTA

CGATTACTAGTGGATGGGAGTATGGCCCACTATGACGACCTCTTTCGGCTCAAGGAC

GCTGCTGCAAAAGCCGACGTGTTTCATCTCGTGTCCGGCATGTGGAAAACTCCTGCA

GAGCGATGCTTTGTATGGATTGGAGGCTGCCGACCCTCTGAGTTACTAAAGATATTA

GTACCTCAAATAGAACCTTTGACAGAGCAGCAGTTGTTAAACATCTGCAATCTGCAG

CAGTCCTCTCAACAGGGTGAAGAGGCCCTCTCAAGGGATGGAACAACTTCAGCA

GTCGCTTGCCGAAACACTGTCTGCCGGTTCTCTTGGCTCAGCAGCAAATGTTGCCAA

CTACATGGGACAGATGGCTGTGGCCATGGGACAACTTGGGAACCTCGAAGGTTTCG

TGCGTCAGGCTGATCATTTGCGACAACAGACGTTACAACAAATGCACCGGGTATTAA

CCATTCGCCAAGTAGCCCGAGGACTTCTTGCGATGGGTGATTACTTTGCTCGTCTTCG

AGCTCTTAGTTCTCTATGGTCCGCCAGGCCTCGTGAATGAGAAACATTGTCGTTTCA

GGCGATGGTGAAGTCTTCGGCGCAGGTATGGAAGCGATATCGCAAGGGC

FIGURE 2H

Nucleotide sequence of the full-length CABF-1 from *Physcomitrella patens* (SEQ ID NO:14)

CAGCATCCTCACATCCCGCCTTCCTCTGCACCCCAGATGTCGCATCCTGGCGCCGTC

ATGCCTTTACAGATGCACTACCCGCAAGCCCAGCAACAGATGATGCCGCAGCTTGGT

GATCAGCAGATGCAGCCGCAGCTTCATTATCAGCAAATTCAGAAACAGCAGCTGTC

CCAGTTCTGGCAGCAGCAAATGCAGGAAATGGAGCAAGTCAATGATTTTAAGACCC

ATCAGCTACCACTGGCACGCATCAAAAAAATCATGAAGTCGGATGAAGATGTTAAG

FIGURE 2H (con't)

ATGATCGCAGCCGAAGCTCCAGTGCTGTTTTCAAAAGCTTGTGAGATGTTTATTTTA
GAATTGACACTGCGCTCTTGGATTCATACGGAGGAAAATAAGCGAAGGACACTACA
AAGAAATGATATTGCAGGGGCTATCACTAGGGGAGACATCTTCGACTTTCTTGTTGA
CATCGTTCCACGTGACGAGTTGAAGGAAGAAGATTTGGGTGTGCCATGGACTGGTGT
TCCAGGGGATGGTTCTGTACCTTACGGAGGAATATTCTATCCACCCATGGCTGGACA
GCAAATGCATCATTCTATGGGGGCTCCTGAGATGATGGTTGGGCAGCCACCAAACCC
ACAAATGATGTATCAGCCTCCACAGACTGCCTTTGTCCCCGAGCAGCAGCAACAGTG
AATGCATTACCACCTAGAGAACGCTGAGCATCGAAGACGGGACAACTCAAGGAAAG
GCTATCGCATCGAGATTCTTTCGTCACGTGGGAATGGTATTTATCATACTGTTGCTA
CCATCTGTCATTCTTATGGCAAAAGGGGTCACAGGATCAGGATTTTACCTTTCACTA
CAGCGCTTTTGTGTTGGCTTTCAACTATATTTTAAGGAAATCGTAGCTGTAGGCGGT
GATGCGACAGTTCTGAGCACTGCTAATTCTAGCAGAGTTTATGTTTGGTTTAGCAAG
TCATGAAGGGCACAAAGGGACCCGACCCCTCCATGGATCTGGTAGAAATTTGTGAA
TAGTGATACTAGTGCAGGCATAATTATTAGCATGTGCAGGAGTTGCTCTTAATGTTA
GGTTCGAGGATCGGGTATCCATTTCTTAGTACCATTGTTTCTTTTATGTCTCCCTGG
TTTTATCTTTCAGACTGAAAAAAAAAAAAAAAAAAAAAAA

FIGURE 3A

Deduced amino acid sequence of CABF-1 from *Physcomitrella patens* (SEQ ID NO:15)

MADSYGHNAGSPESSPHSDNESGGHYRDQDASVREQDRFLPIANVSRIMKKALPSNAKI
SKDAKETVQECVSEFISFITGEASDKCQREKRKTINGDDLLWAMSTLGFEDYVEPLKVY
LHKYRELEGEKASMAKGGDQQGGKESNQGGMGSMGMAGGINGMNGTMNGNMHGH
GIPVSMQMMQQPYAQQAPPGMIYSPHQMMPQYQMPMQSGGNQPRGV*

FIGURE 3B

Deduced amino acid sequence of DBF-1 from *Physcomitrella patens* (SEQ ID NO:16)

MKGIQELSDDEDYIPPVNASRYFNRGKALSKTSSNHANGNGNPNGTSFGVSTSSASDSD
KDKKSEVSGSLLSDSGKNQKSVTELDSFAFNRKSRIAKRPIELLEDEEDVDVGAAKVVDI
EPTNGNKRRRRYHTIEDSDDEELDEKKSFGDNLTPGTEIDQCAADESLAKRLQDLEHRA
VSGRNRLVQILSDSDEEEEEVNPITITLQRCDQIAASLREELQASSSSDNSVNEDRYAEV
DVAAAKIVSQADVCAACGIAENDTQRMLKPYQLVGVNFMLLLHRKHVGGAVAYLALL
KHLDGDAGPHLLVAPASLLENWQRELKKWCPAFKVELYHGSGRAALNRRLQYAAKSK
GPAPFNVMLTCYSLFERQSAQTKDDRKFLKKWNWRCVVMDEAHLLKDRSSFRSKKLR
DIAHKAIQRLMLTGTPLQNDLQELWSLLEFMMPDVFNTNGVDLDQYLGTRNDTSGIVV
QDTNLMTRIKGILGPFVLRRMKTDVMRQLVSKIQEVECVEMLDEQSMAYKKAVNEYR
ALAESARAAKAAKKSSVSVVDVLPRRQVTNIFTQLRKVKKLAKKFHPLGVFGYECDLQ
RVEEELTSYSDFDLHKLCIQYGGAAGGQGKLDDDHALASAKCQALARLLPKLQQGGHR
TLIFSQWTSMLDILEWALDVMGFSYTRLDGSTQVSERQTLVDEFNNDPSIFVFLLSTRAG
GQGLNLTGADTVILHDLDFNPQMDRQAEDRCHRIGQSKPVTIYRLVTKDTVDESIYKIA
QQKLVLDAAVLEGKESSSDLNDGDARTMGEILSALLDVPPT*

FIGURE 3C

Deduced amino acid sequence of DBF-1/variant from *Physcomitrella patens* (SEQ ID NO:23)

MKGIQELSDDEDYIPPVNASRYFNRGKALSKTSSNHANGNGNPNGTSFGVSTSSASDSD
KDKKSEVSGSLLSDSGKNQKSVTELDSFAFNRKSRIAKRPIELLEDEEDVDVGAAKVVDI
EPTNGNKRRRRYHTIEDSDDEELDEKKSFGDNLTPGTEIDQCAADESLAKRLQDLEHRA
VSGRNRLVQILSDSDEEEEEVNPITITLQRCDQIAASLREELQASSSSDNSVNEDRYAEV
DVAAAKIVSQADVCAACGIAENDTQRMLKPYQLVGVNFMLLLHRKHVGG*

FIGURE 3D

Deduced amino acid sequence of CBF-1 from *Physcomitrella patens* (SEQ ID NO:17)

MASKYPRKCREHASPGVGGRESTHRFDSRSQSYSFSEKPYHRRRRDAFRDMISDLVHQP

SDTAVPGFRGVRYRQKLNKYVTEIRPTRCSKKIWLGTYDTAEEAARAFDIGNLCCKKNL

PLNFPDSTQMLQRISSKLTPEAQRKAIATLAKDVVRMENDRSKLGGGNLTTTEPPVHSEP

ITQHLAAAEIRAVTYIEQPLEIVYGVEESATAMSVTEANARDNHSWSWDLGKVILDDEL

SEIPNFVGELDHEAMDFSSHGEVYYHHYDSQ*

FIGURE 3E

Deduced amino acid sequence of HDZ-1 from *Physcomitrella patens* (SEQ ID NO:18)

MVVPSLPAFGGQNAMLRRNIDNNTDTLISLLQGSCSPRVSMQQVPRSSESLENMMGAC

GQKLPYFSSFDGPSVEEQEDVDEGIDEFAHHVEKKRRLSLEQVRSLERNFEVENKLEPER

KMQLAKELGLRPRQVAVWFQNRRARWKTKQLEHDYETLKKAYDRLKADFEAVTLDT

NALKAEVSRLKGISNDDVKPAEFVQGKCDTTSHPASPAQSERSDIVSSRNRTTPTIHVDP

VAPEEAGAHLTMSSDSNSSEVMDADSPRTSHTSASRSTLSTSVVQPDEGLGVAQYPHFS

PENFVGPNMPEICADQSLASQVKLEEIHSFNPDQTFLLLPNWWDWA*

FIGURE 3F

Deduced amino acid sequence of ZF-1 from *Physcomitrella patens* (SEQ ID NO:19)

MPKPCDACHVSSAAVFCRADAAYLCVGCDGKVHGANKLASRHERVWMCEVCEVAPA

VVTCKADAASLCVACDTDIHSANPLAQRHERVPVTPLFESASPLRGPDFCVLVSENGCH

DLLKGCEDASVVEAVSWLLPHPKISTNSIIRGSAAADEMGSSPFHDRPFSPKPKKQKVEL

PADIFSDVDPFLDLDDATVTGIQPDSLVPVHMPECSEDTDSLAHSMDPSFTKFPLSAKSG

YSYGTSTLTQSISCSSLDAAVVPDSSLSDISTPYLDSQSSQDMSARLPHQTGGPIDTVDRE

FIGURE 3F (con't)

ARVLRYKEKRQKRKFEKTIRYASRKAYAESRPRIKGRFAKRTDSDMEQFGSVDSSFGVV
PSF*

FIGURE 3G

Deduced amino acid sequence of LZ-1 from *Physcomitrella patens* (SEQ ID NO:20)

MGDNSASARTDSSSDMDGDAKLDDGQHLASGGGNSNDSSLETGTKNGDSKVLRRLAQ

NREAARKSRLRKKAYVQQLESSRIKLNQLEQELQRTRQQQGLYLGPGSYSDQNGQSGG

VGGANAYSSGAAAFDLEYARWVEDHTRQMSELRVALQAHVADADLRLLVDGSMAHY

DDLFRLKDAAAKADVFHLVSGMWKTPAERCFVWIGGCRPSELLKILVPQIEPLTEQQLL

NICNLQQSSQQGEEALSQGMEQLQQSLAETLSAGSLGSAANVANYMGQMAVAMGQLG

NLEGFVRQADHLRQQTLQQMHRVLTIRQVARGLLAMGDYFARLRALSSLWSARPRE*

FIGURE 3H

Deduced amino acid sequence of CABF-2 from *Physcomitrella patens* (SEQ ID NO:21)

MSHPGAVMPLQMHYPQAQQQMMPQLGDQQMQPQLHYQQIQKQQLSQFWQQQMQ

EMEQVNDFKTHQLPLARIKKIMKSDEDVKMIAAEAPVLFSKACEMFILELTLRSWIHTEE

NKRRTLQRNDIAGAITRGDIFDFLVDIVPRDELKEEDLGVPWTGVPGDGSVPYGGIFYP

PMAGQQMHHSMGAPEMMVGQPPNPQMMYQPPQTAFVPEQQQQ*

FIGURE 4

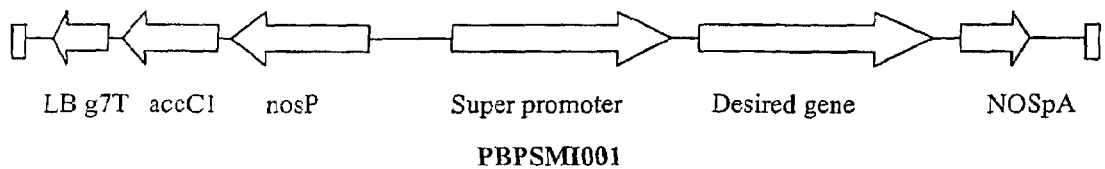

PBPSMI001

SEQUENCE LISTING

```
<160> NUMBER OF SEQ ID NOS: 77

<210> SEQ ID NO 1
<211> LENGTH: 685
<212> TYPE: DNA
<213> ORGANISM: Physcomitrella patens

<400> SEQUENCE: 1
gcaccagcga atccgtctcc gcctccgcct tctgcacgcg tggttgtggt cgacctctcg      60
ccggagcaac aggaaactaa tccctttcc  agcactaaac gattgaagca attttttttt    120
tcttgtgaac tgctcactct ctctctgtta tgaggggatt cgaagcttga aagttatgag    180
ctgaaggttg aggacacgta agcaccagag gacgatcata ctacaattaa cccttgcggg    240
gaaaagccca ggcaaaatag gacggatggc cgacagttac ggccacaacg caggttcacc    300
cgagagcagc ccgcattctg ataacgagtc cggcggccat taccgtgatc aggacgcttc    360
tgtacgggag caagaccggt ttttgcccat cgcaaatgtg agccgaatca tgaagaaagc    420
```

```
attgccatct aatgcgaaga tatcgaaaga cgccaaagag actgtgcagg agtgcgtatc    480
cgagttcatc agtttcatta ctggtgaggc gtccgacaag tgtcagaggg aaaagaggaa    540
gacgatcaac ggggatgact tgctgtgggc catgagtact cttggttttg aagattatgt    600
ggaacctctg aaggtgtacc tacacaagta tcgtgaactg gaggggggaga aggcctctat    660 ggccaagggt ggtgatcaag caggg                                          685
```

<210> SEQ ID NO 2
<211> LENGTH: 517
<212> TYPE: DNA
<213> ORGANISM: Physcomitrella patens
<220> FEATURE:
<221> NAME/KEY: modified_base
<222> LOCATION: (487)..(487)
<223> OTHER INFORMATION: a, c, g, t, unknown or other

<400> SEQUENCE: 2

```
ggcacgaggc ttgatgatga tcatgcacta gcttctgcaa agtgccaggc tttagcacgt     60
ctacttccca agttacagca aggtggccat cgcacattga tattcagcca gtggacaagc    120
atgctggata ttttagaatg ggctcttgac gtcatgggtt tttcttacac tcgcctagat    180
ggaagcactc aagtaagtga acgccaaacc ctagtggacg agttcaacaa tgaccctagc    240
atatttgtgt ttctcctgtc tactcgagct ggaggtcaag gtctaaattt aacaggagca    300
gacacagtca ttttacatga tttggacttc aatccccaaa tggatcgaca ggctgaggat    360
cgctgtcatc ggattggcca gtctaaacct gttacgatat accgacttgt aacaaaagat    420
acggtcgatg aaagtatata caagatagcc aacagaaagc tggtcctcga tgcggcagtt    480
cttgaangaa aagagtcatc ctctgatctt aatgatg                             517
```

<210> SEQ ID NO 3
<211> LENGTH: 1000
<212> TYPE: DNA
<213> ORGANISM: Physcomitrella patens

<400> SEQUENCE: 3

```
ggcacgagct gatactaatt gcacgaggtt ttctcaaatg tgttttgggg tacaggaagg     60 tggagggggaa tttgtaagtg acagagacgt ggtgggagtg ggaggagtgt gaggaatcga    120
gctagcacct aaaggatttc ggggtgaagg aaggtgcgat tgaaggcgtg catgaaattt    180
tgacgcagcg ggttgaatcg gaaggagttt tcagcagctg gaaagtacct tcgagggttg    240
attcatccaa agtttccatg tgatatggct tcaaagtatc cgcgaaaatg tagagagcac    300
gcatcacctg gagttggtgg cagggaatct acgcatcgct ttgattcaag gtcgcagtcg    360
tattcgttct cggagaaacc ttaccaccgt cgtcgccggg atgcgtttcg tgatatgatc    420
agcgatttgg tgcatcagcc ttccgacact gccgtgcctg gtttcagggg agtgcgctat    480
cgtcagaaac tgaacaagta cgtgacagag attcggccca cgaggtgctc gaagaaaatt    540
tggcttggga cgtatgacac tgcagaggaa gcagcgcgtg cctttgacat cggaaatttg    600
tgttgtaaga aaaacctgcc gctcaacttt ccggattcga ctcagatgtt gcagagaatc    660
tcgtcgaaat tgaccccccga agcgcaacga aaagccatcg cgacgctggc gaaggacgta    720
gtgcgaatgg aaaatgacag gtcgaagttg ggtggcggta acctgactac cacagagccc    780
ccggtccatt ccgagcctat tactcaacac cttgcagcag ctgagattcg cgcggtcacg    840
tacattgaac agccccctgga aattgtctac ggagtggaag aatcggcgac ggccatgtcg    900
```

```
gtaacggaag caaatgcgcg cgataaccac tcttggagtt gggacttggg caaagtgatc    960
cttgatgacg agctctctga aattcctaac ttcgtcggag                         1000

<210> SEQ ID NO 4
<211> LENGTH: 1343
<212> TYPE: DNA
<213> ORGANISM: Physcomitrella patens
<220> FEATURE:
<221> NAME/KEY: modified_base
<222> LOCATION: (1287)..(1287)
<223> OTHER INFORMATION: a, c, g, t, unknown or other

<400> SEQUENCE: 4
ggcacgaggg caagagggga tagagacttg aaaggaaagg gagggaaggg tgtaaggagg     60
cccacgggca gggtcaaggt gtccaatgca cctgcaagat caggaagctt gaagtagatc    120
agggaaaaaa cgatggtagt ccctagttta cccgccttcg gaggacagaa cgccatgctc    180
agacgcaaca ttgacaacaa caccgacact ctgatttctc tgcttcaagg gtcctgctcc    240
cctcgcgtga gcatgcaaca aggatatgtt gcagtgccgc gttcatcgga gagtctcgaa    300
aacatgatgg gggcttgtgg gcaaaaactg ccttactttt cgtcatttga tgggccgagt    360
gtagaagagc aagaggatgt cgacgaaggt atcgacgaat tcgcacacca cgtggagaaa    420
aaggaggaga ttgtcattag aacaagtgcg atcattagaa cggaattttg aagtggaaaa    480
caagcttgag cccgagagga aaatgcaact agctaaggag cttggactgc aacctcgtca    540
agtggcggtg tggttccaga atagacgggc aaggtgaaaa accaaacagc tcgagcgcga    600
ctacgagacc ctgaagaaag cctacgacag gcttaaagca gacttcgaag ccgttactct    660
agacacaagt gctcttaaag ctgaggtgag tcgcctcaag ggaatctcta atgcacgacg    720
tcaagcccgc cgaattcgtt cagggcaagt gtgacacaac gagtcaccct gcctcccctg    780
cgcaatcgga gaggtccgac attgtgtcat cgaggaatcg cacaactcct accatacatg    840
tggatcccgt ggcacccgag gaagccggcg ctcacttaac catgagctcg gatagcaatt    900
ccagcgaggt catggacgct gatagccctc gcacgagcca caccagcgct agtaggagca    960
ctttgtccac aagtgtggtg cagcctgacg agggcctggg agtggcccag taccccccact   1020 tttctcccga aaacttcgtg ggtcccaata tgccagagat ttgcgctgat cagtcacttg   1080
catctcaagt gaagctggaa gagatccaca gcttcaatcc cgaccaaacc ttcctgctct   1140
tgcccaactg gtgggattgg gcttgattcg tttcttcatc tgtacccata cactttttcc   1200
ttgaatccaa gttgaattca ctttaggcag tgtttttttca cgatgtacca cttgttattc   1260
ttccaccatg tgcaatccaa cgtcaancaa agttgcacat cggcgatcat tggtgacgat   1320
gtcgagcatc gatcgtcaca tgc                                           1343

<210> SEQ ID NO 5
<211> LENGTH: 1157
<212> TYPE: DNA
<213> ORGANISM: Physcomitrella patens

<400> SEQUENCE: 5
gcacgagctc ggttgtggaa gctgtctcgt ggcttcttcc gcaccctaag atctcgacca     60
actctattat cagaggcagc gctgcagccg acgagatggg ttcgtcgcct ttccacgacc    120
ggccctttag tcccaagccc aagaaacaga aggttgaatt gcccgcggac atattctctg    180
atgtggaccc tttcctagac ttggacgatg caaccgttac cggaattcaa cccgacagct    240
tggtaccagt ccatatgcca gaatgctccg aggacacgga ttcgcttgct cactccatgg    300
```

```
acccttcgtt tactaaattt cctctctcgg cgaagagcgg ttacagctat ggcacatcta    360
cccttactca gagcatttct tgttcgtctc tagatgccgc cgttgttcca gactccagtc    420
tcagcgacat ttccacaccc tacctagact cacaaagctc caagatatg tcagctcgcc     480 tgccacacca gactggaggt cccattgaca ccgtcgaccg tgaagctcgc gtgttgcgct    540
acaaggagaa gaggcagaag cgcaagtttg agaaaacaat tcgctatgca tcaaggaagg    600
catatgctga gagccggccg aggatcaaag gaaggttcgc taagagaact gattccgaca    660
tggagcagtt tggctcagtg gactcaagtt tcggagtgg tccaagtttt tgagttttct      720
tgtgtattgg agtctccatc gagcaaggtc atctgaaatg gaagctgct gtgtaacata     780 gaggagctgc tgtaagaact gtgtagagcc atccaagtgg tgaagcacct gaaaaagtgg    840
cagcaatgta aattgttcag actctcaatg gtcaccagta ccaagtcatg ccattctata    900
atccctttca gaacacgatt aaatgccttg tggacagtac aggatgtagt cagagttcta    960
gtagtggttt ttttctattt ttcttttgt tgattgagag ctttcggaac ggtgagaact    1020
tcgtggcgcg aatcctctgt cctgcgatcg ttatgatgca gcgaattctt ccgatcttga   1080
tgtatttcaa cacttccata atgctcttgg attttgggt catttcctca gaaggtgttg     1140
agctaacaaa aaaaaaa                                                   1157

<210> SEQ ID NO 6
<211> LENGTH: 374
<212> TYPE: DNA
<213> ORGANISM: Physcomitrella patens

<400> SEQUENCE: 6
cttcaaagaa ctcggcaaca gcagggtcta taccttggac ctggttcgta cagtgaccaa     60
aatggtcagt cgggtggagt tggtggagca aacgcatata gttcaggagc tgctgcattt    120
gacctggagt atgcaaggtg ggttgaagat catacccgc agatgagtga gctccgggtg     180
gccctacagg ctcatgtcgc tgacgctgat ttacgattac tagtggatgg gagtatggcc    240
cactatgacg acctctttcg gctcaaggac gctgctgcaa aagccgacgt gtttcatctc    300
gtgtccggca tgtggaaaac tcctgcagag cgatgctttg tatggattgg aggctgccga    360
ccctctgagt tact                                                      374

<210> SEQ ID NO 7
<211> LENGTH: 461
<212> TYPE: DNA
<213> ORGANISM: Physcomitrella patens

<400> SEQUENCE: 7
catcctggcg ccgtcatgcc tttacagatg cactacccgc aagcccagca acagatgatg     60
ccgcagcttg tgatcagca gatgcagccg cagcttcatt atcagcaaat tcagaaacag     120
cagctgtccc agttctggca gcagcaaatg caggaaatgg agcaagtcaa tgattttaag    180
acccatcagc taccactggc acgcatcaaa aaaatcatga gtcggatgaa agatgttaag    240
atgatcgcag ccgaagctcc agtgctgttt tcaaaagctt gtgagatgtt tattttagaa    300
ttgacactgc gctcttggat tcatacggag gaaaataagc gaaggacact acaaagaaat    360
gatattgcag gggctatcac taggggagac atcttcgact ttcttgttga catcgttcca    420
cgtgacgagt tgaaggaaga agatttgggt gtgccatgga c                        461

<210> SEQ ID NO 8
```

<211> LENGTH: 1347
<212> TYPE: DNA
<213> ORGANISM: Physcomitrella patens

<400> SEQUENCE: 8

```
ggcaccagcg aatccgtctc cgcctccgcc ttctgcacgc gtggttgtgg tcgacctctc      60
gccggagcaa caggaaacta atcccttttc cagcactaaa cgattgaagc aatttttttt     120
ttcttgtgaa ctgctcactc tctctctgtt atgagqggat tcgaagcttg aaagttatga     180
gctgaaggtt gaggacacgt aagagcgaag gacgatcata ctacaattaa cccttgcggg     240
gaaaagccca ggcaaaatag gacgqatggc cgacagttac ggccacaacg caggttcacc     300
cgagagcagc ccgcattctg ataacgagtc cggcggccat taccgtgatc aggacgcttc     360
tgtacgggag caagaccggt ttttgcccat cgcaaatgtg agccgaatca tgaagaaagc     420
attgccatct aatgcgaaga tatcgaaaga cgccaaagag actgtgcagg agtgcgtatc     480
cgagttcatc agtttcatta ctggtgaggc gtccgacaca tgtcagaggg aaaagaggaa     540
gacgatcaac ggggatgact tgctgtgggc catgagtact cttggttttg aagattatgt     600
ggaacctctg aaggtgtacc tacacaagta tcgtgaactg gagggggaga aggcctctat     660
ggccaagggt ggtgatcagc agggaggaaa agagagcaac caaggaggta tggggtcgat     720
gggcatggca ggcggaatca acggcatgaa cggaacgatg aacgggaaca tgcatgggca     780
tggaattccc gtatcgatgc agatgatgca acagccgtac gcgcagcagg cacctccggg     840
gatgatatat tctcctcatc aaatgatgcc gcaataccag atgccgatgc agtctggtgg     900
aaaccaaccc cgcggagtgt aagagttttc actggcagga ggctttggaa gtggggatat     960
tgtcgacagc gtgatggggt gttttggagc atgggcaggg cattatggtg ctgttgaaac    1020
agtgatgggt gggtcatgtg aagtgttggc gactgttgaa tgatgaaaac atagaagtga    1080
tgtcgttgaa gctcggggag tttcaagtga aggaggagc actttttgtt tggaaaggag     1140
cgtaccgggt ctggcagtgt acattctgaa tgatagttat ctgtgctgat ttttcttggc    1200
cttggcaata cgaggggggtt gaatattttg ctttgaattc gttgacattt caaccttttc    1260
tatgtgaaaa ggctctgtag gatgcaagat aaggaaagac atgcagattg ataaaaaaaa    1320
aaaaaaaaaa aaaaaaaaaa aaaaaaa                                        1347
```

<210> SEQ ID NO 9
<211> LENGTH: 2838
<212> TYPE: DNA
<213> ORGANISM: Physcomitrella patens

<400> SEQUENCE: 9

```
gcccttatcc cgggcgatgg tgcgttcgag atcgtaaggt tgccgacgaa ggcgtaactt      60
ggaagtcctc tgtgtcccgg cgatgtccca atgttggccc gattttctgt ttttagcgag     120
ctgtgggcta gtttgtgggt atgatccggg gaatgagacg agatgtctgt ctgagtgaga     180
ccactctagg ggctgttgga ggatgaggag ggaagcgcag aagttggcca ttcttttcag     240
tgactggact ctgtgcgagt ggtcagcttt cgggagctgc tgttgcattg accggtgatt     300
ctttcgagat cgtagagaca gcagctggca agggttttgg gaggcttttc aaatgaaggg     360
cattcaagag ctttcagatg atgaagatta tattccgcct gtcaatgcat cgcgatattt     420
caacaggggc aaagcgctct caaagacatc atccaatcat gccaatggaa atggaaatcc     480
aaacggaacg agttttggag tttcaacttc ttcagcaagt gactctgaca agataagaa      540
atccgaagtt tcaggttctt tactaagcga ttctggcaag aatcaaaagt ccgttactga     600
```

```
attggattcg ttcgcatttc accgcaagtc cagaattgcc aagcgaccta tcgagctact    660
cgaagacgag gaggacgtgg acgttggagc tgcaaaggtt gtagacattg agccgactaa    720
cggaaacaag aggcggagac ggtatcacac catcgaagac agtgacgatg aagagttgga    780
tgagaagaaa tcgtttggtg ataatctgac cccaggaacg gaaatcgatc aatgtgcagc    840
cgatgaatcc ttagcaaaaa ggttgcagga tttagcacac cgggcagttt ctggccgtaa    900
tcgcctggtt caaattttgt cagattccga tgaagaagaa gaggaagaag taaatcccat    960
aaccatcacc ctacaaaggt gtgaccagat tgcagcatca ttgcgagaag agctgcaggc   1020
cagcagttca agtgataact cggttaatga agatcgttat gcagaggttg atgtagcagc   1080
agcaaaaatt gtgagccagg cagatgtctg tgcagcttgt ggcattgccg agaatgatac   1140
acaacgaatg ctcaagccat atcagcttgt aggcgtcaat ttcatgctgc tacttcaccg   1200
caaacatgtt gggggtgcag ttgcgtatct tgcccttctg aaacatcttg atggagatgc   1260
tggtcctcat cttttagttg cacctgcttc tcttttagaa aactggcaaa gagaactcaa   1320
gaagtggtgt cctgcattta aggtggagct ctatcatggc tcaggaaggg cagctttaaa   1380
caggaggctt cagtatgctg caaaatctaa agggcctgca ccctttaacg tgatgctgac   1440
gtgctactcc cttttgaga ggcagagtgc tcagacaaaa gatgaccgca aattccttaa    1500
gaaatggaat tggcgctgtg tggttatgga cgaggctcat cttttgaagg acagaagcag   1560
ctttcgcagc aaaaagttgc gagatatagc tcacaaagca attcaaagac tgatgctgac   1620
tggtactcca ctccagaacg atttgcagga gctatggtca cttctggagt tcatgatgcc   1680
tgatgtgttc aacacaaatg gcgttgattt agatcaatat ctgggaacca ggaacgatac   1740
ctcagggatt gttgtgcagg atacgaactt gatgactcgg atcaaggaa tactaggacc    1800 ttttgtatta cggagaatga aaactgatgt tatgcgccag cttgtatcaa agattcagga   1860
ggtggagtgt gtggagatgc tagacgagca atcaatggca tataaaaaag ctgtgaatga   1920
gtatagagcc cttgctgagt ccgcacgtgc cgctaaagct gcaaagaaat cctcagttag   1980
cgtagtagat gtccttcctc gtcgacaagt gaccaatatc tttactcaat gagaaaggt    2040 caagaaattg gctaagaaat ttcatccatt aggagttttt ggatatgaat gcgatttgca   2100
gcgtgtggag gaagaattga ctagttacag cgatttgac ctccacaagt tgtgtattca    2160
atatggaggc gctgcgggag ggcaaggaaa gcttgatgat gatcatgcac tagcttctgc   2220 aaaagtgccag gctttagcac gtctacttcc caagttacag caaggtggcc atcgcacatt   2280
gatattcagc cagtggacaa gcatgctgga tatttagaa tgggctcttg acgtcatggg    2340 ttttcttac actcgcctag atggaagcac tcaagtaagt gaacgccaaa ccctagtgga   2400
cgagttcaac aatgacccta gcatatttgt gtttctcctg tctactcgag ctggaggtca   2460
aggtctaaat ttaacaggag cagacacagt cattttacat gatttggact tcaatcccca   2520
aatggatcga caggctgagg atcgctgtca tcggattggc cagtctaaac ctgttacgat   2580
ataccgactt gtaacaaaag atacggtcga tgaaagtata tacaagatag cccaacagaa   2640
gctggtcctc gatgcggcag ttcttgaagg aaaagagtca tcctctgatc ttaatgatgg   2700
tgatgctcgc acgatgggtg aaattctttc tgcattattg gatgttccac cgacatgatc   2760
ctggagtcca gaacacattt ttaatttatt ttcattatct ttatctggca ctgcgagaaa   2820
gctcgttaac gcaagggc                                                 2838
```

<210> SEQ ID NO 10

```
<211> LENGTH: 1424
<212> TYPE: DNA
<213> ORGANISM: Physcomitrella patens

<400> SEQUENCE: 10
ggcagtgagc gcaacgcaat taatgtgagt tagctcactc attaggcacc ccaggcttta      60
cactttatgc ttccggctcg tatgttgtgt ggaattgtga gcggataaca atttcacaca     120
ggaaacagct atgaccatga ttacgccaag ctcgaaatta accctcacta aagggaacaa     180
aagctggagc tccaccgcgg tggcggccgc tctagaacta gtggatcccc cgggctgcag     240
gaattcggca ccagaggatt tcggggtgaa ggaaggtgcg attgaaggcg tgcatgaaat     300
tttgacgcag cgggttgaat cggaaggagt tttcagcagc tggaaagtac cttcgagggt     360
tgattcatcc aaagtttcca tgtgatatgg cttcaaagta tccgcgaaaa tgtagagagc     420
acgcatcacc tggagttggt ggcagggaat ctacgcatcg ctttgattca aggtcgcagt     480
cgtattcgtt ctcggagaaa ccttaccacc gtcgtcgccg ggatgcgttt cgtgatatga     540
tcagcgattt ggtgcatcag ccttccgaca ctgccgtgcc tggtttcagg ggagtgcgct     600
atcgtcagaa actgaacaag tacgtgacag agattcggcc cacgaggtgc tcgaagaaaa     660
tttggcttgg gacgtatgac actgcagagg aagcagcgcg tgcctttgac atcggaaatt     720
tgtgttgtaa gaaaaacctg ccgctcaact ttccggattc gactcagatg ttgcagagaa     780
tctcgtcgaa attgacccccc gaagcgcaac gaaaagccat cgcgacgctg gcgaaggacg     840
tagtgcgaat ggaaaatgac aggtcgaagt tgggtggcgg taacctgact accacagagc     900
ccccggtcca ttccgagcct attactcaac accttgcagc agctgagatt cgcgcggtca     960
cgtacattga acagcccctg gaaattgtct acggagtgga agaatcggcg acggccatgt    1020
cggtaacgga agcaaatgcg cgcgataacc actcttggag ttgggacttg gcaaagtga    1080 tccttgatga cgagctctct gaaattccta acttcgtcgg agaactagat cacgaggcta    1140
tggatttcag tagtcatgga gaggtttact accaccatta tgactctcag tgagtcctac    1200
aagcatattt tcaactagtc aacatcctca gtagatttag tccattactt tctgtgtcag    1260
agccacgcct gcggcttaga ccgggaaagc ttgtataaac tgtaaattga gctctcgtag    1320
acatgatgta acacccaatc acctgtaaac cccccagctt gagatcacaa ggagtagaaa    1380
acctgatagc ttcaagagtt tcaaccaaaa aaaaaaaaaa aaaa                     1424

<210> SEQ ID NO 11
<211> LENGTH: 1318
<212> TYPE: DNA
<213> ORGANISM: Physcomitrella patens

<400> SEQUENCE: 11
gcccttatcc cgggcacgag ggcaagaggg gatagagact tgaaaggaaa ggggagggaa      60
gggtgtaagg aggcccacgg gcagggtcaa ggtgtccaat gcacctgcaa gatcaggaag     120
cttgaagtag atcagggaaa aaacgatggt agtccctagt ttacccgcct tcggaggaca     180
gaacgccatg ctcagacgca acattgacaa caacaccgac actctgattt ctctgcttca     240
agggtcctgc tcccctcgcg tgagcatgca acaagtgccg cgttcatcgg agagtctcga     300
aaacatgatg ggggcttgtg ggcaaaaact gccttacttt tcgtcatttg atgggccgag     360
tgtagaagag caagaggatg tcgacgaagg tatcgacgaa ttcgcacacc acgtggagaa     420
aaagaggaga ttgtcattag aacaagtgcg atcattagaa cggaattttg aagtggaaaa     480
caagcttgag cccgagagga aaatgcaact agctaaggag cttggactgc gacctcgtca     540
```

-continued

```
agtggcggtg tggttccaga atagacgggc aaggtggaaa accaaacagc tcgagcacga    600
ctacgagacc ctgaagaaag cctacgacag gcttaaagca gacttcgaag ccgttactct    660
agacacaaat gctcttaaag ctgaggtgag tcgcctcaag ggaatctcta atgacgacgt    720
caagcccgcc gaattcgttc agggcaagtg tgacacaacg agtcaccctg cctcccctgc    780
gcaatcggag aggtccgaca ttgtgtcatc gaggaatcgc acaactccta ccatacatgt    840
ggatcccgtg gcacccgagg aagccggcgc tcacttaacc atgagctcgg atagcaattc    900
cagcgaggtc atggacgctg atagccctcg cacgagccac accagcgcta gtaggagcac    960
tttgtccaca agtgtggtgc agcctgacga gggcctggga gtggcccagt accccacctt    1020
ttctcccgaa aacttcgtgg gtcccaatat gccagagatt tgcgctgatc agtcacttgc    1080
atctcaagtg aagctggaag agatccacag cttcaatccc gaccaaacct tcctgctctt    1140
gcccaactgg tgggattggg cttgattcgt tccttcatct gtacccatac acttttctcct  1200 tgaatccaag ttgaattcac tttaggcagt gttttttcac gatgtaccac ttgttattct    1260
tccaccatgt gcaatccaac gtcaaccaaa gttgcaccat cggcgttaac gcaagggc      1318
```

<210> SEQ ID NO 12
<211> LENGTH: 1341
<212> TYPE: DNA
<213> ORGANISM: Physcomitrella patens

<400> SEQUENCE: 12

```
gaggagggag ttggaatcta ggagacgtgc atgtgctgtg ggaggaattc tctggggatt     60
tcgaggcctt gttgtatgtt gttcagtaaa gggagtagct ttttccactt gaaggggctg    120
gtgctgctgt tgttgcaagt cttttgacat tgaaagaggc ggggttgcac gccccggtgt    180
gaggaagagt cttgtagtag gtgggttgtg ttgtgccgtg gtatagtatg ccgaagcctt    240
gtgatgcatg ccatgtttcc agcgcggcgg tgttctgccg agcggacgct gcctacctgt    300
gcgtaggctg cgatgggaag gtccacgggg ccaacaaact agcgtctcga cacgagcgcg    360
tgtggatgtg cgaagtgtgc gaggttgctc cagccgtggt gacctgcaag gcggatgcgg    420
cttctctctg tgtggcctgt gacacagaca tccactccgc caacccgcta gcgcagcgtc    480
acgagagagt gccggtgaca cctctgttcg agagtgcgag tcctttgcgt gggccagatt    540
tctgcgtgtt ggtgtcagag aatgggtgcc atgatctgct gaagggctgt gaggacgcct    600
cggttgtgga agctgtctcg tggcttcttc cgcaccctaa gatctcgacc aactctatta    660
tcagaggcag cgctgcagcc gacgagatgg ttcgtcgcc tttccacgac cggcccttta    720
gtcccaagcc caagaaacag aaggttgaat gcccgcgga catattctct gatgtggacc    780 cttttcctaga cttggacgat gcaaccgtta ccggaattca acccgacagc ttggtaccag    840
tccatatgcc agaatgctcc gaggacacgg attcgcttgc tcactccatg gacccttcgt    900
ttactaaatt tcctctctcg gcgaagagcg gttacagcta tggcacatct acccttactc    960
agagcatttc ttgttcgtct ctagatgccg ccgttgttcc agactccagt ctcagcgaca    1020
tttccacacc ctacctagac tcacaaagct cccaagatat gtcagctcgc ctgccacacc    1080
agactggagg tccattgac accgtcgacc gtgaagctcg cgtgttgcgc tacaaggaga    1140
agaggcagaa gcgcaagttt gagaaaacaa ttcgctatgc atcaaggaag gcatatgctg    1200
agagccggcc gaggatcaaa ggaaggttcg ctaagagaac tgattccgac atggagcagt    1260
ttggctcagt ggactcaagt ttcggagtgg ttccaagttt tgagttttc ttgtgtattg     1320
```

```
                                    -continued
gagtctccat cgagcaaggt c                                       1341

<210> SEQ ID NO 13
<211> LENGTH: 1521
<212> TYPE: DNA
<213> ORGANISM: Physcomitrella patens

<400> SEQUENCE: 13
gcccttatcc cgggtgctct ggcagtggga cggatttgga agcaacagga ggtgggcttg     60
ttgagctgcg gagtatggaa aaaagcggga aggtgacgtg agagctggaa tgatggccga    120
gtgagcgtgt ttgttttgag ggggtaatta gatgggaaga tagaggtcgg atgagtctgg    180
gcggtttgcg tagagacgtc gaggaaaagg aaagtggcga ggtgtaggat cttggtggat    240
ttttctcccc tgaagctaga gacttccggt gcagaatgtg gttaaatgga actcaacagg    300
tggaattcat gacatggaaa cctactgggt cttgtttgga atacaatctc acgctgtcgg    360
cttctcttta cgtcattttc ttaggttcag agatatagta gaaaggtttg tggaattatc    420
aagatgggtg acaacagtgc aagtgcaagg acggattcat cttctgacat ggacggtgat    480
gcgaagttgg atgatgggca gcacttagct agtggcggtg gaaactcaaa cgattccagt    540
ctcgaaactg gaacgaagaa tggcgattct aaggtactaa ggcggttagc acaaaatcgt    600
gaggcagccc gaaaaagtag gctcagaaaa aaggcatatg tgcagcagtt ggagtccagc    660
cgcataaagc tgaaccaact cgagcaagag cttcaaagaa ctcggcaaca gcagggtcta    720
taccttggac ctggttcgta cagtgaccaa aatggtcagt cgggtggagt tggtggagca    780
aacgcatata gttcaggagc tgctgcattt gacctggagt atgcaaggtg ggttgaagat    840
catacccggc agatgagtga gctccgggtg gccctacagg ctcatgtcgc tgacgctgat    900
ttacgattac tagtggatgg gagtatggcc cactatgacg acctctttcg gctcaaggac    960
gctgctgcaa aagccgacgt gtttcatctc gtgtccggca tgtggaaaac tcctgcagag   1020
cgatgctttg tatggattgg aggctgccga ccctctgagt tactaaagat attagtacct   1080
caaatagaac ctttgacaga gcagcagttg ttaaacatct gcaatctgca gcagtccctct   1140 caacagggtg aagaggccct ctctcaaggg atggaacaac ttcagcagtc gcttgccgaa   1200
acactgtctg ccggttctct tggctcagca gcaaatgttg ccaactacat gggacagatg   1260
gctgtggcca tgggacaact tgggaacctc gaaggtttcg tgcgtcaggc tgatcatttg   1320
cgacaacaga cgttacaaca aatgcaccgg gtattaacca ttcgccaagt agcccgagga   1380
cttcttgcga tgggtgatta ctttgctcgt cttcgagctc ttagttctct atggtccgcc   1440
aggcctcgtg aatgagaaac attgtcgttt caggcgatgg tgaagtcttc ggcgcaggta   1500
tggaagcgat atcgcaaggg c                                             1521

<210> SEQ ID NO 14
<211> LENGTH: 1176
<212> TYPE: DNA
<213> ORGANISM: Physcomitrella patens

<400> SEQUENCE: 14
cagcatcctc acatcccgcc ttcctctgca ccccagatgt cgcatcctgg cgccgtcatg     60
cctttacaga tgcactaccc gcaagcccag caacagatga tgccgcagct tggtgatcag    120
cagatgcagc cgcagcttca ttatcagcaa attcagaaac agcagctgtc ccagttctgg    180
cagcagcaaa tgcaggaaat ggagcaagtc aatgatttta agacccatca gctaccactg    240
gcacgcatca aaaaaatcat gaagtcggat gaagatgtta agatgatcgc agccgaagct    300
```

```
ccagtgctgt tttcaaaagc ttgtgagatg tttattttag aattgacact gcgctcttgg    360
attcatacgg aggaaaataa gcgaaggaca ctacaaagaa atgatattgc agggctatc     420 actaggggag acatcttcga ctttcttgtt gacatcgttc cacgtgacga gttgaaggaa    480
gaagatttgg gtgtgccatg gactggtgtt ccaggggatg gttctgtacc ttacggagga    540
atattctatc cacccatggc tggacagcaa atgcatcatt ctatggggc tcctgagatg     600 atggttgggc agccaccaaa cccacaaatg atgtatcagc ctccacagac tgcctttgtc    660
cccgagcagc agcaacagtg aatgcattac cacctagaga cgctgagca tcgaagacgg     720 gacaactcaa ggaaagggct atcgcatcga gattctttcg tcacgtggga atggtattta    780
tcatactgtt gctaccatct gtcattctta tggcaaaagg ggtcacagga tcaggatttt    840 accttcact acagcgcttt tgtgttggct ttcaactata ttttaaggaa atcgtagctg     900
taggcggtga tgcgacagtt ctgagcactg ctaattctag cagagtttat gtttggttta    960
gcaagtcatg aagggcacaa agggacccga ccctccatg gatctggtag aaatttgtga     1020
atagtgatac tagtgcaggc ataattatta gcatgtgcag gagttgctct taatgttagg    1080
ttcgaggatc gggtatccat tttcttagta ccattgtttc ttttatgtct ccctggtttt    1140
atctttcaga ctgaaaaaaa aaaaaaaaaa aaaaaa                              1176
```

<210> SEQ ID NO 15
<211> LENGTH: 218
<212> TYPE: PRT
<213> ORGANISM: Physcomitrella patens

<400> SEQUENCE: 15

```
Met Ala Asp Ser Tyr Gly His Asn Ala Gly Ser Pro Glu Ser Ser Pro
1               5                   10                  15

His Ser Asp Asn Glu Ser Gly Gly His Tyr Arg Asp Gln Asp Ala Ser
            20                  25                  30

Val Arg Glu Gln Asp Arg Phe Leu Pro Ile Ala Asn Val Ser Arg Ile
        35                  40                  45

Met Lys Lys Ala Leu Pro Ser Asn Ala Lys Ile Ser Lys Asp Ala Lys
    50                  55                  60

Glu Thr Val Gln Glu Cys Val Ser Glu Phe Ile Ser Phe Ile Thr Gly
65                  70                  75                  80

Glu Ala Ser Asp Lys Cys Gln Arg Glu Lys Arg Lys Thr Ile Asn Gly
                85                  90                  95

Asp Asp Leu Leu Trp Ala Met Ser Thr Leu Gly Phe Glu Asp Tyr Val
            100                 105                 110

Glu Pro Leu Lys Val Tyr Leu His Lys Tyr Arg Glu Leu Glu Gly Glu
        115                 120                 125

Lys Ala Ser Met Ala Lys Gly Gly Asp Gln Gln Gly Gly Lys Glu Ser
    130                 135                 140

Asn Gln Gly Gly Met Gly Ser Met Gly Met Ala Gly Gly Ile Asn Gly
145                 150                 155                 160

Met Asn Gly Thr Met Asn Gly Asn Met His Gly His Gly Ile Pro Val
                165                 170                 175

Ser Met Gln Met Met Gln Gln Pro Tyr Ala Gln Ala Pro Pro Gly
            180                 185                 190

Met Ile Tyr Ser Pro His Gln Met Met Pro Gln Tyr Gln Met Pro Met
        195                 200                 205

Gln Ser Gly Gly Asn Gln Pro Arg Gly Val
```

```
210                 215

<210> SEQ ID NO 16
<211> LENGTH: 801
<212> TYPE: PRT
<213> ORGANISM: Physcomitrella patens

<400> SEQUENCE: 16

Met Lys Gly Ile Gln Glu Leu Ser Asp Asp Glu Asp Tyr Ile Pro Pro
1               5                   10                  15

Val Asn Ala Ser Arg Tyr Phe Asn Arg Gly Lys Ala Leu Ser Lys Thr
            20                  25                  30

Ser Ser Asn His Ala Asn Gly Asn Gly Asn Pro Asn Gly Thr Ser Phe
        35                  40                  45

Gly Val Ser Thr Ser Ser Ala Ser Asp Ser Asp Lys Asp Lys Lys Ser
    50                  55                  60

Glu Val Ser Gly Ser Leu Leu Ser Asp Ser Gly Lys Asn Gln Lys Ser
65                  70                  75                  80

Val Thr Glu Leu Asp Ser Phe Ala Phe Asn Arg Lys Ser Arg Ile Ala
                85                  90                  95

Lys Arg Pro Ile Glu Leu Leu Glu Asp Glu Asp Val Asp Val Gly
            100                 105                 110

Ala Ala Lys Val Val Asp Ile Glu Pro Thr Asn Gly Asn Lys Arg Arg
        115                 120                 125

Arg Arg Tyr His Thr Ile Glu Asp Ser Asp Asp Glu Glu Leu Asp Glu
    130                 135                 140

Lys Lys Ser Phe Gly Asp Asn Leu Thr Pro Gly Thr Glu Ile Asp Gln
145                 150                 155                 160

Cys Ala Ala Asp Glu Ser Leu Ala Lys Arg Leu Gln Asp Leu Glu His
                165                 170                 175

Arg Ala Val Ser Gly Arg Asn Arg Leu Val Gln Ile Leu Ser Asp Ser
            180                 185                 190

Asp Glu Glu Glu Glu Glu Val Asn Pro Ile Thr Ile Thr Leu Gln
        195                 200                 205

Arg Cys Asp Gln Ile Ala Ala Ser Leu Arg Glu Glu Leu Gln Ala Ser
    210                 215                 220

Ser Ser Ser Asp Asn Ser Val Asn Glu Asp Arg Tyr Ala Glu Val Asp
225                 230                 235                 240

Val Ala Ala Ala Lys Ile Val Ser Gln Ala Asp Val Cys Ala Ala Cys
                245                 250                 255

Gly Ile Ala Glu Asn Asp Thr Gln Arg Met Leu Lys Pro Tyr Gln Leu
            260                 265                 270

Val Gly Val Asn Phe Met Leu Leu Leu His Arg Lys His Val Gly Gly
        275                 280                 285

Ala Val Ala Tyr Leu Ala Leu Leu Lys His Leu Asp Gly Asp Ala Gly
    290                 295                 300

Pro His Leu Leu Val Ala Pro Ala Ser Leu Leu Glu Asn Trp Gln Arg
305                 310                 315                 320

Glu Leu Lys Lys Trp Cys Pro Ala Phe Lys Val Glu Leu Tyr His Gly
                325                 330                 335

Ser Gly Arg Ala Ala Leu Asn Arg Arg Leu Gln Tyr Ala Ala Lys Ser
            340                 345                 350

Lys Gly Pro Ala Pro Phe Asn Val Met Leu Thr Cys Tyr Ser Leu Phe
        355                 360                 365
```

-continued

```
Glu Arg Gln Ser Ala Gln Thr Lys Asp Asp Arg Lys Phe Leu Lys Lys
    370                 375                 380
Trp Asn Trp Arg Cys Val Val Met Asp Glu Ala His Leu Leu Lys Asp
385                 390                 395                 400
Arg Ser Ser Phe Arg Ser Lys Lys Leu Arg Asp Ile Ala His Lys Ala
                405                 410                 415
Ile Gln Arg Leu Met Leu Thr Gly Thr Pro Leu Gln Asn Asp Leu Gln
                420                 425                 430
Glu Leu Trp Ser Leu Leu Glu Phe Met Met Pro Asp Val Phe Asn Thr
                435                 440                 445
Asn Gly Val Asp Leu Asp Gln Tyr Leu Gly Thr Arg Asn Asp Thr Ser
    450                 455                 460
Gly Ile Val Val Gln Asp Thr Asn Leu Met Thr Arg Ile Lys Gly Ile
465                 470                 475                 480
Leu Gly Pro Phe Val Leu Arg Arg Met Lys Thr Asp Val Met Arg Gln
                485                 490                 495
Leu Val Ser Lys Ile Gln Glu Val Glu Cys Val Glu Met Leu Asp Glu
                500                 505                 510
Gln Ser Met Ala Tyr Lys Lys Ala Val Asn Glu Tyr Arg Ala Leu Ala
                515                 520                 525
Glu Ser Ala Arg Ala Ala Lys Ala Ala Lys Lys Ser Ser Val Ser Val
    530                 535                 540
Val Asp Val Leu Pro Arg Arg Gln Val Thr Asn Ile Phe Thr Gln Leu
545                 550                 555                 560
Arg Lys Val Lys Lys Leu Ala Lys Lys Phe His Pro Leu Gly Val Phe
                565                 570                 575
Gly Tyr Glu Cys Asp Leu Gln Arg Val Glu Glu Leu Thr Ser Tyr
                580                 585                 590
Ser Asp Phe Asp Leu His Lys Leu Cys Ile Gln Tyr Gly Gly Ala Ala
                595                 600                 605
Gly Gly Gln Gly Lys Leu Asp Asp His Ala Leu Ala Ser Ala Lys
    610                 615                 620
Cys Gln Ala Leu Ala Arg Leu Leu Pro Lys Leu Gln Gln Gly Gly His
625                 630                 635                 640
Arg Thr Leu Ile Phe Ser Gln Trp Thr Ser Met Leu Asp Ile Leu Glu
                645                 650                 655
Trp Ala Leu Asp Val Met Gly Phe Ser Tyr Thr Arg Leu Asp Gly Ser
                660                 665                 670
Thr Gln Val Ser Glu Arg Gln Thr Leu Val Asp Glu Phe Asn Asn Asp
                675                 680                 685
Pro Ser Ile Phe Val Phe Leu Leu Ser Thr Arg Ala Gly Gly Gln Gly
    690                 695                 700
Leu Asn Leu Thr Gly Ala Asp Thr Val Ile Leu His Asp Leu Asp Phe
705                 710                 715                 720
Asn Pro Gln Met Asp Arg Gln Ala Glu Asp Arg Cys His Arg Ile Gly
                725                 730                 735
Gln Ser Lys Pro Val Thr Ile Tyr Arg Leu Val Thr Lys Asp Thr Val
                740                 745                 750
Asp Glu Ser Ile Tyr Lys Ile Ala Gln Gln Lys Leu Val Leu Asp Ala
                755                 760                 765
Ala Val Leu Glu Gly Lys Glu Ser Ser Asp Leu Asn Asp Gly Asp
    770                 775                 780
Ala Arg Thr Met Gly Glu Ile Leu Ser Ala Leu Leu Asp Val Pro Pro
```

```
                    785                 790                 795                 800
Thr

<210> SEQ ID NO 17
<211> LENGTH: 268
<212> TYPE: PRT
<213> ORGANISM: Physcomitrella patens

<400> SEQUENCE: 17

Met Ala Ser Lys Tyr Pro Arg Lys Cys Arg Glu His Ala Ser Pro Gly
1               5                   10                  15

Val Gly Gly Arg Glu Ser Thr His Arg Phe Asp Ser Arg Ser Gln Ser
            20                  25                  30

Tyr Ser Phe Ser Glu Lys Pro Tyr His Arg Arg Arg Asp Ala Phe
        35                  40                  45

Arg Asp Met Ile Ser Asp Leu Val His Gln Pro Ser Asp Thr Ala Val
50                  55                  60

Pro Gly Phe Arg Gly Val Arg Tyr Arg Gln Lys Leu Asn Lys Tyr Val
65                  70                  75                  80

Thr Glu Ile Arg Pro Thr Arg Cys Ser Lys Lys Ile Trp Leu Gly Thr
                85                  90                  95

Tyr Asp Thr Ala Glu Glu Ala Arg Ala Phe Asp Ile Gly Asn Leu
            100                 105                 110

Cys Cys Lys Lys Asn Leu Pro Leu Asn Phe Pro Asp Ser Thr Gln Met
        115                 120                 125

Leu Gln Arg Ile Ser Ser Lys Leu Thr Pro Glu Ala Gln Arg Lys Ala
130                 135                 140

Ile Ala Thr Leu Ala Lys Asp Val Val Arg Met Glu Asn Asp Arg Ser
145                 150                 155                 160

Lys Leu Gly Gly Gly Asn Leu Thr Thr Thr Glu Pro Val His Ser
                165                 170                 175

Glu Pro Ile Thr Gln His Leu Ala Ala Ala Glu Ile Arg Ala Val Thr
            180                 185                 190

Tyr Ile Glu Gln Pro Leu Glu Ile Val Tyr Gly Val Glu Glu Ser Ala
        195                 200                 205

Thr Ala Met Ser Val Thr Glu Ala Asn Ala Arg Asp Asn His Ser Trp
210                 215                 220

Ser Trp Asp Leu Gly Lys Val Ile Leu Asp Asp Glu Leu Ser Glu Ile
225                 230                 235                 240

Pro Asn Phe Val Gly Glu Leu Asp His Glu Ala Met Asp Phe Ser Ser
                245                 250                 255

His Gly Glu Val Tyr Tyr His His Tyr Asp Ser Gln
            260                 265

<210> SEQ ID NO 18
<211> LENGTH: 339
<212> TYPE: PRT
<213> ORGANISM: Physcomitrella patens

<400> SEQUENCE: 18

Met Val Val Pro Ser Leu Pro Ala Phe Gly Gly Gln Asn Ala Met Leu
1               5                   10                  15

Arg Arg Asn Ile Asp Asn Asn Thr Asp Thr Leu Ile Ser Leu Leu Gln
            20                  25                  30

Gly Ser Cys Ser Pro Arg Val Ser Met Gln Gln Val Pro Arg Ser Ser
        35                  40                  45
```

Glu Ser Leu Glu Asn Met Met Gly Ala Cys Gly Gln Lys Leu Pro Tyr
         50                  55                  60

Phe Ser Ser Phe Asp Gly Pro Ser Val Glu Glu Gln Glu Asp Val Asp
 65                  70                  75                  80

Glu Gly Ile Asp Glu Phe Ala His His Val Glu Lys Lys Arg Arg Leu
                 85                  90                  95

Ser Leu Glu Gln Val Arg Ser Leu Glu Arg Asn Phe Glu Val Glu Asn
            100                 105                 110

Lys Leu Glu Pro Glu Arg Lys Met Gln Leu Ala Lys Glu Leu Gly Leu
        115                 120                 125

Arg Pro Arg Gln Val Ala Val Trp Phe Gln Asn Arg Arg Ala Arg Trp
    130                 135                 140

Lys Thr Lys Gln Leu Glu His Asp Tyr Glu Thr Leu Lys Lys Ala Tyr
145                 150                 155                 160

Asp Arg Leu Lys Ala Asp Phe Glu Ala Val Thr Leu Asp Thr Asn Ala
                165                 170                 175

Leu Lys Ala Glu Val Ser Arg Leu Lys Gly Ile Ser Asn Asp Asp Val
            180                 185                 190

Lys Pro Ala Glu Phe Val Gln Gly Lys Cys Asp Thr Thr Ser His Pro
        195                 200                 205

Ala Ser Pro Ala Gln Ser Glu Arg Ser Asp Ile Val Ser Ser Arg Asn
    210                 215                 220

Arg Thr Thr Pro Thr Ile His Val Asp Pro Val Ala Pro Glu Glu Ala
225                 230                 235                 240

Gly Ala His Leu Thr Met Ser Ser Asp Ser Asn Ser Ser Glu Val Met
                245                 250                 255

Asp Ala Asp Ser Pro Arg Thr Ser His Thr Ser Ala Ser Arg Ser Thr
            260                 265                 270

Leu Ser Thr Ser Val Val Gln Pro Asp Glu Gly Leu Gly Val Ala Gln
        275                 280                 285

Tyr Pro His Phe Ser Pro Glu Asn Phe Val Gly Pro Asn Met Pro Glu
    290                 295                 300

Ile Cys Ala Asp Gln Ser Leu Ala Ser Gln Val Lys Leu Glu Glu Ile
305                 310                 315                 320

His Ser Phe Asn Pro Asp Gln Thr Phe Leu Leu Leu Pro Asn Trp Trp
                325                 330                 335

Asp Trp Ala

<210> SEQ ID NO 19
<211> LENGTH: 358
<212> TYPE: PRT
<213> ORGANISM: Physcomitrella patens

<400> SEQUENCE: 19

Met Pro Lys Pro Cys Asp Ala Cys His Val Ser Ser Ala Ala Val Phe
 1               5                  10                  15

Cys Arg Ala Asp Ala Ala Tyr Leu Cys Val Gly Cys Asp Gly Lys Val
                20                  25                  30

His Gly Ala Asn Lys Leu Ala Ser Arg His Glu Arg Val Trp Met Cys
            35                  40                  45

Glu Val Cys Glu Val Ala Pro Ala Val Val Thr Cys Lys Ala Asp Ala
        50                  55                  60

Ala Ser Leu Cys Val Ala Cys Asp Thr Asp Ile His Ser Ala Asn Pro
 65                  70                  75                  80

Leu Ala Gln Arg His Glu Arg Val Pro Val Thr Pro Leu Phe Glu Ser
                85                  90                  95

Ala Ser Pro Leu Arg Gly Pro Asp Phe Cys Val Leu Val Ser Glu Asn
            100                 105                 110

Gly Cys His Asp Leu Leu Lys Gly Cys Glu Asp Ala Ser Val Val Glu
        115                 120                 125

Ala Val Ser Trp Leu Leu Pro His Pro Lys Ile Ser Thr Asn Ser Ile
    130                 135                 140

Ile Arg Gly Ser Ala Ala Asp Glu Met Gly Ser Ser Pro Phe His
145                 150                 155                 160

Asp Arg Pro Phe Ser Pro Lys Pro Lys Lys Gln Lys Val Glu Leu Pro
                165                 170                 175

Ala Asp Ile Phe Ser Asp Val Asp Pro Phe Leu Asp Leu Asp Asp Ala
            180                 185                 190

Thr Val Thr Gly Ile Gln Pro Asp Ser Leu Val Pro Val His Met Pro
        195                 200                 205

Glu Cys Ser Glu Asp Thr Asp Ser Leu Ala His Ser Met Asp Pro Ser
    210                 215                 220

Phe Thr Lys Phe Pro Leu Ser Ala Lys Ser Gly Tyr Ser Tyr Gly Thr
225                 230                 235                 240

Ser Thr Leu Thr Gln Ser Ile Ser Cys Ser Ser Leu Asp Ala Ala Val
                245                 250                 255

Val Pro Asp Ser Ser Leu Ser Asp Ile Ser Thr Pro Tyr Leu Asp Ser
            260                 265                 270

Gln Ser Ser Gln Asp Met Ser Ala Arg Leu Pro His Gln Thr Gly Gly
        275                 280                 285

Pro Ile Asp Thr Val Asp Arg Glu Ala Arg Val Leu Arg Tyr Lys Glu
    290                 295                 300

Lys Arg Gln Lys Arg Lys Phe Glu Lys Thr Ile Arg Tyr Ala Ser Arg
305                 310                 315                 320

Lys Ala Tyr Ala Glu Ser Arg Pro Arg Ile Lys Gly Arg Phe Ala Lys
                325                 330                 335

Arg Thr Asp Ser Asp Met Glu Gln Phe Gly Ser Val Asp Ser Ser Phe
            340                 345                 350

Gly Val Val Pro Ser Phe
        355

<210> SEQ ID NO 20
<211> LENGTH: 343
<212> TYPE: PRT
<213> ORGANISM: Physcomitrella patens

<400> SEQUENCE: 20

Met Gly Asp Asn Ser Ala Ser Ala Arg Thr Asp Ser Ser Ser Asp Met
1               5                   10                  15

Asp Gly Asp Ala Lys Leu Asp Asp Gly Gln His Leu Ala Ser Gly Gly
            20                  25                  30

Gly Asn Ser Asn Asp Ser Ser Leu Glu Thr Gly Thr Lys Asn Gly Asp
        35                  40                  45

Ser Lys Val Leu Arg Arg Leu Ala Gln Asn Arg Glu Ala Ala Arg Lys
    50                  55                  60

Ser Arg Leu Arg Lys Lys Ala Tyr Val Gln Gln Leu Glu Ser Ser Arg
65                  70                  75                  80

Ile Lys Leu Asn Gln Leu Glu Gln Glu Leu Gln Arg Thr Arg Gln Gln

```
                85                  90                  95
Gln Gly Leu Tyr Leu Gly Pro Gly Ser Tyr Ser Asp Gln Asn Gly Gln
            100                 105                 110

Ser Gly Gly Val Gly Gly Ala Asn Ala Tyr Ser Ser Gly Ala Ala Ala
            115                 120                 125

Phe Asp Leu Glu Tyr Ala Arg Trp Val Glu Asp His Thr Arg Gln Met
            130                 135                 140

Ser Glu Leu Arg Val Ala Leu Gln Ala His Val Ala Asp Ala Asp Leu
145                 150                 155                 160

Arg Leu Leu Val Asp Gly Ser Met Ala His Tyr Asp Asp Leu Phe Arg
                165                 170                 175

Leu Lys Asp Ala Ala Lys Ala Asp Val Phe His Leu Val Ser Gly
            180                 185                 190

Met Trp Lys Thr Pro Ala Glu Arg Cys Phe Val Trp Ile Gly Gly Cys
            195                 200                 205

Arg Pro Ser Glu Leu Leu Lys Ile Leu Val Pro Gln Ile Glu Pro Leu
            210                 215                 220

Thr Glu Gln Gln Leu Leu Asn Ile Cys Asn Leu Gln Gln Ser Ser Gln
225                 230                 235                 240

Gln Gly Glu Glu Ala Leu Ser Gln Gly Met Glu Gln Leu Gln Gln Ser
                245                 250                 255

Leu Ala Glu Thr Leu Ser Ala Gly Ser Leu Gly Ser Ala Ala Asn Val
            260                 265                 270

Ala Asn Tyr Met Gly Gln Met Ala Val Ala Met Gly Gln Leu Gly Asn
            275                 280                 285

Leu Glu Gly Phe Val Arg Gln Ala Asp His Leu Arg Gln Gln Thr Leu
            290                 295                 300

Gln Gln Met His Arg Val Leu Thr Ile Arg Gln Val Ala Arg Gly Leu
305                 310                 315                 320

Leu Ala Met Gly Asp Tyr Phe Ala Arg Leu Arg Ala Leu Ser Ser Leu
                325                 330                 335

Trp Ser Ala Arg Pro Arg Glu
            340

<210> SEQ ID NO 21
<211> LENGTH: 214
<212> TYPE: PRT
<213> ORGANISM: Physcomitrella patens

<400> SEQUENCE: 21

Met Ser His Pro Gly Ala Val Met Pro Leu Gln Met His Tyr Pro Gln
1               5                   10                  15

Ala Gln Gln Gln Met Met Pro Gln Leu Gly Asp Gln Gln Met Gln Pro
            20                  25                  30

Gln Leu His Tyr Gln Gln Ile Gln Lys Gln Gln Leu Ser Gln Phe Trp
        35                  40                  45

Gln Gln Gln Met Gln Glu Met Glu Gln Val Asn Asp Phe Lys Thr His
    50                  55                  60

Gln Leu Pro Leu Ala Arg Ile Lys Lys Ile Met Lys Ser Asp Glu Asp
65                  70                  75                  80

Val Lys Met Ile Ala Ala Glu Ala Pro Val Leu Phe Ser Lys Ala Cys
                85                  90                  95

Glu Met Phe Ile Leu Glu Leu Thr Leu Arg Ser Trp Ile His Thr Glu
            100                 105                 110
```

```
Glu Asn Lys Arg Arg Thr Leu Gln Arg Asn Asp Ile Ala Gly Ala Ile
        115                 120                 125

Thr Arg Gly Asp Ile Phe Asp Phe Leu Val Asp Ile Val Pro Arg Asp
    130                 135                 140

Glu Leu Lys Glu Glu Asp Leu Gly Val Pro Trp Thr Gly Val Pro Gly
145                 150                 155                 160

Asp Gly Ser Val Pro Tyr Gly Gly Ile Phe Tyr Pro Pro Met Ala Gly
                165                 170                 175

Gln Gln Met His His Ser Met Gly Ala Pro Glu Met Met Val Gly Gln
            180                 185                 190

Pro Pro Asn Pro Gln Met Met Tyr Gln Pro Pro Gln Thr Ala Phe Val
        195                 200                 205

Pro Glu Gln Gln Gln Gln
    210

<210> SEQ ID NO 22
<211> LENGTH: 2838
<212> TYPE: DNA
<213> ORGANISM: Physcomitrella patens

<400> SEQUENCE: 22
gcccttatcc cgggcgatgg tgcgttcgag atcgtaaggt tgccgacgaa ggcgtaactt     60
ggaagtcctc tgtgtcccgg cgatgtccca atgttggccc gattttctgt ttttagcgag    120
ctgtgggcta gtttgtgggt atgatccggg gaatgagacg agatgtctgt ctgagtgaga    180
ccactctagg ggctgttgga ggatgaggag ggaagcgcag aagttggcca ttcttttcag    240
tgactggact ctgtgcgagt ggtcagcttt cgggagctgc tgttgcattg accggtgatt    300
cttttcgagat cgtagagaca gcagctggca agggttttgg gaggcttttc aaatgaaggg    360
cattcaagag ctttcagatg atgaagatta tattccgcct gtcaatgcat cgcgatattt    420
caacaggggc aaagcgctct caaagacatc atccaatcat gccaatggaa atggaaatcc    480
aaacggaacg agttttggag tttcaacttc ttcagcaagt gactctgaca agataagaa     540
atccgaagtt tcaggttctt tactaagcga ttctggcaag aatcaaaagt ccgttactga    600
attggattcg ttcgcattta accgcaagtc cagaattgcc aagcgaccta tcgagctact    660
cgaagacgag gaggacgtgg acgttggagc tgcaaaggtt gtagacattg agccgactaa    720
cggaaacaag aggcggagac ggtatcacac catcgaagac agtgacgatg aagagttgga    780
tgagaagaaa tcgtttggtg ataatctgac cccaggaacg gaaatcgatc aatgtgcagc    840
cgatgaatcc ttagcaaaaa ggttgcagga tttagagcac cgggcagttt ctggccgtaa    900
tcgcctggtt caaattttgt cagattccga tgaagaagaa gaggaagaag taaatcccat    960
aaccatcacc ctacaaaggt gtgaccagat tgcagcatca ttgcgagaag agctgcaggc   1020
cagcagttca agtgataact cggttaatga agatcgttat gcagaggttg atgtagcagc   1080
agcaaaaatt gtgagccagg cagatgtctg tgcagcttgt ggcattgccg agaatgatac   1140
acaacgaatg ctcaagccat atcagcttgt aggcgtcaat ttcatgctgc tacttcaccg   1200
caaacatgtt gggggtggca gttgcgtatc ttgcccttct gaaacatctt gatggagatg   1260
ctggtcctca tcttttagtt gcacctgctt ctcttttaga aaactggcaa agagaactca   1320
agaagtggtg tcctgcattt aaggtggagc tctatcatgg ctcaggaagg gcagctttaa   1380
acaggaggct tcagtatgct gcaaaatcta aagggcctgc acccttttaac gtgatgctga   1440
cgtgctactc ccttttgag aggcagagtg ctcagacaaa agatgaccgc aaattcctta   1500
```

```
agaaatggaa ttggcgctgt gtggttatgg acgaggctca tcttttgaag gacagaagca    1560
gctttcgcag caaaaagttg cgagatatag ctcacaaagc aattcaaaga ctgatgctga    1620
ctggtactcc actccagaac gatttgcagg agctatggtc acttctggag ttcatgatgc    1680
ctgatgtgtt caacacaaat ggcgttgatt tagatcaata tctgggaacc aggaacgata    1740
cctcagggat tgttgtgcag gatacgaact tgatgactcg gatcaaagga atactaggac    1800
cttttgtatt acgagaatg aaaactgatg ttatgcgcca gcttgtatca aagattcagg     1860
aggtggagtg tgtggagatg ctagacgagc aatcaatggc atataaaaaa gctgtgaatg    1920
agtatagagc ccttgctgag tccgcacgtg ccgctaaagc tgcaaagaaa tcctcagtta    1980
gcgtagtaga tgtccttcct cgtcgacaag tgaccaatat ctttactcaa ttgagaaagt    2040
caagaaattg gctaagaaat ttcatccatt aggagttttt ggatatgaat gcgatttgca    2100
gcgtgtggag gaagaattga ctagttacag cgattttgac ctccacaagt tgtgtattca    2160
atatggaggc gctgcgggag ggcaaggaaa gcttgatgat gatcatgcac tagcttctgc    2220
aaagtgccag gctttagcac gtctacttcc caagttacag caaggtggcc atcgcacatt    2280
gatattcagc cagtggacaa gcatgctgga tattttagaa tgggctcttg acgtcatggg    2340
tttttcttac actcgcctag atggaagcac tcaagtaagt gaacgccaaa ccctagtgga    2400
cgagttcaac aatgaccccta gcatatttgt gtttctcctg tctactcgag ctggaggtca    2460
aggtctaaat ttaacaggag cagacacagt cattttacat gatttggact caatcccca    2520 aatggatcga caggctgagg atcgctgtca tcggattggc cagtctaaac ctgttacgat    2580
ataccgactt gtaacaaaag atacggtcga tgaaagtata tacaagatag cccaacagaa    2640
gctggtcctc gatgcggcag ttcttgaagg aaaagagtca tcctctgatc ttaatgatgg    2700
tgatgctcgc acgatgggtg aaattctttc tgcattattg gatgttccac cgacatgatc    2760
ctggagtcca gaacacatt ttaatttatt ttcattatct ttatctggca ctgcgagaaa    2820
gctcgttaac gcaagggc                                                 2838
```

<210> SEQ ID NO 23
<211> LENGTH: 288
<212> TYPE: PRT
<213> ORGANISM: Physcomitrella patens

<400> SEQUENCE: 23

```
Met Lys Gly Ile Gln Glu Leu Ser Asp Asp Glu Asp Tyr Ile Pro Pro
 1               5                  10                  15

Val Asn Ala Ser Arg Tyr Phe Asn Arg Gly Lys Ala Leu Ser Lys Thr
            20                  25                  30

Ser Ser Asn His Ala Asn Gly Asn Gly Asn Pro Asn Gly Thr Ser Phe
        35                  40                  45

Gly Val Ser Thr Ser Ser Ala Ser Asp Ser Asp Lys Asp Lys Lys Ser
    50                  55                  60

Glu Val Ser Gly Ser Leu Leu Ser Asp Ser Gly Lys Asn Gln Lys Ser
65                  70                  75                  80

Val Thr Glu Leu Asp Ser Phe Ala Phe Asn Arg Lys Ser Arg Ile Ala
                85                  90                  95

Lys Arg Pro Ile Glu Leu Leu Glu Asp Glu Glu Asp Val Asp Val Gly
            100                 105                 110

Ala Ala Lys Val Val Asp Ile Glu Pro Thr Asn Gly Asn Lys Arg Arg
        115                 120                 125

Arg Arg Tyr His Thr Ile Glu Asp Ser Asp Asp Glu Glu Leu Asp Glu
```

```
            130                 135                 140
Lys Lys Ser Phe Gly Asp Asn Leu Thr Pro Gly Thr Glu Ile Asp Gln
145                 150                 155                 160

Cys Ala Ala Asp Glu Ser Leu Ala Lys Arg Leu Gln Asp Leu Glu His
                165                 170                 175

Arg Ala Val Ser Gly Arg Asn Arg Leu Val Gln Ile Leu Ser Asp Ser
            180                 185                 190

Asp Glu Glu Glu Glu Glu Val Asn Pro Ile Thr Ile Thr Leu Gln
        195                 200                 205

Arg Cys Asp Gln Ile Ala Ala Ser Leu Arg Glu Leu Gln Ala Ser
    210                 215                 220

Ser Ser Ser Asp Asn Ser Val Asn Glu Asp Arg Tyr Ala Glu Val Asp
225                 230                 235                 240

Val Ala Ala Lys Ile Val Ser Gln Ala Asp Val Cys Ala Ala Cys
                245                 250                 255

Gly Ile Ala Glu Asn Asp Thr Gln Arg Met Leu Lys Pro Tyr Gln Leu
                260                 265                 270

Val Gly Val Asn Phe Met Leu Leu Leu His Arg Lys His Val Gly Gly
            275                 280                 285
```

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggaaacag ctatgacc                                                    18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctaaagggaa caaaagctg                                                   19

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgtaaaacga cggccagt                                                    18

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcgatcctca gcctgtcgat ccatt                                        25

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccctgaggta tcgttcctgg ttccca                                       26

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atcccgggcg atggtgcgtt cgagatcgta agg                               33

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcgttaacga gctttctcgc agtgccagat aa                                32

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atcccgggct ctgcacccca gatgtcgcat cct                               33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgagctcta atgcattcac tgttgctgct gct                               33

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cctgtagggc cacccggagc tcact                                        25

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gagttaacgc agtggtcaca acgcagagta cgc               33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gcgatatcgc ttccatacct gcgccgaaga ctt               33

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gacccgggcc atgtgatatg gcttcaaagt at                32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gcgttaacga ctcactgaga gtcataatgg tg                32

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cgtagtcgcg ctcgagctgt ttggt                        25

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
atcccgggca cgagggcaag aggggataga gac               33

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcgttaacgc cgatggtgca actttggttg ac                                    32

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccgtgtcctc ggagcattct ggcat                                            25

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcccgggag gagggagttg gaatctagga gac                                   33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgagctcga ccttgctcga tggagactcc aat                                   33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atcccgggaa taggacggat ggccgacagt tac                                   33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgagctcac tcttacactc cgcggggttg gtt                                   33

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaatagatac gctgacacgc                                                    20

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgagctcac tcttacactc cgcggggttg gtt                                     33

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcgttaacgc cgatggtgca actttggttg ac                                      32

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcgagctcga ccttgctcga tggagactcc aat                                     33

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcgttaacga ctcactgaga gtcataatgg tg                                      32

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctagtaacat agatgacacc                                                    20

<210> SEQ ID NO 52

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
atcccgggcg atggtgcgtt cgagatcgta agg                                  33

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaatagatac gctgacacgc                                                 20

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgagctcta atgcattcac tgttgctgct gct                                  33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcgatatcgc ttccatacct gcgccgaaga ctt                                  33

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggagacggta tcacaccatc gaaga                                           25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgcacagaca tctgcctggc tcaca                                           25

<210> SEQ ID NO 58
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gatgatcgca gccgaagctc cagtg                                           25

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gggtgtgcca tggactggtg ttccag                                          26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggcagtctgt ggaggctgat acatca                                          26

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cctgatcctg tgaccccttt tgcca                                           25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gacatggacg gtgatgcgaa gttgg                                           25

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggcaacagc agggtctata ccttgg                                          26

<210> SEQ ID NO 64
<211> LENGTH: 26
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 64
gcatactcca ggtcaaatgc agcagc                                        26

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gggtcggcag cctccaatcc ataca                                         25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggcagggaat ctacgcatcg ctttg                                         25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgacgagatt ctctgcaaca tctgag                                        26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggagcttgga ctgcgacctc gtcaag                                        26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggtgtggctc gtgcgagggc tatcag                                        26

<210> SEQ ID NO 70
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 70
gtcatcgagg aatcgcacaa ctcct                                          25

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggttgacgtt ggattgcaca tggtgg                                         26

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tggatgtgcg aagtgtgcga ggttg                                          25

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcgctgcctc tgataataga gttgg                                          25

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtgcaggagt gcgtatccga gttcatc                                        27

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgtacggctg ttgcatcatc tgcatcg                                        27

<210> SEQ ID NO 76
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 76
cgccaagcgc gcaattaacc ctcact                                              26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcgtaatacg actcactata gggcga                                              26
```

TRANSCRIPTION FACTOR STRESS-RELATED PROTEINS AND METHODS OF USE IN PLANTS

CROSS-REFERENCE TO RELATED APPLICATIONS

This application is a continuation of U.S. patent application Ser. No. 11/564,883, filed Nov. 30, 2006, which is a divisional of U.S. patent application Ser. No. 10/168,846, filed Oct. 29, 2002 and now U.S. Pat. No. 7,164,057, which is an application filed pursuant to 35 U.S.C. § 371 that claims priority benefit of PCT application PCT/US00/34972, filed Dec. 22, 2000, and U.S. provisional application Ser. No. 60/171,745, filed Dec. 22, 1999, the entire contents of each of which are incorporated herein by reference.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

One model plant used in the study of stress tolerance is *Arabidopsis thaliana*. There are at least four different signal-transduction pathways leading to stress tolerance in the model plant *Arabidopsis thaliana*. These pathways are under the control of distinct transcription factors (Shinozaki et al., 2000 Curr. Op. Pl. Biol. 3:217-23). Regulators of genes, especially transcription factors, involved in these tolerance pathways are particularly suitable for engineering tolerance into plants because a single gene can activate a whole cascade of genes leading to the tolerant phenotype. Consequently, transcription factors are important targets in the quest to identify genes conferring stress tolerance to plants.

One transcription factor that has been identified in the prior art is the *Arabidopsis thaliana* transcription factor CBF (Jaglo-Ottosen et al., 1998 Science 280:104-6). Over-expression of this gene in *Arabidopsis* conferred drought tolerance to this plant (Kasuga et al., 1999 Nature Biotech. 17:287-91). However, CBF is the only example to date of a transcription factor able to confer drought tolerance to plants upon over-expression.

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated which leads to accumulation of new proteins in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique transcription factors capable of conferring stress tolerance to plants upon over-expression. Namely, described herein are the transcription factors: 1) CAAT-Box like Binding Factor-1 (CABF-1); 2) CABF-2 3) DNA Binding Factor-1 (DBF-1); 4) CRT/DRE Binding Factor (CBF-1); 5) Homeo Domain/Leucine Zipper (HDZ-1); 6) Zinc-Finger Factor (ZF-1) and 7) Leucine Zipper (LZ-1), all from *Physcomitrella patens*.

The present invention provides a transgenic plant transformed by a transcription factor stress-related protein (TFSRP) coding nucleic acid, wherein expression of the nucleic acid sequence in the plant results in increased tolerance to environmental stress as compared to a wild type variety of the plant. The invention provides that the TFSRP can be selected from one of the well known general classes of transcription factor proteins: 1) CAAT-Box like Binding Factor (CABF); 2) DNA Binding Factor (DBF); 3) Homeo Domain/Leucine Zipper (HDZ); 4) Zinc-Finger Factor (ZF); and 5) Leucine Zipper (LZ). The invention further provides specific examples of TFSRPs, and TFSRP coding nucleic acids, such as 1) CABF-1; 2) CABF-2; 3) DBF-1; 4) CRT/DRE Binding Factor (CBF-1); 5) HDZ-1; 6) ZF-1 and 7) LZ-1.

The invention provides in some embodiments that the TFSRP and coding nucleic acid are that found in members of the genus *Physcomitrella*. In another preferred embodiment, the nucleic acid and protein are from a *Physcomitrella patens* plant. The invention provides that the environmental stress can be salinity, drought, temperature, metal, chemical, pathogenic and oxidative stresses, or combinations thereof. In preferred embodiments, the environmental stress can be salinity, drought, and temperature, or combinations thereof.

The invention further provides a seed produced by a transgenic plant transformed by a TFSRP coding nucleic acid, wherein the plant is true breeding for increased tolerance to environmental stress as compared to a wild type variety of the plant. The invention further provides a seed produced by a transgenic plant expressing a TFSRP, wherein the plant is true breeding for increased tolerance to environmental stress as compared to a wild type variety of the plant.

The invention further provides an agricultural product produced by any of the above-described transgenic plants. The invention further provides an isolated TFSRP, wherein the TFSRP is as described below. The invention further provides an isolated TFSRP coding nucleic acid, wherein the TFSRP coding nucleic acid codes for a TFSRP as described below.

The invention further provides an isolated recombinant expression vector comprising a TFSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a TFSRP coding nucleic acid, wherein expression of the nucleic acid in the plant results in increased tolerance to environmental stress as compared to a wild type variety of the plant comprising: (a) transforming a plant cell with an expression vector comprising a TFSRP coding nucleic acid, and (b) generating from the plant cell a transgenic plant with an increased tolerance to environmental stress as compared to a wild type variety of the plant. In preferred embodiments, the TFSRP is as described below. In preferred embodiments, the TFSRP coding nucleic acid is as described below.

The invention further provides a method of increasing expression of a gene of interest within a host cell as compared to a wild type variety of the host cell, wherein the gene of interest is transcribed in response to a TFSRP, comprising: (a) transforming the host cell with an expression vector comprising a TFSRP coding nucleic acid, and (b) expressing the TFSRP within the host cell, thereby increasing the expression of the gene transcribed in response to the TFSRP as compared to a wild type variety of the host cell. In preferred embodiments, the TFSRP is as described below. In preferred embodiments, the TFSRP coding nucleic acid is as described below.

The present invention further provides a method of identifying a novel TFSRP, comprising (a) raising a specific antibody response to a TFSRP, or fragment thereof, as described above; (b) screening putative TFSRP material with the antibody, wherein specific binding of the antibody to the material indicates the presence of a potentially novel TFSRP; and (c) analyzing the bound material in comparison to known TFSRP to determine its novelty.

BRIEF DESCRIPTION OF THE DRAWINGS

FIGS. 1(A-G) show the partial cDNA sequences of CABF-1 (SEQ ID NO:1), DBF-1 (SEQ ID NO:2), CBF-1 (SEQ ID NO:3), HDZ-1 (SEQ ID NO:4), ZF-1 (SEQ ID NO:5), LZ-1 (SEQ ID NO:6) and CABF-2 (SEQ ID NO:7) from *Physcomitrella patens*.

FIGS. 2(A-H) show the full-length cDNA sequences of CABF-1 (SEQ ID NO:8), DBF-1 (SEQ ID NO:9), DBF-1 variant (SEQ ID NO:22), CBF-1 (SEQ ID NO:10), HDZ-1 (SEQ ID NO:11), ZF-1 (SEQ ID NO:12), LZ-1 (SEQ ID NO:13) and CABF-2 (SEQ ID NO: 14) from *Physcomitrella patens*.

FIGS. 3(A-H) show the deduced amino acid sequences of CABF-1 (SEQ ID NO:15), DBF-1 (SEQ ID NO:16), DBF-1 variant (SEQ ID NO:23), CBF-1 (SEQ ID NO:17), HDZ-1 (SEQ ID NO:18), ZF-12 (SEQ ID NO:19), LZ-1 (SEQ ID NO:20) and CABF-2 (SEQ ID NO: 21) from *Physcomitrella patens*.

FIG. 4 shows a diagram of the plant expression vector pGMSG containing the super promoter driving the expression of SEQ ID NOs: 8, 9, 10, 11, 12, 13, and 14 ("Desired Gene"). The components are: aacCI gentamycin resistance gene (Hajdukiewicz et al., 1994 Plant Molecular Biology 25:989-94), NOS promoter (Becker et al., 1992 Plant Molecular Biology 20:1195-7), g7T terminator (Becker et al., 1992), NOSpA terminator (Jefferson et al., 1987 EMBO J. 6:3901-7).

DETAILED DESCRIPTION OF THE INVENTION

Figure 5:
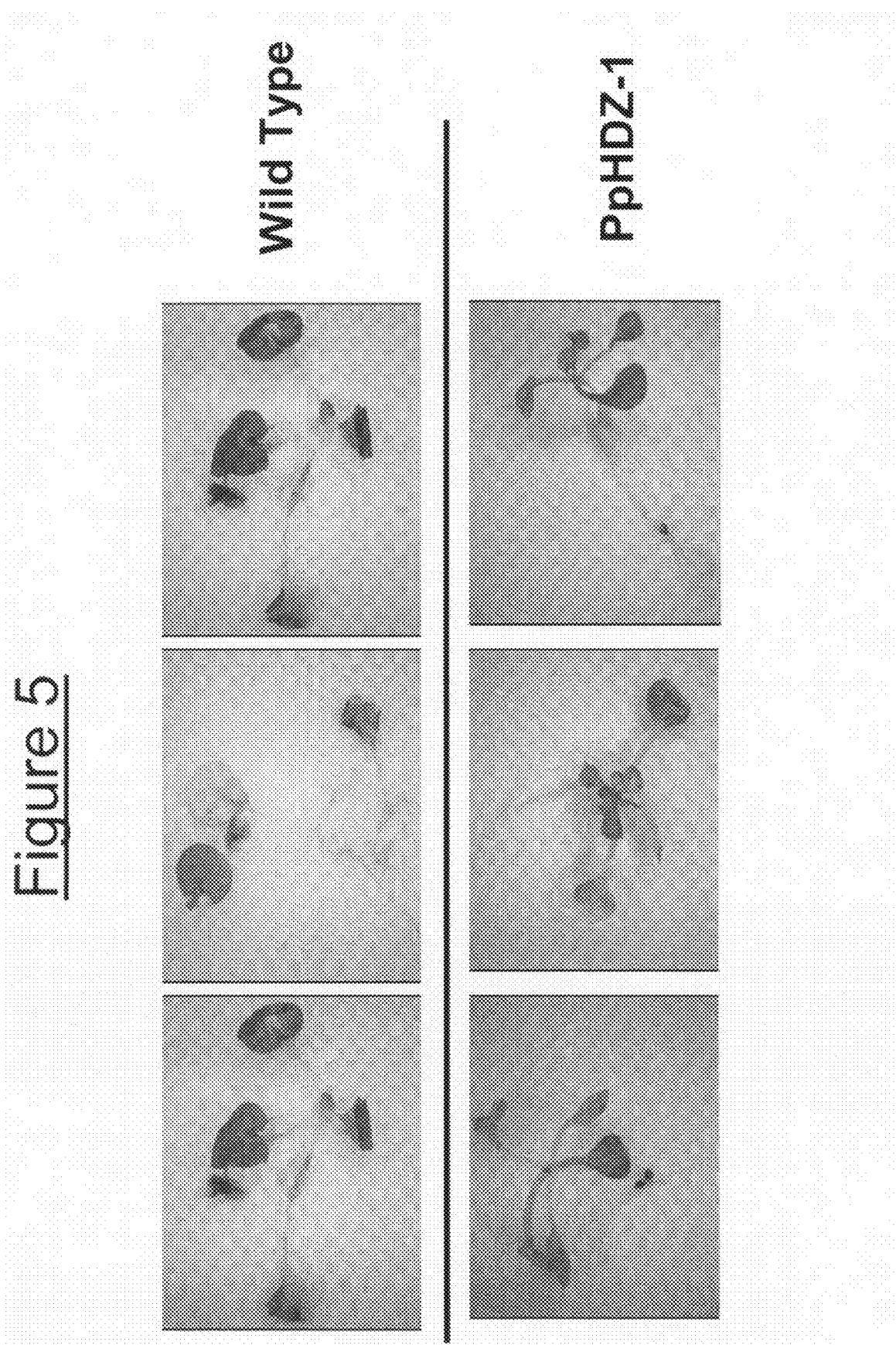
FIG. 5 shows the results of a drought stress test with over-expressing HDZ-1 from *Physcomitrella patens* in transgenic plants and wild-type *Arabidopsis* lines. The transgenic lines display a tolerant phenotype. Individual transformant lines are shown.
Figure 6:
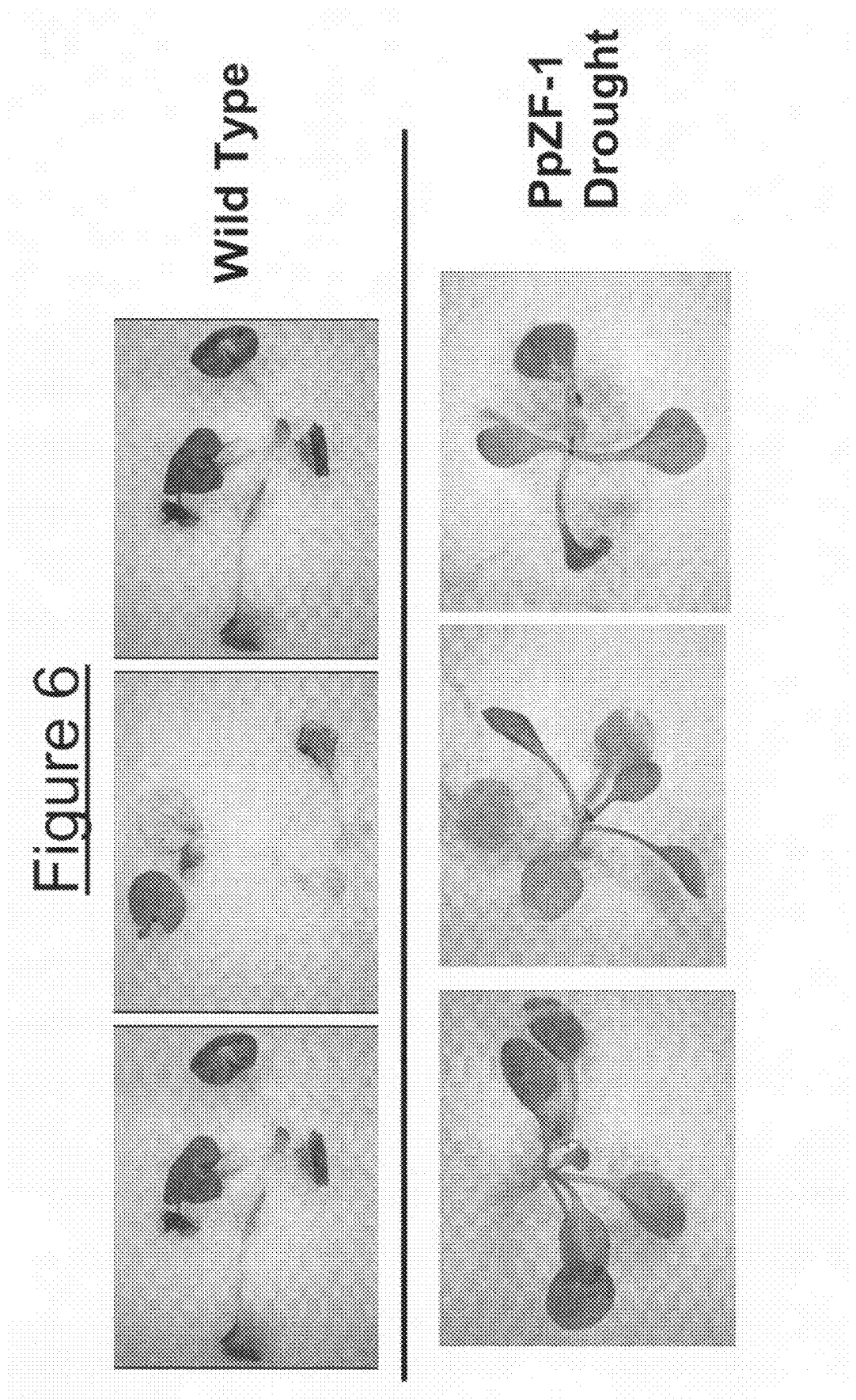
FIG. 6 shows the results of a drought stress test with over-expressing ZF-1 from *Physcomitrella patens* in transgenic plants and wild-type *Arabidopsis* lines. The transgenic lines display a tolerant phenotype. Individual transformant lines are shown.
Figure 7:
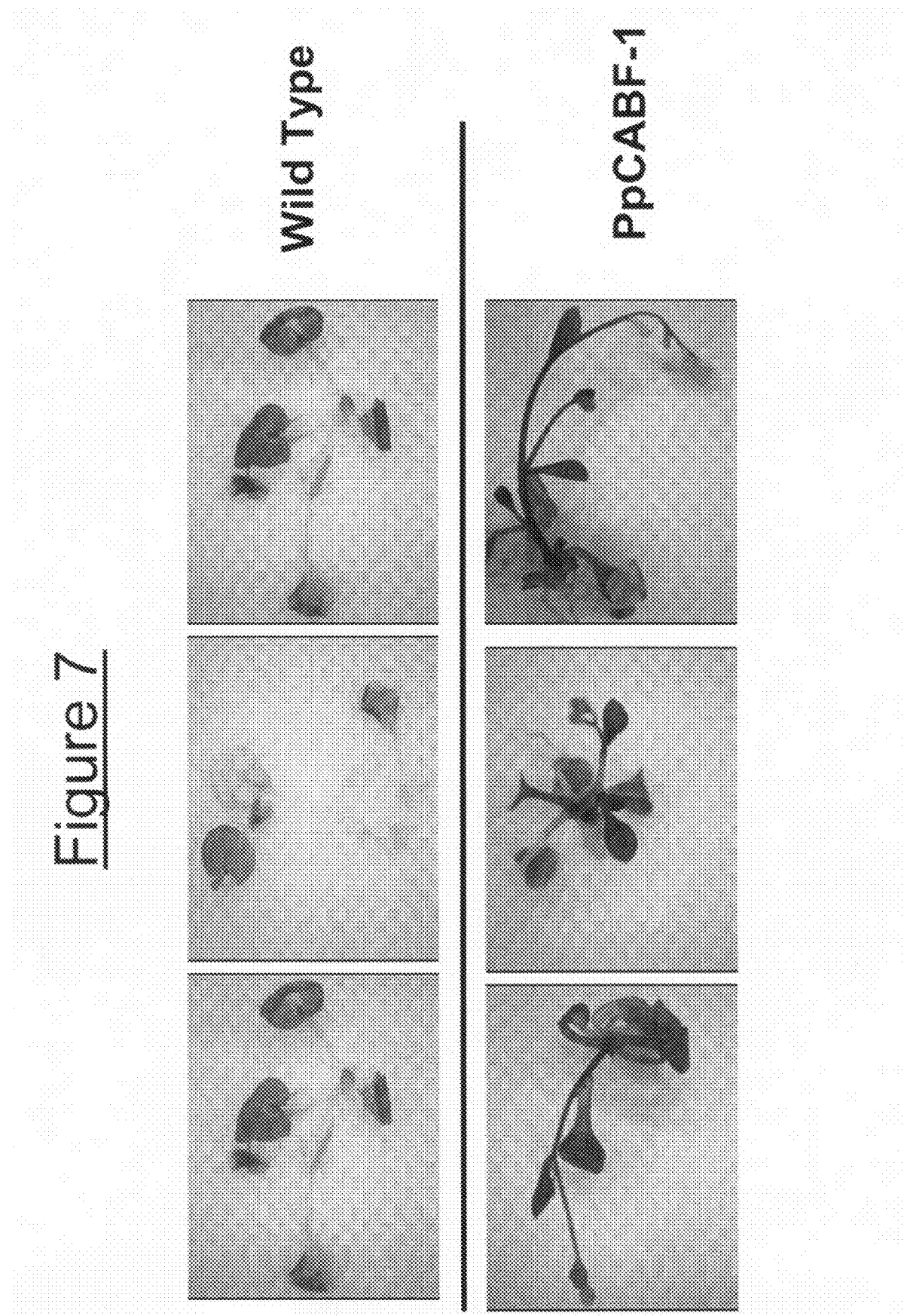
FIG. 7 shows the results of a drought stress test with over-expressing CABF-1 from *Physcomitrella patens* in transgenic plants and wild-type *Arabidopsis* lines. The transgenic lines display a tolerant phenotype. Individual transformant lines are shown.
Figure 8:
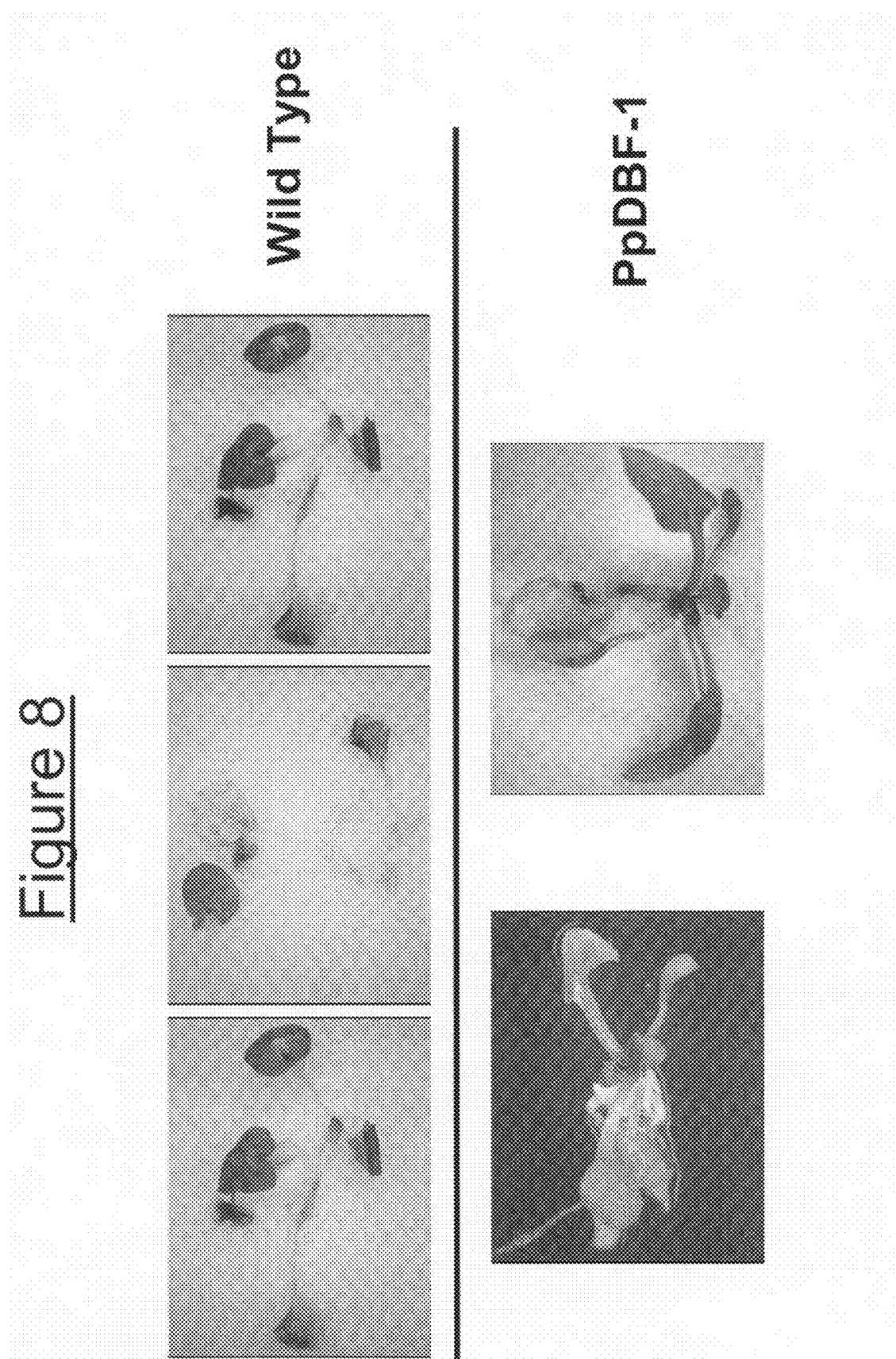
FIG. 8 shows the results of a drought stress test with over-expressing DBF-1 from *Physcomitrella patens* in transgenic plants and wild-type *Arabidopsis* lines. The transgenic lines display a tolerant phenotype. Individual transformant lines are shown.
Figure 9:
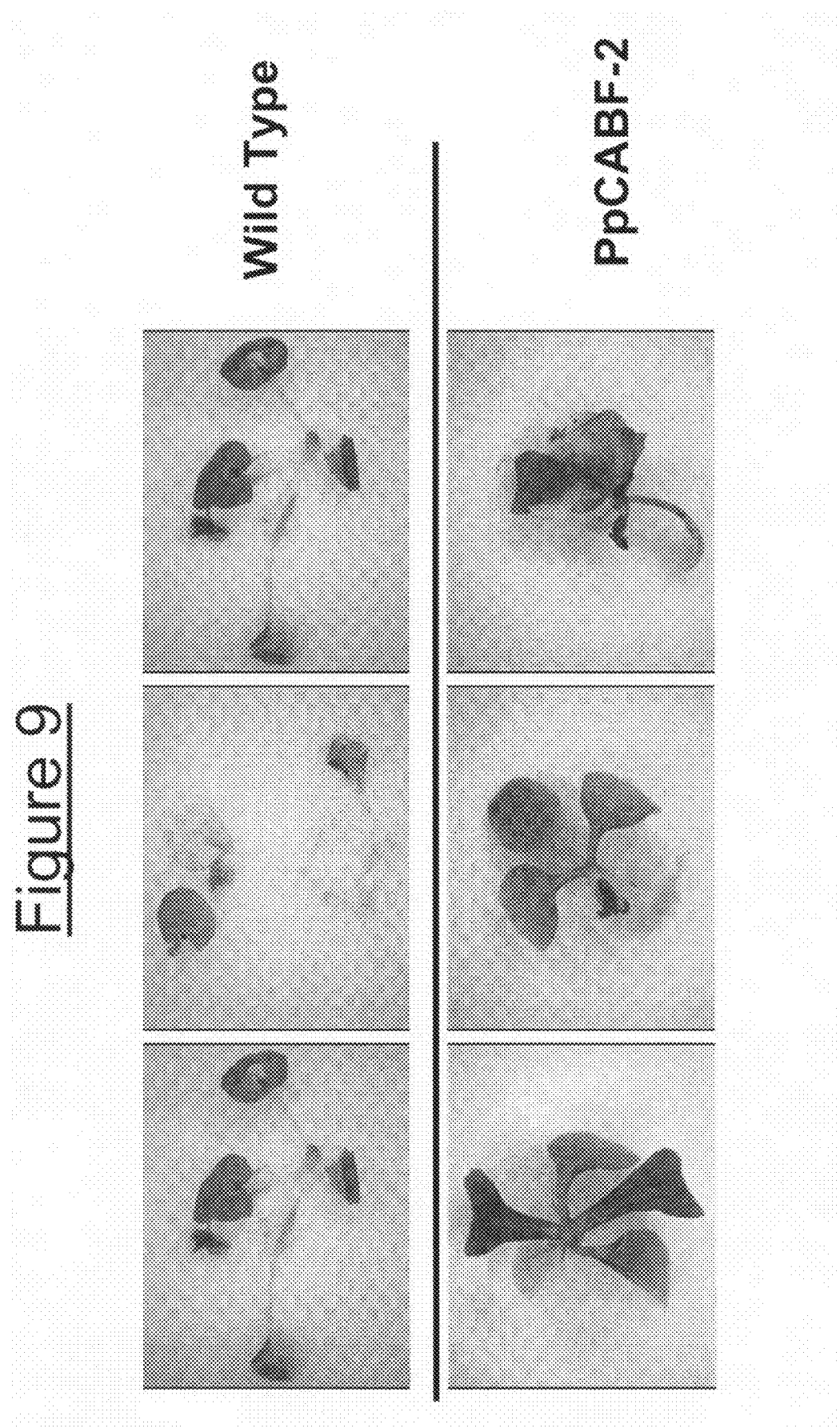
FIG. 9 shows the results of a drought stress test with over-expressing CABF-2 from *Physcomitrella patens* in transgenic plants and wild-type *Arabidopsis* lines. The transgenic lines display a tolerant phenotype. Individual transformant lines are shown.
Figure 10:
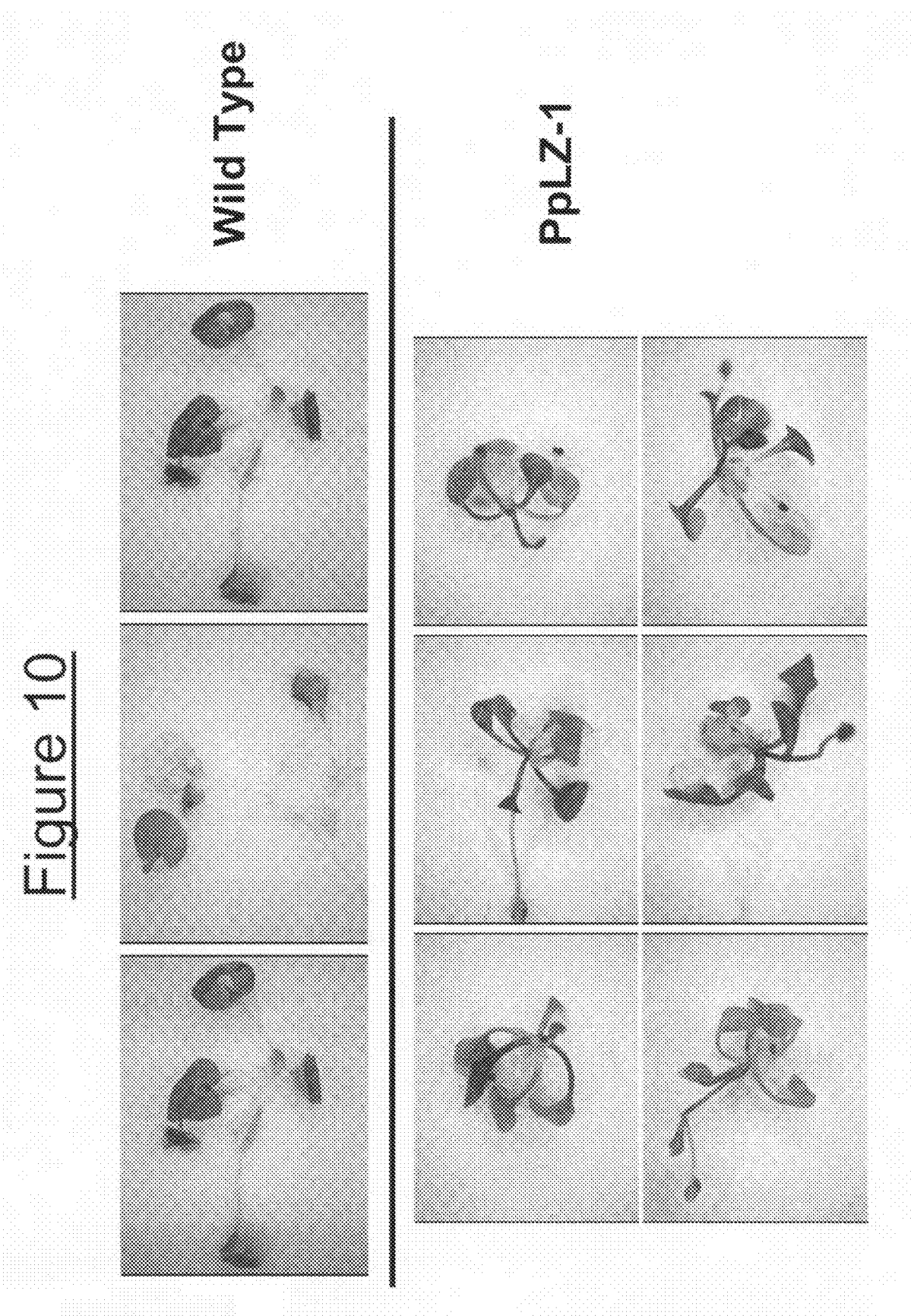
FIG. 10 shows the results of a drought stress test with over-expressing LZ-1 from *Physcomitrella patens* in transgenic plants and wild-type *Arabidopsis* lines. The transgenic lines display a tolerant phenotype. Individual transformant lines are shown.
Figure 11:
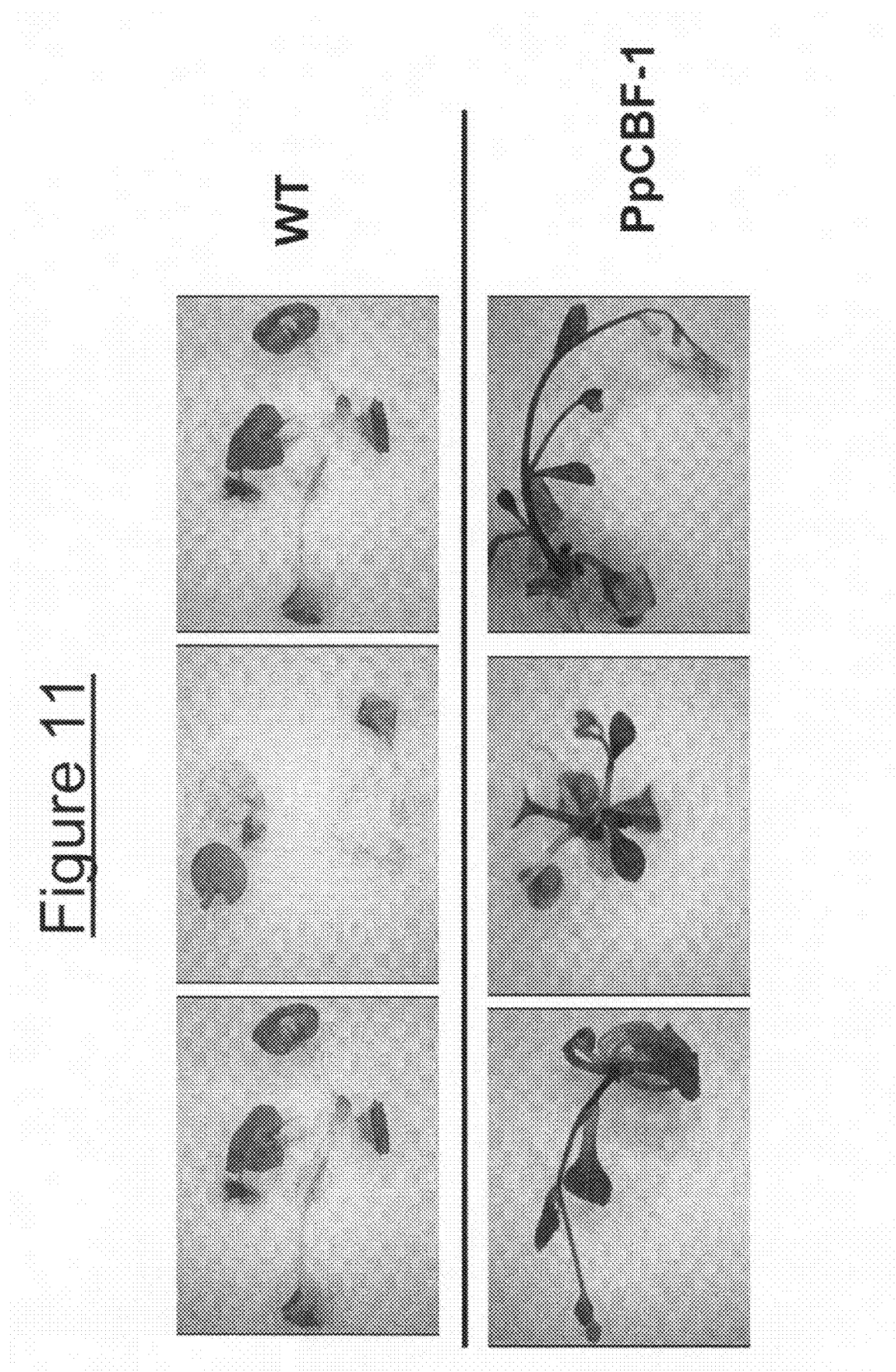
FIG. 11 shows the results of a drought stress test with over-expressing CBF-1 from *Physcomitrella patens* in transgenic plants and wild-type *Arabidopsis* lines. The transgenic lines display a tolerant phenotype. Individual transformant lines are shown.
Figure 12:
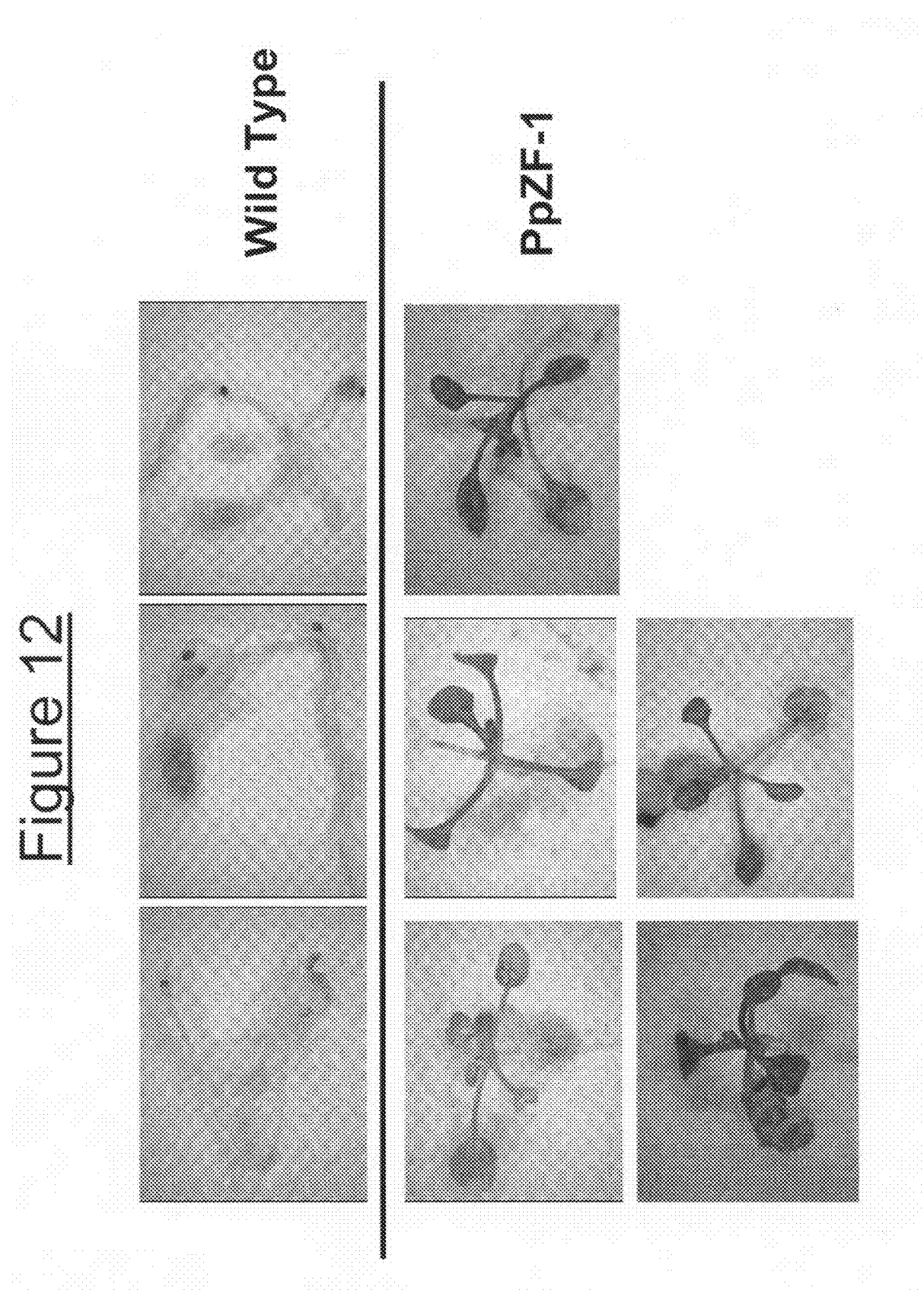
FIG. 12 shows the results of a salt stress test with over-expressing ZF-1 from *Physcomitrella patens* in transgenic plants and wild-type *Arabidopsis* lines. The transgenic lines display a tolerant phenotype. Individual transformant lines are shown.
Figure 13:
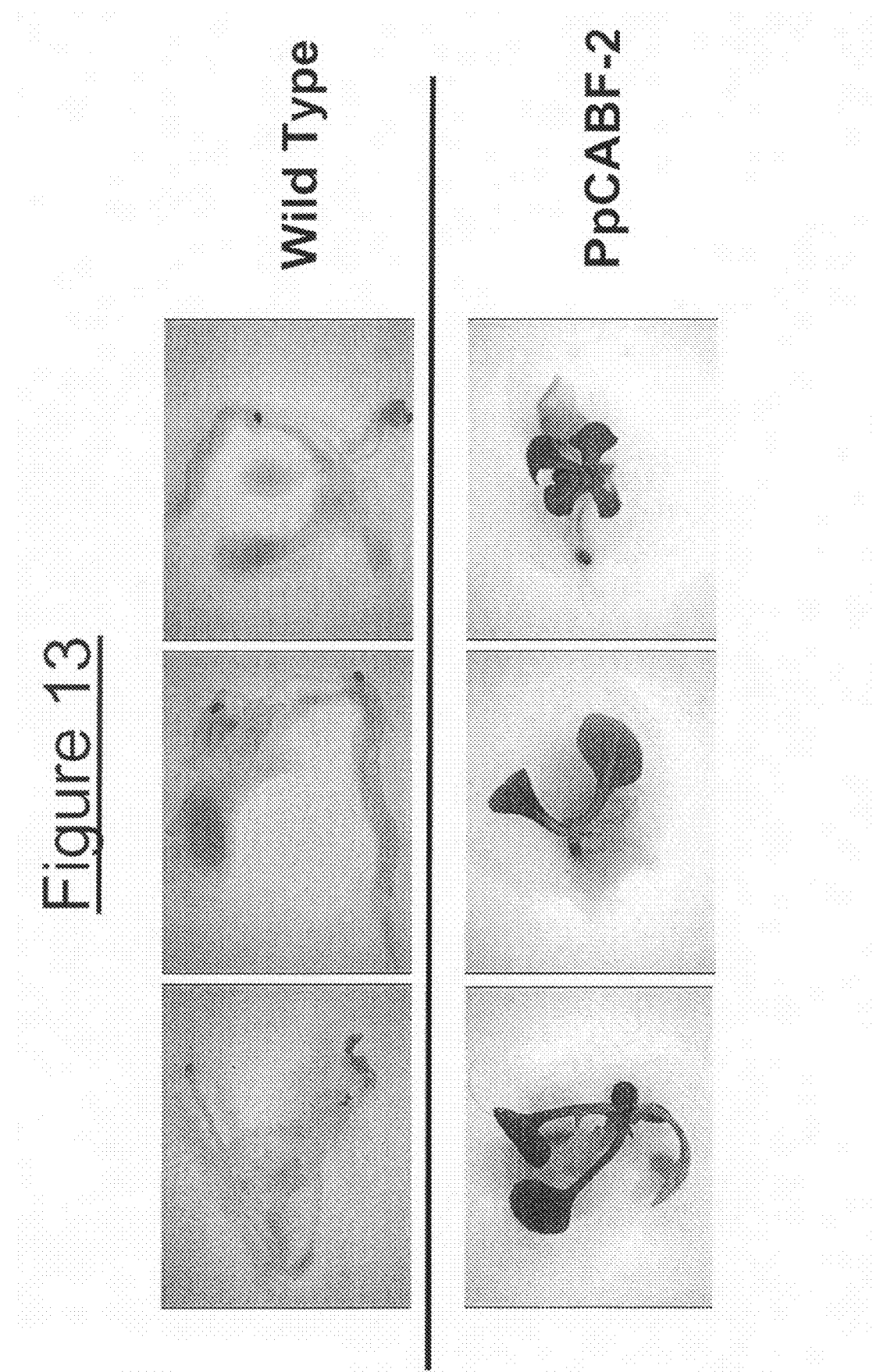
FIG. 13 shows the results of a salt stress test with over-expressing CABF-2 from *Physcomitrella patens* in transgenic plants and wild-type *Arabidopsis* lines. The transgenic lines display a tolerant phenotype. Individual transformant lines are shown.
Figure 14:
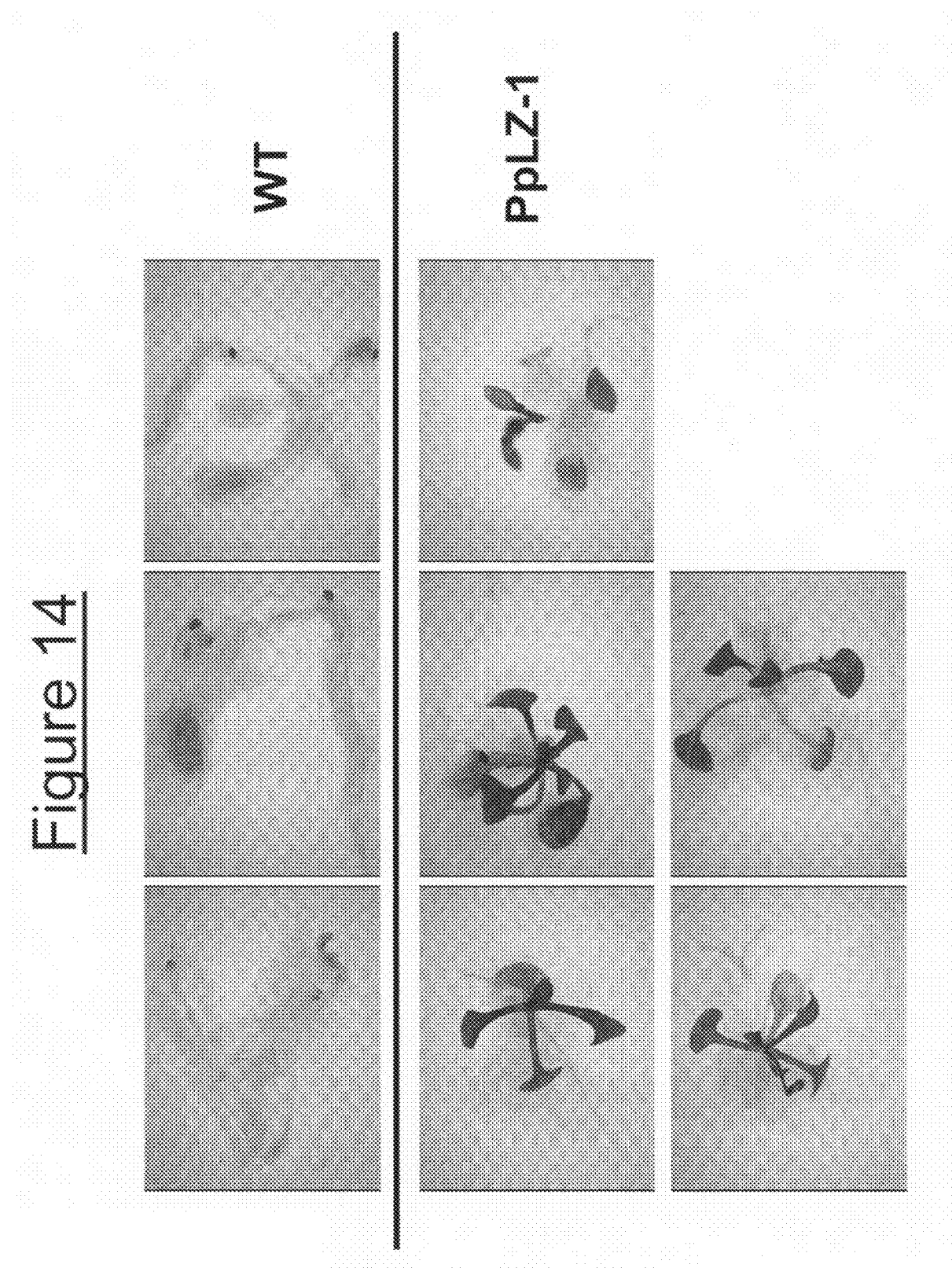
FIG. 14 shows the results of a salt stress test with over-expressing LZ-1 from *Physcomitrella patens* in transgenic plants and wild-type *Arabidopsis* lines. The transgenic lines display a tolerant phenotype. Individual transformant lines are shown.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Transcription Factor Stress-related Proteins" (TFSRPs), in no way limits the functionality of those sequences.

The present invention provides a transgenic plant transformed by a TFSRP coding nucleic acid, wherein expression of the nucleic acid sequence in the plant results in increased tolerance to environmental stress as compared to a wild type variety of the plant. The invention further provides a seed produced by a transgenic plant transformed by a TFSRP coding nucleic acid, wherein the seed contains the TFSRP coding nucleic acid, and wherein the plant is true breeding for increased tolerance to environmental stress as compared to a wild type variety of the plant. The invention further provides a seed produced by a transgenic plant expressing a TFSRP, wherein the seed contains the TFSRP, and wherein the plant is true breeding for increased tolerance to environmental stress as compared to a wild type variety of the plant. The invention further provides an agricultural product produced by any of the above- or below-described transgenic plants. As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of a single DNA sequence introduced into a plant variety.

The invention further provides an isolated TFSRP. The invention provides that the TFSRP can be selected from one of the well known general classes of transcription factor proteins, such as: 1) CAAT-Box like Binding Factor (CABF); 2) DNA Binding Factor (DBF); 3) Homeo Domain/Leucine Zipper (HDZ); 4) Zinc-Finger Factor (ZF); and 5) Leucine Zipper (LZ). It is a novel finding of the present invention that these classes of transcription factors are involved in stress tolerance in plants and that expression of a member of one of these protein classes in a plant can increase that plant's tolerance to stress. In further preferred embodiments, the TFSRP is selected from 1) a CAAT-Box like Binding Factor-1 (CABF-1) as defined in SEQ ID NO:15; 2) a CABF-2 as defined in SEQ ID NO:21; 3) a DNA Binding Factor-1 (DBF-1) as defined in SEQ ID NO:16; 4) a CRT/DRE Binding Factor (CBF-1) as defined in SEQ ID NO:17; 5) a Homeo Domain/Leucine Zipper (HDZ-1) as defined in SEQ ID NO:18; 6) a Zinc-Finger Factor (ZF-1) as defined in SEQ ID NO:19; 7) a Leucine Zipper (LZ-1) as defined in SEQ ID NO:20; 8) a DNA. Binding Factor-1 variant (DBF-1v) as defined in SEQ ID NO:23 and homologues thereof. Homologues of the amino acid sequences are defined below.

The invention further provides an isolated TFSRP coding nucleic acid. The present invention includes TFSRP coding nucleic acids that encode TFSRPs as described herein. In preferred embodiments, the TFSRP coding nucleic acid is selected from 1) a CAAT-Box like Binding Factor-1 (CABF-1) as defined in SEQ ID NO:1; 2) a CABF-2 as defined in SEQ ID NO:7; 3) a DNA Binding Factor-1 (DBF-1) as defined in SEQ ID NO:2; 4) a CRT/DRE Binding Factor (CBF-1) as defined in SEQ ID NO:3; 5) a Homeo Domain/Leucine Zipper (HDZ-1) as defined in SEQ ID NO:4; 6) a Zinc-Finger Factor (ZF-1) as defined in SEQ ID NO:5; 7) a Leucine Zipper (LZ-1) as defined in SEQ ID NO:6; a DNA Binding Factor-1 variant (DBF-1v) as defined in SEQ ID NO:22 and homologues thereof. Homologues of the nucleotide sequences are defined below. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, and temperature, or combinations thereof, and in particular, can be high salinity, low water content and low temperature. It is also to be understood that as used in the specification and in the claims, "a" or "an" can mean one or more, depending upon the context in which it is used. Thus, for example, reference to "a cell" can mean that at least one cell can be utilized.

In accordance with the purposes of this invention, as embodied and broadly described herein, this invention, in one aspect, provides an isolated nucleic acid from a moss encoding a Stress-related Protein (SRP), or a portion thereof. In particular, the present invention provides nucleic acids encoding TFSRPs including the nucleic acid sequences shown in SEQ ID NO:8, SEQ ID NO:9, SEQ ID NO:10, SEQ ID NO:11, SEQ ID NO:12, SEQ ID NO:13, SEQ ID NO:14 and SEQ ID NO:22. The present invention also provides amino acid sequences of TFSRPs including the amino acid sequences shown in SEQ ID NO:15, SEQ ID NO:16, SEQ ID NO:17, SEQ ID NO:18, SEQ ID NO:19, SEQ ID NO:20, SEQ ID NO:21 and SEQ ID NO:23.

The present invention describes for the first time the predicted *P. patens* proteins CABF-1 (SEQ ID NO:15) and CABF-2 (SEQ ID NO:21) that are homologous to CAAT-Box Binding Factors. (Homology to other proteins is shown in Tables 4 and 6, respectively). The amino acid sequence of CABF-1 (SEQ ID NO:15) is similar to the domain "B" of other CAAT-Box Binding Factors (Johnson and McKnight, 1989 Ann. Rev. Biochem. 58:799-840). In general, CABFs are members of multi-component transcription activation complex. They are involved as general transcriptional regulators as well as in the activation of specific genes. The particular combination of the different CABFs and other subunits determines which genes are targeted and activated. The present invention also describes for the first time that CABF proteins such as CABF-1 (SEQ ID NO:15), are useful for increasing stress tolerance in plants. Particularly, the present invention demonstrates that CABF-1 is important for the activation of drought-related genes upon expression in *Arabidopsis thaliana*.

Another novel predicted *P. patens* protein described herein is DBF-1 (SEQ ID NO:16), which is homologous to several eukaryotic proteins implicated in gene regulation (transcription factors) and/or chromatin structure modulation (i.e. helicases), for example the gene Etl-1 from mouse (Soininen et al. 1992 Mech Dev. 39:111-23). (Homology to other proteins is shown in Table 5). The identity between DBF-1 (SEQ ID NO:16) and Etl-1 is greater in the C-terminus of the later; a region where the identity with other known transcription factors and/or helicases (chromatin-structure changing proteins) is the greatest. Hence, DBF-1 (SEQ ID NO:16) contains the functional domains of these other proteins, a fact that strengthens the hypothesis that this protein functions in vivo. Over-expression of DBF-1 in *Arabidopsis thaliana* permits for the constitutive, strong expression of drought-related genes in this plant, and results in a drought tolerant plant. Interestingly, there seem to be two specifically observed variant forms of protein DBF-1, SEQ ID NO:16 and SEQ ID NO:23, in *P. patens* and both variants are equally efficient in conferring stress tolerance to a transgenic plant.

Another novel predicted *P. patens* protein described herein is CBF-1 (SEQ ID NO:17), which is a homologue of the *Arabidopsis thaliana* transcription factor CBF-1. (Homology to other proteins is shown in Table 8). As mentioned before, expression of CBF-1 leads to stress-tolerant plants. Because CBF-1 (SEQ ID NO:17) originates from a stress-tolerant plant, *Physcomitrella patens*, it is conceivable that this gene confers a higher level of stress tolerance to other plants than the *Arabidopsis* homologue.

Yet another discovery of the present invention is that a group of Homeodomain/Leucine Zipper transcription factors confer increased stress tolerance to plants. Also described is a novel predicted *P. patents* protein designated HDZ-1 (SEQ ID NO:18), which is a homologue of HD-Z transcription factors found in plants. (Homology to other proteins is shown in Table 2). Homeodomain (HD) transcription factors have been well characterized in animals as being involved in organ formation. In plants, HD proteins seem to contain, in many cases, an adjacent Leucine Zipper domain (HD-Z proteins). Most of these genes are specifically expressed in meristems; consistent with their role in morphology determination (Tomero et al., 1996 Pl. J. 9:639-48). However, HD-Z proteins have also been implicated in non-developmental processes. Expression of HDZ-1 (SEQ ID NO:18) in *Arabidopsis thaliana* constitutively activates genes involved in drought tolerance, resulting in drought-tolerant plants.

Another novel predicted *P. patens* protein described herein is ZF-1 (SEQ ID NO:19), which shows sequence similarity to the Zinc-Finger class of transcription factors. (Homology to other proteins is shown in Table 3). Zinc-finger transcription factors share a specific secondary structure where a zinc molecule is sequestered via its interaction with cysteine or histidine amino acid residues. Through these "fingers," the proteins interact with their specific DNA targets. After binding, they regulate transcription of the target genes. Zinc-finger factors are associated in yeast with the regulation of multiple genes, e.g., genes involved in general metabolism. In plants, a zinc-finger protein, CONSTANS, is responsible for determining flowering time (Putterill et al., 1995 Cell 80:847-57). The present invention also describes for the first time that ZF transcription factors are useful for increasing stress tolerance in plants. Particularly, the present invention demonstrates that ZF-1 from *P. patens* is important for the activation of drought-related genes upon expression in *Arabidopsis thaliana*.

Another novel predicted protein described herein is LZ-1 (SEQ ID NO:20), which shares amino acid sequence similarity with other Leucine-Zipper transcription factors (Ehrlich et al., 1992 Gene 15: 169-78). (Homology to other proteins is shown in Table 7). Leucine-Zipper transcription factors are also involved in numerous other processes in the life cycle of a plant; ranging from light-specific gene expression to seed-specific gene induction. The present invention described for the first time that LZ transcription factors confer stress tolerance to transgenic plants, and in particular that LZ-1 from *P. patens* confers stress tolerance to *Arabidopsis thaliana* plants.

One aspect of the invention pertains to isolated nucleic acid molecules that encode TFSRP polypeptides or biologically active portions thereof, as well as nucleic acid fragments sufficient for use as hybridization probes or primers for the identification or amplification of TFSRP-encoding nucleic acid (e.g., TFSRP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated TFSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:8, SEQ ID NO:9, SEQ ID NO:10, SEQ ID NO:1, SEQ ID NO:12, SEQ ID NO:13, SEQ ID NO:14 or SEQ ID NO:22, or a portion thereof, can be isolated using standard molecular biology techniques and the sequence information provided herein. For example, a *P. patens* TFSRP cDNA can be isolated from a *P. patens* library using all or portion of one of the sequences of SEQ ID NO:1, SEQ ID NO:2, SEQ ID NO:3, SEQ ID NO:4, SEQ ID NO:5, SEQ ID NO:6, and SEQ ID NO:7 as a hybridization probe and standard hybridization techniques (e.g., as described in Sambrook et al., 1989 *Molecular Cloning: A Laboratory Manual. 2nd, ed., Cold Spring Harbor Laboratory*, Cold Spring Harbor Laboratory Press, Cold Spring Harbor, N.Y.). Moreover, a nucleic acid molecule encompassing all or a portion of one of the sequences of SEQ ID NO:1, SEQ ID NO:2, SEQ ID NO:3, SEQ ID NO:4, SEQ ID NO:5, SEQ ID NO:6, and SEQ ID NO:7 can be isolated by the polymerase chain reaction using oligonucleotide primers designed based upon this sequence (e.g., a nucleic acid molecule encompassing all or a portion of one of the sequences of SEQ ID NO:1, SEQ ID NO:2, SEQ ID NO:3, SEQ ID NO:4, SEQ ID NO:5, SEQ ID NO:6, and SEQ ID NO:7 can be isolated by the polymerase chain reaction using oligonucleotide primers designed based upon this same sequence of SEQ ID NO:1, SEQ ID NO:2, SEQ ID NO:3, SEQ ID NO:4, SEQ ID NO:5, SEQ ID NO:6, or SEQ ID NO:7). For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4, SEQ ID NO:5, SEQ ID NO:6 or SEQ ID NO:7. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a TFSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22. The sequences of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 correspond to the *Physcomitrella patens* TFSRP cDNAs of the invention. These cDNAs comprise sequences encoding TFSRPs (i.e., the "coding region", indicated in Table 1), as well as 5' untranslated sequences and 3' untranslated sequences. It is to be understood that SEQ ID NO:8, SEQ ID NO:9, SEQ ID NO:10, SEQ ID NO:11, SEQ ID NO:12, SEQ ID NO:13, SEQ ID NO:14 or SEQ ID NO:22 comprise both coding regions and 5' and 3' untranslated regions. Alternatively, the nucleic acid molecule can comprise only the coding region of any of the sequences in SEQ ID NO:8, SEQ ID NO:9, SEQ ID NO:10, SEQ ID NO:11, SEQ ID NO:12, SEQ ID NO:13, SEQ ID NO:14 or SEQ ID NO:22 or can contain whole genomic fragments isolated from genomic DNA. A coding region of these sequences is indicated as "ORF position". It is to be understood that the In another preferred embodiment, an isolated nucleic acid molecule of the invention comprises a nucleic acid molecule which is a complement of one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22, or a portion thereof. A nucleic acid molecule which is complementary to one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22 is one which is sufficiently complementary to one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22 such that it can hybridize to one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22, thereby forming a stable duplex.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22, or a portion thereof. In an additional preferred embodiment, an isolated nucleic acid molecule of the invention comprises a nucleotide sequence which hybridizes, e.g., hybridizes under stringent conditions, to one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in SEQ ID NO:8, SEQ ID NO:9, SEQ ID NO:10, SEQ ID NO:11, SEQ ID NO:12, SEQ ID NO:13, SEQ ID NO:14 and SEQ ID NO:22, for example a fragment which can be used as a probe or primer or a fragment encoding a biologically active portion of a TFSRP. The nucleotide sequences determined from the cloning of the TFSRP genes from *P. patens* allows for the generation of probes and primers designed for use in identifying and/or cloning TFSRP homologues in other cell types and organisms, as well as TFSRP homologues from other mosses or related species. Therefore this invention also provides compounds comprising the nucleic acid molecules disclosed herein, or fragments thereof. These compounds include the nucleic acid molecules attached to a moiety. These moieties include, but are not limited to, detection moieties, hybridization moieties, purification moieties, delivery moieties, reaction moieties, binding moieties, and the like. The probe/primer typically comprises substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:8, SEQ ID NO:9, SEQ ID NO:10, SEQ ID NO:11, SEQ ID NO:12, SEQ ID NO:13, SEQ ID NO:14 and SEQ ID NO:22, an anti-sense sequence of one of the sequences set forth in SEQ ID NO:8, SEQ ID NO:9, SEQ ID NO:10, SEQ ID NO:11, SEQ ID NO:12, SEQ ID NO:13, SEQ ID NO:14 and SEQ ID NO:22, or naturally occurring mutants thereof. Primers based on a nucleotide sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 can be used in PCR reactions to clone TFSRP homologues. Probes based on the TFSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an TFSRP, such as by measuring a level of a TFSRP-encoding nucleic acid in a sample of cells, e.g., detecting TFSRP mRNA levels or determining whether a genomic TFSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326.

To assess the presence or relative quantity of protein translated from this mRNA, standard techniques, such as a Western blot, may be employed (see, for example, Ausubel et al., 1988 Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label that may be readily detected. The presence and quantity of label observed indicates the presence and quantity of the desired mutant protein present in the cell.

In one embodiment, the nucleic acid molecule of the invention encodes a protein or portion thereof which includes an amino acid sequence which is sufficiently homologous to an amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 such that the protein or portion thereof maintains the same or a similar function as the amino acid sequence to which it is compared. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23) amino acid residues to a TFSRP amino acid sequence such that the protein or portion thereof is able to participate in a stress tolerance response in a plant, or more particularly can participate in the transcription of a protein involved in a stress tolerance response in a *Physcomitrella patens* plant. Examples of such activities are also described herein. Examples of TFSRP activities are set forth in Table 1.

In another embodiment, the protein is at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:15, SEQ ID NO:16, SEQ ID NO:17, SEQ ID NO: 18, SEQ ID NO:19, SEQ ID NO:20, SEQ ID NO:21 or SEQ ID NO:23. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:8, SEQ ID NO:9, SEQ ID NO:10, SEQ ID NO:1, SEQ ID NO:12, SEQ ID NO:13, SEQ ID NO:14 or SEQ ID NO:22.

Portions of proteins encoded by the TFSRP nucleic acid molecules of the invention are preferably biologically active portions of one of the TFSRPs. As used herein, the term "biologically active portion of a TFSRP" is intended to include a portion, e.g., a domain/motif, of a TFSRP that participates in a stress tolerance response in a plant, or more particularly participates in the transcription of a protein involved in a stress tolerance response in a plant, or has an activity as set forth in Table 1. To determine whether a TFSRP or a biologically active portion thereof can participate in transcription of a protein involved in a stress tolerance response in a plant, a stress analysis of a plant expressing the TFSRP may be performed. Such analysis methods are well known to those skilled in the art, as detailed in Example 7.

Additional nucleic acid fragments encoding biologically active portions of a TFSRP can be prepared by isolating a portion of one of the sequences in SEQ ID NO:15, SEQ ID NO:16, SEQ ID NO:17, SEQ ID NO:18, SEQ ID NO:19, SEQ ID NO:20, SEQ ID NO:21 or SEQ ID NO:23, expressing the encoded portion of the TFSRP or peptide (e.g., by recombinant expression in vitro) and assessing the activity of the encoded portion of the TFSRP or peptide.

The invention further encompasses nucleic acid molecules that differ from one of the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22 (and portions thereof) due to degeneracy of the genetic code and thus encode the same TFSRP as that encoded by the nucleotide sequences shown in SEQ ID NO:8, SEQ ID NO:9, SEQ ID NO:10, SEQ ID NO:11, SEQ ID NO:12, SEQ ID NO:13, SEQ ID NO:14 or SEQ ID NO:22. In a further embodiment, the nucleic acid molecule of the invention encodes a full length *Physcomitrella patens* protein which is substantially homologous to an amino acid sequence of a polypeptide shown in SEQ ID NO:15, SEQ ID NO:16, SEQ ID NO:17, SEQ ID NO:18, SEQ ID NO:19, SEQ ID NO:20, SEQ ID NO:21 or SEQ ID NO:23.

In addition to the *Physcomitrella patens* TFSRP nucleotide sequences shown in SEQ ID NO:8, SEQ ID NO:9, SEQ ID NO:10, SEQ ID NO:11, SEQ ID NO:12, SEQ ID NO:13, SEQ ID NO:14 and SEQ ID NO:22, it will be appreciated by those skilled in the art that DNA sequence polymorphisms that lead to changes in the amino acid sequences of TFSRPs may exist within a population (e.g., the *Physcomitrella patens* population). Such genetic polymorphism in the TFSRP gene may exist among individuals within a population due to natural variation. As used herein, the terms "gene" and "recombinant gene" refer to nucleic acid molecules comprising an open reading frame encoding a TFSRP, preferably a *Physcomitrella patens* TFSRP. Such natural variations can typically result in 1-5% variance in the nucleotide sequence of the TFSRP gene. Any and all such nucleotide variations and resulting amino acid polymorphisms in a TFSRP that are the result of natural variation and that do not alter the functional activity of the TFSRPs are intended to be within the scope of the invention.

Nucleic acid molecules corresponding to natural variants and non-*Physcomitrella patens* homologues of the *Physcomitrella patens* TFSRP cDNA of the invention can be isolated based on their homology to *Physcomitrella patens* TFSRP nucleic acid disclosed herein using the *Physcomitrella patens* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology,* 6.3.1-6.3.6, John Wiley & Sons, N.Y. (1989). A preferred, non-limiting example of stringent hybridization conditions are hybridization in 6×sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Physcomitrella patens* TFSRP.

In addition to naturally-occurring variants of the TFSRP sequence that may exist in the population, the skilled artisan will further appreciate that changes can be introduced by mutation into a nucleotide sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22, thereby leading to changes in the amino acid sequence of the encoded TFSRP, without altering the functional ability of the TFSRP. For example, nucleotide substitutions leading to amino acid substitutions at "non-essential" amino acid residues can be made in a sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22. A "non-essential" amino acid residue is a residue that can be altered from the wild-type sequence of one of the TFSRPs (SEQ ID NO:15, SEQ ID NO:16, SEQ ID NO:17, SEQ ID NO:18, SEQ ID NO:19, SEQ ID NO:20, SEQ ID NO:21 and SEQ ID NO:23) without altering the activity of said TFSRP, whereas an "essential" amino acid residue is required for TFSRP activity. Other amino acid residues, however, (e.g., those that are not conserved or only semi-conserved in the domain having TFSRP activity) may not be essential for activity and thus are likely to be amenable to alteration without altering TFSRP activity.

Accordingly, another aspect of the invention pertains to nucleic acid molecules encoding TFSRPs that contain changes in amino acid residues that are not essential for TFSRP activity. Such TFSRPs differ in amino acid sequence from a sequence contained in SEQ ID NO:15, SEQ ID NO:16, SEQ ID NO:17, SEQ ID NO:18, SEQ ID NO:19, SEQ ID NO:20, SEQ ID NO:21 or SEQ ID NO:23, yet retain at least one of the TFSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 and is capable of participating in the a stress tolerance response in a plant, or more particularly participates in the transcription of a protein involved in a stress tolerance response in a *Physcomitrella patens* plant, or has one or more activities set forth in Table 1. Preferably, the protein encoded by the nucleic acid molecule is at least about 50-60% homologous to one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23, more preferably at least about 60-70% homologous to one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23, even more preferably at least about 70-80%, 80-90%, 90-95% homologous to one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23, and most preferably at least about 96%, 97%, 98%, or 99% homologous to one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23.

To determine the percent homology of two amino acid sequences (e.g., one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23) is occupied by the same amino acid residue or nucleotide as the corresponding position in the other sequence (e.g., a mutant form of the sequence selected from the polypeptide of SEQ ID NO:15, SEQ ID NO:16, SEQ ID NO:17, SEQ ID NO:18, SEQ ID NO:19, SEQ ID NO:20, SEQ ID NO:21 or SEQ ID NO:23), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). Preferably, the length of sequence comparison is at least 15 amino acid residues, more preferably at least 25 amino acid residues, and most preferably at least 35 amino acid residues.

Alternatively, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410). BLAST nucleic acid searches can be performed with the NBLAST program, score=100, wordlength=12 to obtain nucleic acid sequences homologous to TFSRP nucleic acid molecules of the invention. BLAST protein searches can be performed with the XBLAST program, score=50, wordlength=3 to obtain amino acid sequences homologous to TFSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the TFSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

An isolated nucleic acid molecule encoding a TFSRP homologous to a protein sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 can be created by introducing one or more nucleotide substitutions, additions or deletions into a nucleotide sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 such that one or more amino acid substitutions, additions or deletions are introduced into the encoded protein. Mutations can be introduced into one of the sequences of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a TFSRP is preferably replaced with another amino acid residue from the same side chain family. Alternatively, in another embodiment, mutations can be introduced randomly along all or part of a TFSRP coding sequence, such as by saturation mutagenesis, and the resultant mutants can be screened for a TFSRP activity described herein to identify mutants that retain TFSRP activity. Following mutagenesis of one of the sequences of SEQ ID NO:8, SEQ ID NO:9, SEQ ID NO:10, SEQ ID NO:11, SEQ ID NO:12, SEQ ID NO:13, SEQ ID NO:14 or SEQ ID NO:22, the encoded protein can be expressed recombinantly and the activity of the protein can be determined by analyzing the stress tolerance of a plant expressing the protein as described in Example 7.

In addition to the nucleic acid molecules encoding TFSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TFSRP coding strand, or to only a portion thereof. In one embodiment, an antisense nucleic acid molecule is antisense to a "coding region" of the coding strand of a nucleotide sequence encoding a TFSRP. The term "coding region" refers to the region of the nucleotide sequence comprising codons which are translated into amino acid residues (e.g., the entire coding region of , , , comprises nucleotides 1 to . . . ). In another embodiment, the antisense nucleic acid molecule is antisense to a "noncoding region" of the coding strand of a nucleotide sequence encoding TFSRP. The term "noncoding region" refers to 0.5° and 3' sequences that flank the coding region that are not translated into amino acids (i.e., also referred to as 5' and 3' untranslated regions).

Given the coding strand sequences encoding TFSRP disclosed herein (e.g., the sequences set forth in SEQ ID NO:8, SEQ ID NO:9, SEQ ID NO:10, SEQ ID NO:11, SEQ ID NO:12, SEQ ID NO:13, SEQ ID NO:14 and SEQ ID NO:22), antisense nucleic acids of the invention can be designed according to the rules of Watson and Crick base pairing. The antisense nucleic acid molecule can be complementary to the entire coding region of TFSRP mRNA, but more preferably is an oligonucleotide which is antisense to only a portion of the coding or noncoding region of TFSRP mRNA. For example, the antisense oligonucleotide can be complementary to the region surrounding the translation start site of TFSRP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)

uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a TFSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988 Nature 334:585-591)) can be used to catalytically cleave TFSRP mRNA transcripts to thereby inhibit translation of TFSRP mRNA. A ribozyme having specificity for a TFSRP-encoding nucleic acid can be designed based upon the nucleotide sequence of a TFSRP cDNA disclosed herein (i.e., SEQ ID NO:8, SEQ ID NO:9, SEQ ID NO:10, SEQ ID NO:11, SEQ ID NO:12, SEQ ID NO:13, SEQ ID NO:14 or SEQ ID NO:22) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an TFSRP-encoding mRNA. See, e.g., Cech et al. U.S. Pat. No. 4,987,071 and Cech et al. U.S. Pat. No. 5,116,742. Alternatively, TFSRP mRNA can be used to select a catalytic RNA having a specific ribonuclease activity from a pool of RNA molecules. See, e.g., Bartel, D. and Szostak, J. W., 1993 Science 261:1411-1418.

Alternatively, TFSRP gene expression can be inhibited by targeting nucleotide sequences complementary to the regulatory region of a TFSRP nucleotide sequence (e.g., a TFSRP promoter and/or enhancer) to form triple helical structures that prevent transcription of an TFSRP gene in target cells. See generally, Helene, C., 1991 Anticancer Drug Des. 6(6): 569-84; Helene, C. et al., 1992 Ann. N.Y. Acad. Sci. 660:27-36; and Maher, L. J., 1992 Bioassays 14(12):807-15.

The invention further provides an isolated recombinant expression vector comprising a nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TFSRPs, mutant forms of TFSRPs, fusion proteins, etc.).

The recombinant expression vectors of the invention can be designed for expression of TFSRPs in prokaryotic or eukaryotic cells. For example, TFSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia,* especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the TFSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant TFSRP unfused to GST can be recovered by cleavage of the fusion protein with thrombin.

Examples of suitable inducible non-fusion *E. coli* expression vectors include pTrc (Amann et al., 1988 Gene 69:301-315) and pET 11d (Studier et al., *Gene Expression Technology Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the TFSRP expression vector is a yeast expression vector. Examples of vectors for expression in yeast *S. cerevisiae* include pYepSec1 (Baldari, et al., 1987 Embo J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

Alternatively, the TFSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell. Biol. 3:2156-2165) and the pVL series (Lucklow and Summers, 1989 Virology 170:31-39).

In yet another embodiment, a nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 PNAS 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990 Science 249:374-379) and the fetoprotein promoter (Campes and Tilghman, 1989 Genes Dev. 3:537-546).

In another embodiment, the TFSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195-1197; and Bevan, M. W., 1984 Binary Agrobacterium vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plants cells and which are operably linked so that each sequence can fulfill its function, for example, termination of transcription by polyadenylation signals. Preferred polyadenylation signals are those originating from Agrobacterium tumefaciens t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CAMV (Franck et al., 1980 Cell 21:285-294), the 19S CaMV (see also U.S. Pat. No. 5,352,605 and WO8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (WO 95/19443), a tetracycline inducible promoter (Gatz et al., 1992 Plant J. 2:397-404) and an ethanol inducible promoter (WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinIII-promoter (EP 375091). For other examples of drought, cold, and salt-inducible promoters, such as the RD29A promoter, see Yamaguchi-Shinozalei et al. (1993 Mol. Gen. Genet. 236:331-340).

Especially those promoters are preferred which confer gene expression in specific tissues and organs, such as guard cells and the root hair cells. Suitable promoters include the napin-gene promoter from rapeseed (U.S. Pat. No. 5,608,152), the USP-promoter from Vicia faba (Baeumlein et al., 1991 Mol Gen Genet. 225(3):459-67), the oleosin-promoter from Arabidopsis (WO9845461), the phaseolin-promoter from Phaseolus vulgaris (U.S. Pat. No. 5,504,200), the Bce-4-promoter from Brassica (WO9113980) or the legumin B4 promoter (LeB4; Baeumlein et al., 1992 Plant Journal, 2(2): 233-9) as well as promoters conferring seed specific expression in monocot plants like maize, barley, wheat, rye, rice, etc. Suitable promoters to note are the lpt2 or lpt1-gene promoter from barley (WO 95/15389 and WO 95/23230) or those described in WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression as plastids are the compartment where precursors and some end products of lipid biosynthesis are synthesized. Suitable promoters are the viral RNA-polymerase promoter described in WO 95/16783 and WO 97/06250 and the clpP-promoter from Arabidopsis described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to TFSRP mRNA. Regulatory sequences operatively linked to a nucleic acid molecule cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TFSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crops plants are also preferred target plants for a genetic engineering as one further embodiment of the present invention.

In particular, the invention provides a method of producing a transgenic plant with a TFSRP coding nucleic acid, wherein expression of the nucleic acid in the plant results in increased tolerance to environmental stress as compared to a wild type variety of the plant comprising: (a) transforming a plant cell with an expression vector comprising a TFSRP nucleic acid, and (b) generating from the plant cell a transgenic plant with a increased tolerance to environmental stress as compared to a wild type variety of the plant. In preferred embodiments, the TFSRP is as described above. In preferred embodiments, the TFSRP coding nucleic acid is as described above. The invention also provides a method of increasing expression of a gene of interest within a host cell as compared to a wild type variety of the host cell, wherein the gene of interest is transcribed in response to a TFSRP, comprising: (a) transforming the host cell with an expression vector comprising a TFSRP coding nucleic acid, and (b) expressing the TFSRP within the host cell, thereby increasing the expression of the gene transcribed in response to the TFSRP as compared to a wild type variety of the host cell. In preferred embodiments, the TFSRP is as described above. In preferred embodiments, the TFSRP coding nucleic acid is as described above.

For such plant transformation, binary vectors such as pBinAR can be used (Höfgen and Willmitzer, 1990 Plant Science 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be archived by using a tissue specific promoter. For example, seed-specific expression can be archived by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, Crit. Rev. Plant Sci., 1996 4 (15):285-423). The signal peptide is cloned 5-prime in frame to the cDNA to archive subcellular localization of the fusion protein.

*Agrobacterium* mediated plant transformation can be performed using for example the GV3101(pMP90) (Koncz and Schell, 1986 Mol. Gen. Genet. 204:383-396) or LBA4404 (Clontech) *Agrobacterium tumefaciens* strain. Transformation can be performed by standard transformation techniques (Deblaere et al., 1994 Nucl. Acids. Res. 13:4777-4788). In one embodiment, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of a mRNA which encodes a polypeptide. Alternatively, the RNA can be an antisense RNA for use in affecting subsequent expression of the same or another gene or genes.

*Agrobacterium* mediated plant transformation can be performed using standard transformation and regeneration techniques (Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993.—360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13: 282-285. Additionally, transformation of soybean can be performed using for example a technique described in EP 0424 047, U.S. Pat. No. 5,322,783 (Pioneer Hi-Bred International) or in EP 0397 687, U.S. Pat. Nos. 5,376,543, 5,169,770 (University Toledo).

Plant transformation using particle bombardment, Polyethylene Glycol mediated DNA uptake or via the Silicon Carbide Fiber technique is for example described by Freeling and Walbot "The maize handbook" Springer Verlag: New York (1993) ISBN 3-540-97826-7. A specific example of maize transformation is found in U.S. Pat. No. 5,990,387 and a specific example of wheat transformation can be found in WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding an TFSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a TFSRP gene into which a deletion, addition or substitution has been introduced to thereby alter, e.g., functionally disrupt, the TFSRP gene. Preferably, this TFSRP gene is a *Physcomitrella patens* TFSRP gene, but it can be a homologue from a related plant or even from a mammalian, yeast, or insect source. In a preferred embodiment, the vector is designed such that, upon homologous recombination, the endogenous TFSRP gene is functionally disrupted (i.e., no longer encodes a functional protein; also referred to as a knock-out vector). Alternatively, the vector can be designed such that, upon homologous recombination, the endogenous TFSRP gene is mutated or otherwise altered but still encodes functional protein (e.g., the upstream regulatory region can be altered to thereby alter the expression of the endogenous TFSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the TFSRP gene is flanked at its 5' and 3' ends by additional nucleic acid molecule of the TFSRP gene to allow for homologous recombination to occur between the exogenous TFSRP gene carried by the vector and an endogenous TFSRP gene in a microorganism or plant. The additional flanking TFSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8): 4368-4373 for cDNA based recombination in *Physcomitrella patens*). The vector is introduced into a microorganism or plant cell (e.g., via polyethylene glycol mediated DNA) and cells in which the introduced TFSRP gene has homologously recombined with the endogenous TFSRP gene are selected, using art-known techniques.

In another embodiment, recombinant microorganisms can be produced which contain selected systems which allow for regulated expression of the introduced gene. For example, inclusion of a TFSRP gene on a vector placing it under control of the lac operon permits expression of the TFSRP gene only in the presence of IPTG. Such regulatory systems are well known in the art.

A host cell of the invention, such as a prokaryotic or eukaryotic host cell in culture, can be used to produce (i.e., express) a TFSRP. An alternate method can be applied in addition in plants by the direct transfer of DNA into developing flowers via electroporation or *Agrobacterium* medium gene transfer. Accordingly, the invention further provides methods for producing TFSRPs using the host cells of the invention. In one embodiment, the method comprises culturing the host cell of invention (into which a recombinant expression vector encoding a TFSRP has been introduced, or into which genome has been introduced a gene encoding a wild-type or altered TFSRP) in a suitable medium until TFSRP is produced. In another embodiment, the method further comprises isolating TFSRPs from the medium or the host cell.

Another aspect of the invention pertains to isolated TFSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of TFSRP in which the protein is separated from some of the cellular components of the cells in which it is naturally or recombinantly produced. In one embodiment, the language "substantially free of cellular material" includes preparations of TFSRP having less than about 30% (by dry weight) of non-TFSRP (also referred to herein as a "contaminating protein"), more preferably less than about 20% of non-TFSRP, still more preferably less than about 10% of non-TFSRP, and most preferably less than about 5% non-TFSRP. When the TFSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of TFSRP in which the protein is separated from chemical precursors or other chemicals that are involved in the synthesis of the protein. In one embodiment, the language "substantially free of chemical precursors or other chemicals" includes preparations of TFSRP having less than about 30% (by dry weight) of chemical precursors or non-TFSRP chemicals, more preferably less than about 20% chemical precursors or non-TFSRP chemicals, still more preferably less than about 10% chemical precursors or non-TFSRP chemicals, and most preferably less than about 5% chemical precursors or non-TFSRP chemicals. In preferred embodiments, isolated proteins or biologically active portions thereof lack contaminating proteins from the same organism from which the TFSRP is derived. Typically, such proteins are produced by recombinant expression of, for example, a *Physcomitrella patens* TFSRP in plants other than *Physcomitrella patens* or microorganisms such as *C. glutamicum*, ciliates, algae or fungi.

An isolated TFSRP or a portion thereof of the invention can participate in a stress tolerance response in a plant, or more particularly can participate in the transcription of a protein involved in a stress tolerance response in a *Physcomitrella patens* plant, or has one or more of the activities set forth in Table 1. In preferred embodiments, the protein or portion thereof comprises an amino acid sequence which is sufficiently homologous to an amino acid sequence encoded by a nucleic acid of SEQ ID NO:8, SEQ ID NO:9, SEQ ID NO:10, SEQ ID NO:11, SEQ ID NO:12, SEQ ID NO:13, SEQ ID NO:14 or SEQ ID NO:22 such that the protein or portion thereof maintains the ability to participate in the metabolism of compounds necessary for the construction of cellular membranes in *Physcomitrella patens*, or in the transport of molecules across these membranes. The portion of the protein is preferably a biologically active portion as described herein. In another preferred embodiment, a TFSRP of the invention has an amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23. In yet another preferred embodiment, the TFSRP has an amino acid sequence which is encoded by a nucleotide sequence which hybridizes, e.g., hybridizes under stringent conditions, to a nucleotide sequence of SEQ ID NO:8, SEQ ID NO:9, SEQ ID NO:10, SEQ ID NO:11, SEQ ID NO:12, SEQ ID NO:13, SEQ ID NO:14 or SEQ ID NO:22. In still another preferred embodiment, the TFSRP has an amino acid sequence which is at least about 50-60%, preferably at least about 60-70%, more preferably at least about 70-80%, 80-90%, 90-95%, and even more preferably at least about 96%, 97%, 98%, 99% or more homologous to one of the amino acid sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23. The preferred TFSRPs of the present invention also preferably possess at least one of the TFSRP activities described herein. For example, a preferred TFSRP of the present invention includes an amino acid sequence encoded by a nucleotide sequence which hybridizes, e.g., hybridizes under stringent conditions, to a nucleotide sequence of SEQ ID NO:8, SEQ ID NO:9, SEQ ID NO:10, SEQ ID NO:1, SEQ ID NO:12, SEQ ID NO:13, SEQ ID NO:14 or SEQ ID NO:22, and which can participate can participate in a stress tolerance response in a plant, or more particularly can participate in the transcription of a protein involved in a stress tolerance response in a *Physcomitrella patens* plant, or which has one or more of the activities set forth in Table 1.

In other embodiments, the TFSRP is substantially homologous to an amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 and retains the functional activity of the protein of one of the sequences of SEQ ID NO:15, SEQ ID NO:16, SEQ ID NO:17, SEQ ID NO:18, SEQ ID NO:19, SEQ ID NO:20, SEQ ID NO:21 or SEQ ID NO:23, yet differs in amino acid sequence due to natural variation or mutagenesis, as described in detail above. Accordingly, in another embodiment, the TFSRP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 and which has at least one of the TFSRP activities described herein. In another embodiment, the invention pertains to a full *Physcomitrella patens* protein which is substantially homologous to an entire amino acid sequence encoded by a nucleic acid of SEQ ID NO:8, SEQ ID NO:9, SEQ ID NO:10, SEQ ID NO:11, SEQ ID NO:12, SEQ ID NO:13, SEQ ID NO:14 or SEQ ID NO:22.

Biologically active portions of an TFSRP include peptides comprising amino acid sequences derived from the amino acid sequence of an TFSRP, e.g., an amino acid sequence of SEQ ID NO:15, SEQ ID NO:16, SEQ ID NO:17, SEQ ID NO:18, SEQ ID NO:19, SEQ ID NO:20, SEQ ID NO:21 or SEQ ID NO:23 or the amino acid sequence of a protein homologous to an TFSRP, which include fewer amino acids than a full length TFSRP or the full length protein which is homologous to an TFSRP, and exhibit at least one activity of an TFSRP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a TFSRP. Moreover, other biologically active portions, in which other regions of the protein are deleted, can be prepared by recombinant techniques and evaluated for one or more of the activities described herein. Preferably, the biologically active portions of a TFSRP include one or more selected domains/motifs or portions thereof having biological activity.

TFSRPs are preferably produced by recombinant DNA techniques. For example, a nucleic acid molecule encoding the protein is cloned into an expression vector (as described above), the expression vector is introduced into a host cell (as described above) and the TFSRP is expressed in the host cell. The TFSRP can then be isolated from the cells by an appropriate purification scheme using standard protein purification techniques. Alternative to recombinant expression, a TFSRP, polypeptide, or peptide can be synthesized chemically using standard peptide synthesis techniques. Moreover, native TFSRP can be isolated from cells (e.g., *Physcomitrella patens*), for example using an anti-TFSRP antibody, which can be produced by standard techniques utilizing a TFSRP or fragment thereof of this invention.

The invention also provides TFSRP chimeric or fusion proteins. As used herein, a TFSRP "chimeric protein" or "fusion protein" comprises a TFSRP polypeptide operatively linked to a non-TFSRP polypeptide. An "TFSRP polypeptide" refers to a polypeptide having an amino acid sequence corresponding to a TFSRP, whereas a "non-TFSRP polypeptide" refers to a polypeptide having an amino acid sequence corresponding to a protein which is not substantially homologous to the TFSRP, e.g., a protein which is different from the TFSRP and which is derived from the same or a different organism. Within the fusion protein, the term "operatively linked" is intended to indicate that the TFSRP polypeptide and the non-TFSRP polypeptide are fused to each other so that both sequences fulfill the proposed function attributed to the sequence used. The non-TFSRP polypeptide can be fused to the N-terminus or C-terminus of the TFSRP polypeptide. For example, in one embodiment, the fusion protein is a GST-TFSRP fusion protein in which the TFSRP sequences are fused to the C-terminus of the GST sequences. Such fusion proteins can facilitate the purification of recombinant TFSRPs. In another embodiment, the fusion protein is a TFSRP containing a heterologous signal sequence at its N-terminus. In certain host cells (e.g., mammalian host cells), expression and/or secretion of a TFSRP can be increased through use of a heterologous signal sequence.

Preferably, a TFSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, Eds. Ausubel et al. John Wiley & Sons: 1992). Moreover, many expression vectors are commercially available that already encode a fusion moiety (e.g., a GST polypeptide). A TFSRP-encoding nucleic acid can be cloned into such an expression vector such that the fusion moiety is linked in-frame to the TFSRP.

Homologues of the TFSRP can be generated by mutagenesis, e.g., discrete point mutation or truncation of the TFSRP. As used herein, the term "homologue" refers to a variant form of the TFSRP which acts as an agonist or antagonist of the activity of the TFSRP. An agonist of the TFSRP can retain substantially the same, or a subset, of the biological activities of the TFSRP. An antagonist of the TFSRP can inhibit one or more of the activities of the naturally occurring form of the TFSRP, by, for example, competitively binding to a downstream or upstream member of the cell membrane component metabolic cascade which includes the TFSRP, or by binding to an TFSRP which mediates transport of compounds across such membranes, thereby preventing translocation from taking place.

In an alternative embodiment, homologues of the TFSRP can be identified by screening combinatorial libraries of mutants, e.g., truncation mutants, of the TFSRP for TFSRP agonist or antagonist activity. In one embodiment, a variegated library of TFSRP variants is generated by combinatorial mutagenesis at the nucleic acid level and is encoded by a variegated gene library. A variegated library of TFSRP variants can be produced by, for example, enzymatically ligating a mixture of synthetic oligonucleotides into gene sequences such that a degenerate set of potential TFSRP sequences is expressible as individual polypeptides, or alternatively, as a set of larger fusion proteins (e.g., for phage display) containing the set of TFSRP sequences therein. There are a variety of methods which can be used to produce libraries of potential TFSRP homologues from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential TFSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477.

In addition, libraries of fragments of the TFSRP coding can be used to generate a variegated population of TFSRP fragments for screening and subsequent selection of homologues of a TFSRP. In one embodiment, a library of coding sequence fragments can be generated by treating a double stranded PCR fragment of a TFSRP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TFSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TFSRP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify TFSRP homologues (Arkin and Yourvan, 1992 PNAS 89:7811-7815; Delgrave et al., 1993 Protein Engineering 6(3):327-331). In another embodiment, cell based assays can be exploited to analyze a variegated TFSRP library, using methods well known in the art. The present invention further provides a method of identifying a novel TFSRP, comprising (a) raising a specific antibody response to a TFSRP, or fragment thereof, as described above; (b) screening putative TFSRP material with the antibody, wherein specific binding of the antibody to the material indicates the presence of a potentially novel TFSRP; and (c) analyzing the bound material in comparison to known TFSRP to determine its novelty.

The nucleic acid molecules, proteins, protein homologues, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of TFSRP regions required for function; modulation of an TFSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The TFSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a TFSRP coding nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example. In particular, the present invention describes using the expression of CABF-1 (SEQ ID NO:15), DBF-1 (SEQ ID NO:16), CBF-1 (SEQ ID NO:17), HDZ-1 (SEQ ID NO:18), ZF-1 (SEQ ID NO:19), LZ-1 (SEQ ID NO:20) and CABF-2 (SEQ ID NO:21) to engineer drought-tolerant plants. This strategy has herein been demonstrated for *Arabidopsis thaliana*, Rapeseed/Canola, soybeans, corn and wheat but its application is not restricted to these plants.

Accordingly, the invention provides a transgenic plant containing a TFSRP selected from 1) CABF-1; 2) CABF-2; 3) DBF-1; 4) CBF-1; 5) HDZ-1; 6) ZF-1; 7) LZ-1 as defined above, including homologues, wherein the environmental stress is drought. This invention also describes the principle of using over-expression of ZF-1 (SEQ ID NO:19), CABF-2 (SEQ ID NO:21) and LZ-1 (SEQ ID NO:20) to engineer salt-tolerant plants. Again, this strategy has herein been demonstrated for Arabidopsis thaliana, Rapeseed/Canola, soybeans, corn and wheat but its application is not restricted to these plants. Accordingly, the invention provides a transgenic plant containing the TFSRP selected from 1) CABF-2; 2) ZF-1); and 3) LZ-1 as defined above, including homologues, wherein the environmental stress is salinity.

The present invention also provides methods of modifying stress tolerance of a plant comprising, modifying the expression of a TFSRP in the plant. The invention provides that this method can be performed such that the stress tolerance is either increased or decreased.

Furthermore, this method can be used wherein the plant is either transgenic or not transgenic. In cases when the plant is transgenic, the plant can be transformed with a vector containing any of the above described TFSRP coding nucleic acids, or the plant can be transformed with a promoter that directs expression of native TFSRP in the plant, for example. The invention provides that such a promoter can be tissue specific. Furthermore, such a promoter can be developmentally regulated. Alternatively, non-transgenic plants can have native TFSRP expression modified by inducing a native promoter. Furthermore, the invention provides that TFSRP expression can be modified by administration of an anti-sense molecule that inhibits expression of TFSRP.

The expression of CABF-1 (SEQ ID NO:15), DBF-1 (SEQ ID NO:16), CBF-1 (SEQ ID NO:17), HDZ-1 (SEQ ID NO:18), ZF-1 (SEQ ID NO:19), LZ-1 (SEQ ID NO:20) and CABF-2 (SEQ ID NO:21) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the CABF-1 (SEQ ID NO:15), DBF-1 (SEQ ID NO:16), CBF-1 (SEQ ID NO:17), HDZ-1 (SEQ ID NO:18), ZF-1 (SEQ ID NO:19), LZ-1 (SEQ ID NO:20) and CABF-2 (SEQ ID NO:21) homologues in the target plant as well as from its promoter. Zinc-finger-containing recombinant transcription factors are engineered to specifically interact with the CABF-1 (SEQ ID NO:15), DBF-1 (SEQ ID NO:16), CBF-1 (SEQ ID NO:17), HDZ-1 (SEQ ID NO:18), ZF-1 (SEQ ID NO:19), LZ-1 (SEQ ID NO:20) and CABF-2 (SEQ ID NO:21) homologue and transcription of the corresponding gene is activated.

As shown herein and described more fully below, expression of the TFSRPs (CABF-1 (SEQ ID NO:15), DBF-1 (SEQ ID NO:16), CBF-1 (SEQ ID NO:17), HDZ-1 (SEQ ID NO:18), ZF-1 (SEQ ID NO:19), LZ-1 (SEQ ID NO:20) and CABF-2 (SEQ ID NO:21)) in Arabidopsis thaliana confers a high degree of drought tolerance to the plant. Additionally, several TFSRPs confer tolerance to high salt concentrations (ZF-1 (SEQ ID NO:19), LZ-1 (SEQ ID NO:20) and CABF-2 (SEQ ID NO:21)) to this plant. Under drought stress conditions, CABF-1 over-expressing lines showed a survival rate of 89%, DBF-1 over-expressing lines showed a survival rate of 80%, CBF-1 over-expressing lines showed a survival rate of 100%; HDZ-1 over-expressing lines showed a survival rate of 50%, ZF-1 over-expressing lines showed a survival rate of 57%, LZ-1 over-expressing lines showed a survival rate of 79%, and CABF-2 over-expressing lines showed a survival rate of 50%. Under salt stress conditions, ZF-1 over-expressing lines showed a survival rate of 52%, CABF-2 over-expressing lines showed a survival rate of 56% and LZ-1 over-expressing lines showed a survival rate of 48%. The untransformed controls showed a survival rate of 10%. It is noteworthy that the analyses of these transgenic lines were performed with T1 plants. Therefore, the results will be better when a homozygous, strong expresser is found. Further proof of involvement of these genes in stress tolerance is given by the increase in the level of transcript in response to cold temperature treatment. The concentration of the transcripts for CABF-1, CABF-2, and CBF-1 are all increased 2 fold over untreated background following the treatment.

In addition to introducing the TFSRP nucleic acid sequences into transgenic plants, these sequences can also be used to identify an organism as being Physcomitrella patens or a close relative thereof. Also, they may be used to identify the presence of Physcomitrella patens or a relative thereof in a mixed population of microorganisms. The invention provides the nucleic acid sequences of a number of Physcomitrella patens genes; by probing the extracted genomic DNA of a culture of a unique or mixed population of microorganisms under stringent conditions with a probe spanning a region of a Physcomitrella patens gene which is unique to this organism, one can ascertain whether this organism is present.

Further, the nucleic acid and protein molecules of the invention may serve as markers for specific regions of the genome. This has utility not only in the mapping of the genome, but also in functional studies of Physcomitrella patens proteins. For example, to identify the region of the genome to which a particular Physcomitrella patens DNA-binding protein binds, the Physcomitrella patens genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of Physcomitrella patens, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The TFSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the TFSRP nucleic acid molecules of the invention may result in the production of TFSRPs having functional differences from the wild-type TFSRPs. These proteins may be improved in efficiency or activity, may be present in greater numbers in the cell than is usual, or may be decreased in efficiency or activity.

There are a number of mechanisms by which the alteration of a TFSRP of the invention may directly affect stress response and/or stress tolerance. In the case of plants expressing TFSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived therefrom can then be assayed for fail or alteration of their tolerance to drought, salt, and temperature stress.

The engineering of one or more TFSRP genes of the invention may also result in TFSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more TFSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells. (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation include U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for TFSRPs to result in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated TFSRP nucleic acid and protein molecules such that the stress tolerance is improved.

The present invention also provides antibodies which specifically bind to a TFSRP-polypeptide, or a portion thereof, as encoded by a nucleic acid disclosed herein or as described herein. Antibodies can be made by many well-known methods (See, e.g. *Harlow and Lane*, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H.L.K. Whitehouse in Gransden Wood, Huntingdonshire (England), which was subcultured from a spore by Engel (1968, Am. J. Bot. 55:438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65 W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 min using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of total RNA and poly-(A)+RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al., 1994 Mol. Gen. Genet. 244:352-359). The Poly(A)+ RNA was isolated using Dyna Beads® (Dynal, Oslo, Norway) following the instructions of the manufacturers protocol. After determination of the concentration of the RNA or of the poly(A)+ RNA, the RNA was precipitated by addition of ⅒ volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 2 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:24

5'-CTAAAGGGAACAAAAGCTG-3'     SEQ ID NO:25

5'-TGTAAAACGACGGCCAGT-3'      SEQ ID NO:26
```

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R., 1990 Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P., 1997 75% accuracy in protein secondary structure prediction. Proteins, 27:329-335; CLUSTALW: Multiple sequence alignment. Thompson, J. D., Higgins, D. G. and Gibson, T. J. (1994); CLUSTAL W: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P., 1994 Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C., 1984 Prediction of protein function from sequence properties: A discriminate analysis of a database. Biochim. Biophys. Acta 787:221-226. Version 2 by Dr. K. Nakai; PROSEARCH: Detection of PROSITE protein sequence patterns. Kolakowski L. F. Jr., Leunissen J. A. M., Smith J. E., 1992 ProSearch: fast searching of protein sequences with regular expression patterns related to protein structure and function. Biotechniques 13:919-921; BLIMPS: Similarity searches against a database of ungapped blocks. J. C. Wallace and Henikoff S., 1992; PATMAT: A searching and extraction program for sequence, pattern and block queries and databases, CABIOS 8:249-254. Written by Bill Alford.

Example 5

Identification of *Physcomitrella patens* ORF Corresponding to CABF-1, DBF-1, CBF-1, HDZ-1, ZF-1, LZ-1 and CABF-2

The *Physcomitrella patens* partial cDNAs (ESTs) shown in Table 1 below were identified in the *Physcomitrella patens* EST sequencing program using the program EST-MAX through BLAST analysis. (Tables 2-8 show some of these results). The Sequence Identification Numbers corresponding to these ESTs are as follows: CABF-1 (SEQ ID NO:1), DBF-1 (SEQ ID NO:2), CBF-1 (SEQ ID NO:3), HDZ-1 (SEQ ID NO:4), ZF-1 (SEQ ID NO:5), LZ-1 (SEQ ID NO:6) and CABF-2 (SEQ ID NO:7) These particular clones were chosen for further analyses since they encoded for transcription factors.

TABLE 1

| Functional Category | Putative Function | Sequence Code | ORF position | Name |
|---|---|---|---|---|
| Transcription Factor | DNA-binding protein | s_pp001031077f | 1-515 | DBF-1 |
| | transcription factor, CCAAT-binding, chain A | c_pp004053131r | 500-1 | CABF-1 |
| | transcription factor | s_pp004052093r | 2-508 | CABF-2 |
| | zinc finger protein | c_pp001074039r | 1154-447 | ZF-1 |
| | homeodomain leucine zipper protein | c_pp001058012r | 364-750 | HDZ-1 |
| | DNA-binding protein VBP1 | s_pp013006061r | 1-371 | LZ-1 |
| | transcriptional activator CBF1 | c_pp004032055r | 183-998 | CBF-1 |

TABLE 2

Degree of amino acid identity and similarity of PpHDZ-1 and other homologous proteins (GCG Gap program was used: gap penalty: 10; gap extension penalty: 0.1; score matrix: blosum62)

| Swiss-Prot # | Q9LS31 | Q9LS33 | Q43529 | Q9XH37 | Q9SP47 |
|---|---|---|---|---|---|
| Protein name | Homeobox protein PPHB7 | Homeobox protein PPHB5 | Homeobox | Homeodomain leucine zipper protein | Homeodomain leucine zipper protein 57 |

TABLE 2-continued

Degree of amino acid identity and similarity of PpHDZ-1 and other homologous proteins (GCG Gap program was used: gap penalty: 10; gap extension penalty: 0.1; score matrix: blosum62)

| Swiss-Prot # | Q9LS31 | Q9LS33 | Q43529 | Q9XH37 | Q9SP47 |
|---|---|---|---|---|---|
| Species | *Physcomitrella patens* (Moss) | *Physcomitrella patens* (Moss) | *Lycopersicon esculentum* (Tomato) | *Oryza sativa* (Rice) | *Glycine max* (Soybean) |
| Identity % | 71% | 38% | 30% | 29% | 30% |
| Similarity % | 72% | 51% | 40% | 39% | 36% |

TABLE 3

Degree of amino acid identity and similarity of PpZF-1 and other homologous proteins (GCG Gap program was used: gap penalty: 10; gap extension penalty: 0.1; score matrix: blosum62)

| Swiss-Prot # | Q9SK53 | Q9ZTK7 | Q9ZTK8 | Q9XE47 | O82431 |
|---|---|---|---|---|---|
| Protein name | Constans-like B-box zinc finger protein | Constans-like protein 2 | Constans-like protein 1 | Zinc finger protein | Constans-like 1 protein |
| Species | *Arabidopsis thaliana* (Mouse-ear cress) | *Arabidopsis thaliana* (Mouse-ear cress) | *Malus domestica* (Apple) (*Malus sylvestris*) | *Pinus radiata* (Monterey pine) | *Raphanus sativus* (Radish) |
| Identity % | 40% | 43% | 42% | 39% | 41% |
| Similarity % | 50% | 54% | 54% | 49% | 53% |

TABLE 4

Degree of amino acid identity and similarity of PpCABF-1 and other homologous proteins (GCG Gap program was used: gap penalty: 10; gap extension penalty: 0.1; score matrix: blosum62)

| Swiss-Prot # | Q9ZQC3 | O23310 | P25209 | Q9LFI3 | O23633 |
|---|---|---|---|---|---|
| Protein name | Putative CCAAT-binding transcription factor | CCAAT-binding transcription factor subunit A | CCAAT-binding transcription factor subunit A | Transcription factor NF-Y, CCAAT-binding-like protein | Transcription factor |
| Species | *Arabidopsis thaliana* (Mouse-ear cress) | *Arabidopsis thaliana* (Mouse-ear cress) | *Zea mays* (Maize) | *Arabidopsis thaliana* (Mouse-ear cress) | *Arabidopsis thaliana* (Mouse-ear cress) |
| Identity % | 47% | 53% | 49% | 41% | 46% |
| Similarity % | 58% | 56% | 57% | 53% | 52% |

TABLE 5

Degree of amino acid identity and similarity of PpDBF-1 and other homologous proteins (GCG Gap program was used: gap penalty: 10; gap extension penalty: 0.1; score matrix: blosum62)

| Swiss-Prot # | Q9ZUL5 | O45609 | Q9NPU9 |
|---|---|---|---|
| Protein name | Putative DNA-binding protein | M03C11.8 protein | Hypothetical 68.6 KDA protein |
| Species | *Arabidopsis thaliana* (Mouse-ear cress) | *Caenorhabditis elegans* | *Homo sapiens* (Human) |
| Identity % | 47% | 24% | 25% |
| Similarity % | 58% | 35% | 37% |

TABLE 6

Degree of amino acid identity and similarity of PpCABF-2 and other homologous proteins (GCG Gap program was used: gap penalty: 10; gap extension penalty: 0.1; score matrix: blosum62)

| Swiss-Prot # | O23636 | Q9SNZ0 | Q9SMP0 | Q92869 | O35088 |
|---|---|---|---|---|---|
| Protein name | Transcription factor | Heme activated protein | Transcription factor HAP5A | Transcription factor NF-YC subunit | Nuclear factor YC |
| Species | Arabidopsis thaliana (Mouse-ear cress) | Arabidopsis thaliana (Mouse-ear cress) | Arabidopsis thaliana (Mouse-ear cress) | Homo sapiens (Human) | Mus musculus (Mouse) |
| Identity % | 54% | 40% | 42% | 26% | 25% |
| Similarity % | 62% | 49% | 49% | 31% | 30% |

TABLE 7

Degree of amino acid identity and similarity of PpLZ-1 and other homologous proteins (GCG Gap program was used: gap penalty: 10; gap extension penalty: 0.1; score matrix: blosum62)

| Swiss-Prot # | Q9SQK1 | P43273 | O24160 | Q06979 | Q41558 |
|---|---|---|---|---|---|
| Protein name | BZIP Transcription factor | Transcription factor HBP-1B | Leucine zipper transcription factor TGA2.1 | OCS-element binding factor 3.2 | Transcription factor HBP-1B(C1) |
| Species | Nicotiana tabacum (Common tobacco) | Arabidopsis thaliana (Mouse-ear cress) | Nicotiana tabacum (Common tobacco) | Zea mays (Maize) | Triticum aestivum (Wheat) |
| Identity % | 62% | 73% | 46% | 46% | 45% |
| Similarity % | 74% | 61% | 55% | 53% | 53% |

TABLE 8

Degree of amino acid identity and similarity of PpCBF-1 and other homologous proteins (GCG Gap program was used: gap penalty: 10; gap extension penalty: 0.1; score matrix: blosum62)

| Swiss-Prot # or Genbank # | Q9M210 | BAA33435 | Q9LU18 | Q9ZQP3 | Q9SUK8 |
|---|---|---|---|---|---|
| Protein name | Transcription factor-like protein | DREB1B | Transcription factor TINY-like protein | Putative TINY protein | Apetala2 domain TINY like protein |
| Species | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 22% | 21% | 21% | 20% | 20% |
| Similarity % | 35% | 32% | 32% | 30% | 27% |

Example 6

Cloning of the Full-Length *Physcomitrella patens* cDNA Encoding for CABF-1, DBF-1, CBF-1, HDZ-1, ZF-1, LZ-1, CABF-2

To isolate full-length CABF-1 (SEQ ID NO:8), CABF-2 (SEQ ID NO:14), CBF-1 (SEQ ID NO:10), PCR was performed as described below under the title "Full-length Amplification" using the original ESTs described in Example 4 as template since they were full-length (see Table 9 for primers).

TABLE 9

Scheme and primers used for cloning of full-length clones

| Gene | Final sites in product | Isolation Method | Primers Race | Primer RT-PCR |
|------|------------------------|------------------|--------------|---------------|
| DBF-1 | XmaI/HpaI | 5' RACE and RT-PCR for Full-length clone | RC056 (SEQ ID NO:27) 5'GCGATCCTCAGCC TGTCGATCCATT3' RC116 (SEQ ID NO:28) 5'CCCTGAGGTATCG TTCCTGGTTCCCA3' | RC279 (SEQ ID NO:29) 5'ATCCCGGGCGAT GGTGCGTTCGAGAG ATCGTAAGG3' RC280 (SEQ ID NO:30) 5'GCGTTAACGAGC TTTCTCGCAGTGCC AGATAA3' |
| CABF-2 | XmaI/SacI | PCR of original EST clone | | RC031 (SEQ ID NO:31) ATCCCGGGCTCTGC ACCCCAGATGTCGC ATCCT RC032: (SEQ ID NO:32) CTGAGCTCTAATGC ATTCACTGTTGCTG CTGCT |
| LZ-1 | HpaI/EcoRV | 5' RACE and RT-PCR for Full-length clone | RC058 (SEQ ID NO:33) 5'CCTGTAGGGCCA CCCGGAGCTCACT3' | RC108 (SEQ ID NO:34) 5'GAGTTAACGCAG TGGTCACAACGCAG AGTACGC3' RC109 (SEQ ID NO:35) 5'GCGATATCGCTTC CATACCTGCGCCGA AGACTT3' |
| CBF-1 | XmaI/HpaI | PCR of original EST clone | | RC033 (SEQ ID NO:36) 5'GACCCGGGCCAT GTGATATGGCTTCA AAGTAT3' RC034 (SEQ ID NO:37) 5'GCGTTAACGACTC ACTGAGAGTCATAA TGGTG3' |
| HDZ-1 | XmaI/HpaI | 5' RACE and RT-PCR for Full-length clone | RC047 (SEQ ID NO:38) 5'CGTAGTCGCGCTC GAGCTGTTTGGT3' | RC321 (SEQ ID NO:39) 5'ATCCCGGGCACG AGGGCAAGAGGGG ATAGAGAC3' RC322 (SEQ ID NO:40) 5'GCGTTAACGCCG ATGGTGCAACTTTG GTTGAC3' |
| ZF-1 | XmaI/SacI | 5' RACE and RT-PCR for Full-length | RC063 (SEQ ID NO:41) 5'CCGTGTCCTCGGA | RC122 (SEQ ID NO:42) 5'ATCCCGGGAGGA |

TABLE 9-continued

Scheme and primers used for cloning of full-length clones

| Gene | Final sites in product | Isolation Method | Primers Race | Primer RT-PCR |
|------|------------------------|------------------|--------------|---------------|
| | | clone | GCATTCTGGCAT3' | GGGAGTTGGAATCT AGGAGAC3' RC124 (SEQ ID NO:43) 5'GCGAGCTCGACC TTGCTCGATGGAGA CTCCAAT3' |
| CABF-1 | XmaI/SacI | PCR of original EST clone | | RC019 (SEQ ID NO:44) 5'ATCCCGGGAATA GGACGGATGGCCG ACAGTTAC3' RC020 (SEQ ID NO:45) 5'ATGAGCTCAC TCTTACACTCCG CGGGGTTGGTT3' |

To isolate the clones encoding for DBF-1 (SEQ ID NO:9), HDZ-1 (SEQ ID NO:11), ZF-1 (SEQ ID NO:12) and LZ-1 (SEQ ID NO:13) from *Physcomitrella patens*, cDNA libraries were created with SMART RACE cDNA Amplification kit (Clontech Laboratories) following manufacturer's instructions. Total RNA isolated as described in Example 2 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points above. RNA was then pulled and used for isolation.

5' RACE Protocol

The EST sequences DBF-1 (SEQ ID NO:2), HDZ-1 (SEQ ID NO:4), ZF-1 (SEQ ID NO:5) and LZ-1 (SEQ ID NO:6) identified from the database search as described in Example 4 were used to design oligos for RACE (see Table 9). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of HDZ-1, ZF-1 and LZ-1 and were used to design oligos for full-length cloning of the respective genes (see below full-length amplification). The RACE product of DBF-1 was not full length and a new RACE reaction was needed (see Table 9 for primers).

Full-Length Amplification

Full-length clones corresponding CABF-1 (SEQ ID NO:8), CBF-1 (SEQ ID NO:10) and CABF-2 (SEQ ID NO:14) were obtained by performing polymerase chain reaction (PCR) with gene-specific primers (see Table 9) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

Full-length clones corresponding to the DBF-1 (SEQ ID NO:9), HDZ-1 (SEQ ID NO:11), ZF-1 (SEQ ID NO:12) and LZ-1 (SEQ ID NO:13) genes were isolated by repeating the RACE method but using the gene-specific primers as given in Table 9.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

Example 7

Engineering Stress-Tolerant *Arabidopsis* Plants by Over-Expressing the Genes CABF-1, DBF-1, CBF-1, HDZ-1, ZF-1, LZ-1 and CABF-2

Binary Vector Construction: nGMSG

The pLMNC53 (Mankin, 2000, PhD thesis) vector was digested with HindIII (Roche) and blunt-end filled with Klenow enzyme and 0.1 mM dNTPs (Roche) according to manufacturer's instructions. This fragment was extracted from agarose gel with a QIAquick Gel Extraction Kit (Qiagen)

according to manufacturer's instructions. The purified fragment was then digested with EcoRI (Roche) according to manufacturer's instructions. This fragment was extracted from agarose gel with a QIAquick Gel Extraction Kit (Qiagen) according to manufacturer's instructions. The resulting 1.4 kilobase fragment, the gentamycin cassette, included the nos promoter, aacCI gene and the g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Both the pGMBS vector and plbxSuperGUS vector were digested with XbaI and KpnI (Roche) according to manufacturer's instructions, excising the gentamycin cassette from pGMBS and producing the backbone from the plbxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pGMSG) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) and grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

Subcloning of CABF-1, DBF-1, CBF-1, HDZ-1, ZF-1, LZ-1 and CABF-2 into the Binary Vector The fragments containing the different *Physcomitrella patens* transcription factors were subcloned from the recombinant PCR2.1 TOPO vectors by double digestion with restriction enzymes (see Table 10) according to manufacturer's instructions. The subsequence fragment was excised from agarose gel with a QIAquick Gel Extraction Kit (QIAgen) according to manufacturer's instructions and ligated into the binary vector pGMSG, cleaved with appropriate enzymes (see Table 10) and dephosphorylated prior to ligation. The resulting recombinant pGMSG vector contained the corresponding transcription factor in the sense orientation under the control of the constitutive super promoter.

TABLE 10

Names of the various constructs of the *Physcomitrella patens* transcription factors used for plant transformation

| Gene | Enzymes used to generate gene fragment | Enzymes used to restrict pGMSG | Binary Vector Construct |
| --- | --- | --- | --- |
| CABF-1 | XmaI/SacI | XmaI/SacI | pBPSSH003 |
| DBF-1 | XmaI/HpaI | XmaI/Ecl136 | pBPSLVM009 |
| CBF-1 | XmaI/HpaI | XmaI/Ecl136 | pBPSSH002 |
| HDZ-1 | XmaI/HpaI | XmaI/Ecl136 | pBPSLVM007 |
| ZF-1 | XmaI/SacI | XmaI/SacI | pBPSLVM008 |
| LZ-1 | HpaI/EcoRV | Ecl136 | pBPSLVM012 |
| CABF-2 | XmaI/SacI | XmaI/SacI | pBPSMI003 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold, 1993 Acad. Sci. Paris. 316:1194-1199; Bent et al., 1994 Science 265:1856-1860).

Screening of Transformed Plants

T1 seeds were sterilized according to standard protocols (Xiong et al. 1999, Plant Molecular Biology Reporter 17: 159-170). Seeds were plated on ½ MS 0.6% agar supplemented with 1% sucrose, 150 µg/ml gentamycin (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}m^{-2}$ (white light; Philips TL 65 W/25 fluorescent tube) and 16 hours light and 8 hours dark day length cycle. Transformed seedlings were selected after 14 days and transferred to ½ MS 0.6% agar plates supplemented with 1% sucrose and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromole $s^{-1}$ $m^{-2}$ (white light; Philips TL 65 W/25 fluorescent tube). The RH was then decreased to 60% and the seedlings were desiccated further for eight hours. Seedlings were then removed and placed on ½ MS 0.6% agar plates supplemented with 2 µg/ml benomyl and scored after five days.

The results of the drought tolerance screening in *Arabidopsis thaliana* plants over-expressing the TFSRP are shown in Table 11. It is noteworthy that these analyses were performed with T1 plants since the results should be better when a homozygous, strong expresser is found.

TABLE 11

Summary of the drought stress tests

| Gene Name | Drought Stress Test | | |
|---|---|---|---|
| | Number of survivors | Total number of plants | Percentage of survivors |
| HDZ-1 | 7 | 14 | 50% |
| ZF-1 | 25 | 45 | 53% |
| CABF-1 | 8 | 9 | 89% |
| DBF-1 | 4 | 5 | 80% |
| CABF-2 | 3 | 6 | 50% |
| LZ-1 | 11 | 14 | 79% |
| CBF-1 | 9 | 9 | 100% |
| Control | 18 | 84 | 21% |

Salt Tolerance Screening

Seedlings were transferred to filter paper soaked in ½ MS and placed on ½ MS 0.6% agar supplemented with 2 μg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 μg/ml benomyl. The seedlings were scored after 5 days.

The results of the salt tolerance screening in *Arabidopsis thaliana* plants over-expressing the TFSRPs are shown in Table 12. In particular, ZF-1 over-expressing *Arabidopsis thaliana* plants showed a 52% (12 survivors from 23 stressed plants) survival rate; LZ-1, 48% (10 survivor from 21 stressed plants); CABF-2, 56% (5 survivors from 9 stressed plants); whereas the untransformed control a 9% (2 survivors from 23 tested plants) survival rate. It is noteworthy that these analyses were performed with T1 plants, and therefore, the results should be better when a homozygous, strong expresser is found.

TABLE 12

Summary of the salt stress tests

| Gene Name | Salt Stress Test | | |
|---|---|---|---|
| | Number of survivors | Total number of plants | Percentage of survivors |
| ZF-1 | 12 | 23 | 52% |
| CABF-2 | 5 | 9 | 56% |
| LZ-1 | 10 | 21 | 48% |
| Control | 2 | 23 | 9% |

Freezing Tolerance Screening

Seedlings were moved to petri dishes containing ½ MS 0.6% agar supplemented with 2% sucrose and 2 μg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing 1° C./hour. The seedlings were then incubated at −5.0° C. for 24 hours and then allowed to thaw at 5° C. for 12 hours. The water was poured off and the seedlings were scored after 5 days. The transgenic plants are then screened for their improved cold tolerance demonstrating that transgene expression confers cold tolerance.

Example 8

Detection of the CABF-1, DBF-1, CBF-1, HDZ-1, ZF-1, LZ-1, and CABF-2 Transgenes in the Transgenic *Arabidopsis* Lines One leaf from a wild type and a transgenic *Arabidopsis* plant was homogenized in 250 μl Hexadecyltrimethyl ammonium bromide (CTAB) buffer (2% CTAB, 1.4 M NaCl, 8 mM EDTA and 20 mM Tris pH 8.0) and 1 μl β-mercaptoethanol. The samples were incubated at 60-65° C. for 30 minutes and 250 μl of Chloroform was then added to each sample. The samples were vortexed for 3 minutes and centrifuged for 5 minutes at 18,000×g. The supernatant was taken from each sample and 150 μl isopropanol was added. The samples were incubated at room temperature for 15 minutes, and centrifuged for 10 minutes at 18,000×g. Each pellet washed with 70% ethanol, dried, and resuspended in 20 μl TE. 4 μl of above suspension was used in a 20 μl PCR reaction using Taq DNA polymerase (Roche Molecular Biochemicals) according to the manufacturer's instructions. Binary vector plasmid containing each TFSRP gene was used as positive control, and the wild type C24 genomic DNA was used as negative control in the PCR reactions. 10 μl PCR reaction was analyzed on 0.8% agarose—ethidium bromide gel.

The primers and reaction times used for amplification of each TFSRP gene are below. Notably, the transgenes were successfully amplified from the T1 transgenic lines, but not from the wild type C24. This result indicates that the T1 transgenic plants contain at least one copy of the transgenes. There was no indication of the existence of either identical or very similar genes in the untransformed *Arabidopsis thaliana* control which could be amplified by this method.

CABF-1

The primers used in the reactions were:

SEQ ID NO:46
5'GAATAGATACGCTGACACGC3'

SEQ ID NO:47
5'ATGAGCTCACTCTTACACTCCGCGGGGTTGGTT3'

The PCR program was: 1 cycle of 1 minute at 94° C., 1 minute at 75° C. and 3 minutes at 72° C., followed by 14 cycles of the same cycle except that the annealing temperature decreased 1° C. every cycle until 62° C.; and then 16 cycles of 1 minute at 94° C., 1 minute at 62° C. and 3 minutes at 72° C. A 600-base pair fragment was generated from the positive control and the transgenic plants.

HDZ-1

The primers used in the reactions were:

SEQ ID NO:46
5'GAATAGATACGCTGACACGC3'

SEQ ID NO:48
5'GCGTTAACGCCGATGGTGCAACTTTGGTTGAC3'

The PCR program was as following: 30 cycles of 1 minute at 94° C., 1 minute at 62° C. and 4 minutes at 72° C., followed by 10 minutes at 72° C. A 1,3-kb fragment was produced from the positive control and the transgenic plants.

ZF-1

The primers used in the reactions were:

SEQ ID NO:46
5'GAATAGATACGCTGACACGC3'

SEQ ID NO:49
5'GCGAGCTCGACCTTGCTCGATGGAGACTCCAAT3'

The PCR program was as following: 1 cycle of 1 minute at 94° C., 1 minute at 75° C. and 3 minutes at 72° C., followed by 14 cycles of the same cycle except that the annealing temperature decreased 1° C. every cycle until 62° C.; and then 16 cycles of 1 minute at 94° C., 1 minute at 62° C. and 3 minutes at 72° C. A 1,3-kb fragment was generated from the positive control and the T1 transgenic plants.

CBF-1

The primers used in the reactions were:

SEQ ID NO:46
5'GAATAGATACGCTGACACGC3'

SEQ ID NO:50
5'GCGTTAACGACTCACTGAGAGTCATAATGGTG3'

The PCR program was as following: 1 cycle, of 1 minute at 94° C., 1 minute at 75° C. and 3 minutes at 72° C., followed by 14 cycles of the same cycle except that the annealing temperature decreased 1° C. every cycle until 62° C.; and then 16 cycles of 1 minute at 94° C., 1 minute at 62° C. and 3 minutes at 72° C. A 1.1-kb fragment was generated from the positive control and the T1 transgenic plants.

DBF-1

The primers used in the reactions were:

SEQ ID NO:51
5'CTAGTAACATAGATGACACC3'

SEQ ID NO:52
5'ATCCCGGGCGATGGTGCGTTCGAGATCGTAAGG3'

The PCR program was as following: 30 cycles of 1 minute at 94° C., 1 minute at 62° C. and 4 minutes at 72° C., followed by 10 minutes at 72° C. A 2,9-kb fragment was produced from the positive control and the transgenic plants.

CABF-2

The primers used in the reactions were:

SEQ ID NO:53
5'GAATAGATACGCTGACACGC3'

SEQ ID NO:54
5'CTGAGCTCTAATGCATTCACTGTTGCTGCTGCT3'

The PCR program was as following: 30 cycles of 1 minute at 94° C., 1 minute at 62° C. and 4 minutes at 72° C., followed by 10 minutes at 72° C. An 800-bp fragment was produced from the positive control and the transgenic plants.

LZ-1

The primers used in the reactions were:

SEQ ID NO:53
5'GAATAGATACGCTGACACGC3'

SEQ ID NO:55
5'GCGATATCGCTTCCATACCTGCGCCGAAGACTT3'

The PCR program was as following: 30 cycles of 1 minute at 94° C., 1 minute at 62° C. and 4 minutes at 72° C., followed by 10 minutes at 72° C. A 1,8-kb fragment was produced from the positive control and the transgenic plants.

Example 9

Detection of the CABF-1, DBF-1, CBF-1, HDZ-1, ZF-1, LZ-1, and CABF-2 Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 μl of an 80° C., 1:1 mixture, of phenol to extraction buffer (100 mM LiCl, 100 mM Tris pH8, 10 mM EDTA, 1% SDS), followed by brief vortexing to mix. After the addition of 250 μl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 μl DEPC treated water. To remove contaminating DNA from the samples, each was treated with RNAse-free DNAse (Roche) according to the manufacturer's recommendations. cDNA was synthesized from total RNA using the $1^{st}$ Strand cDNA synthesis kit (Boehringer Mannheim) following manufacturer's recommendations. PCR amplification of a gene-specific fragment from the synthesized cDNA was performed using Taq DNA polymerase (Roche) and gene-specific primers (see Table 13 for primers) in the following reaction: 1×PCR buffer, 1.5 mM $MgCl_2$, 0.2 μM each primer, 0.2 μM dNTPs, 1 unit polymerase, 5 μl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

TABLE 13

Primers used for the amplification of respective transgene mRNA in PCR using RNA isolated from transgenic *Arabidopsis thaliana* plants as template

| Gene | 5' primer | 3' primer |
|------|-----------|-----------|
| DBF-1 | RC876 (SEQ ID NO:56) 5'GGAGACGGTATCACACCATC GAAGA3' | RC877 (SEQ ID NO:57) 5'TGCACAGACATCTGCCT GGCTCACA3' |
| CABF-2 | RC974 (SEQ ID NO:58) 5'GATGATCGCAGCCGAAGCTC CAGTG3' RC976: (SEQ ID NO:59) 5'GGGTGTGCCATGGACTGGTG TTCCAG3' | RC975 (SEQ ID NO:60) 5'GGCAGTCTGTGGAGGC TGATACATCA3' RC977: (SEQ ID NO:61) 5'CCTGATCCTGTGACCCC TTTTGCCA3' |
| LZ-1 | RC978 (SEQ ID NO:62) 5'GACATGGACGGTGATGCGA AGTTGG3' RC980: (SEQ ID NO:63) 5'CGGCAACAGCAGGGTCTAT ACCTTGG3' | RC979 (SEQ ID NO:64) 5'GCATACTCCAGGTCAA ATGCAGCAGC3' RC981: (SEQ ID NO:65) 5'GGGTCGGCAGCCTCCA ATCCATACA3' |
| CBF-1 | RC880 (SEQ ID NO:66) 5'GGCAGGGAATCTACGCATC GCTTTG3' | RC881 (SEQ ID NO:67) 5'CGACGAGATTCTCTGCA ACATCTGAG3' |
| HDZ-1 | RC982 (SEQ ID NO:68) 5'GGAGCTTGGACTGCGACCTC GTCAAG3' RC984: (SEQ ID NO:70) 5'GTCATCGAGGAATCGCACAA CTCCT3' | RC983 (SEQ ID NO:69) 5'GGTGTGGCTCGTGCGAG GGCTATCAG3' RC985: (SEQ ID NO:71) 5'GGTTGACGTTGGATTGC ACATGGTGG3' |
| ZF-1 | RC874 (SEQ ID NO:72) 5'TGGATGTGCGAAGTGTGCGA GGTTG3' | RC875 (SEQ ID NO:73) 5'GCGCTGCCTCTGATAAT AGAGTTGG3' |
| CABF-1 | RC938 (SEQ ID NO:74) 5'GTGCAGGAGTGCGTATCCGA GTTCATC3' | RC939 (SEQ ID NO:75) 5'CGTACGGCTGTTGCATC ATCTGCATCG3' |

Example 10

Engineering Stress-Tolerant Soybean Plants by Over-Expressing the CABF-1; DBF-1, CBF-1, HDZ-1, ZF-1, LZ-1 and CABF-2 Gene The constructs pBPSLVM111, pBPSLVM149, pBPSLVM157, pBPSLVM39, pBPSLVM12, pBPSLVM19, pBPSLVM69 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *agrobacteria*. The liquid medium is used to moisten the sterile filter paper. The embryos are incubated during 4 weeks at 25° C., under 150 µmol m$^{-2}$sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 µmol m$^{-2}$sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-Tolerant Rapeseed/Canola Plants by Over-Expressing the CABF-1; DBF-1, CBF-1, HDZ-1, ZF-1, LZ-1 and CABF-2 Gene The constructs pBPSLVM111, pBPSLVM149, pBPSLVM157, pBPSLVM39, pBPSLVM12, pBPSLVM19, pBPSLVM69 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12

Engineering Stress-Tolerant Corn Plants by Over-Expressing the CABF-1; DBF-1, CBF-1, HDZ-1, ZF-1, LZ-1 and CABF-2 Gene The constructs pBPSLVM111, pBPSLVM149, pBPSLVM157, pBPSLVM39, pBPSLVM12, pBPSLVM19, pBPSLVM69 are used to transform corn as described below.

Transformation of maize (*Zea Mays* L.) is performed with the method described by Ishida et al., 1996 Nature Biotech 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13

Engineering Stress-Tolerant Wheat Plants by Over-Expressing the CABF-1; DBF-1, CBF-1, HDZ-1, ZF-1, LZ-1 and CABF-2 Gene The constructs pBPSLVM111, pBPSLVM149, pBPSLVM157, pBPSLVM39, pBPSLVM12, pBPSLVM19, pBPSLVM69 are used to transform wheat as described below.

Transformation of wheat is performed with the method described by Ishida et al. 1996. Nature Biotech 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14

Monitoring Changes in mRNA Concentration of CABF-1, CABF-2 and CBF-1 in *Physcomitrella patens* Cultures Cold Treated DNA Microarray Slide Preparation PCR amplification was performed in 96 well plates from selected *Physcomitrella patens* ESTs cloned in the pBluescript vector. The PCR buffer set (Boehringer Mannheim) was employed for PCR reaction. Each PCR reaction mixture contains 10 µl of PCR Buffer without $MgCl_2$, 10 µl of $MgSO_4$, 3 µl of SK-Fwd primer (MWG-Biotech, Sequence: 5'-CGCCAAGCGCGCAATTAACCCTCACT-3', SEQ ID NO:76), 3 µl SK-Rev primer (MWG-Biotech, Sequence: 5'GCGTAATACGACTCACTATAGGG CGA-3', SEQ ID NO:77), 2 µl dNTP, 1 µl Taq DNA polymerase (Roche), 72 µl water and 1 µl DNA template. After denaturing at 95° C. for three minutes, the PCR reactions were performed with 35 cycles of three consecutive steps including denaturing at 95° C. for 45 seconds, annealing at 63° C. for 45 seconds, and elongation at 72° C. for 60 seconds. The last elongation was 72° C. for 10 minutes. The PCR products were then purified with QIAquick PCR purification kit (Qiagen, Inc.), eluted with water and the DNA concentration measured at 260 nm in a spectrophotometer.

2 to 5 µg of each PCR product were dried down and dissolved in 50 µl of DMSO. The PCR products were then formatted from 96 well plates to 384 well plates for printing. Microarray GenIII arrayer (Molecular Dynamics) was employed to print the PCR products to microarray slides (Molecular Dynamics) with the format recommended by the manufacturer. The printed spots were about 290 µm in diameter and were spaced about 320 µm from center to center. After printing, the slide was left in the dust free chamber for one hour to dry out. UV cross-link was performed with 600 µJ/mm. The cross-linked slides were ready for hybridization and were stored in dark and dry chambers.

Microarray Probe Synthesis

Total RNA was extracted from cold-treated *Physcomitrella patens* cultures (12 hours at 4° C. in the dark) following the RNA extraction method described in Ausubel et al. (1987 Curr. Prot. in Mol. Biol. J. Wiley and Sons, New York). Oligotex mRNA midi kit (Qiagen Inc.) was applied to isolate mRNA from total RNA with an approach combining both batch and standard protocol recommended by the manufacturer. After binding the total RNA with Oligotex, the sample was centrifuged at 14000×g to separate the Oligotex:mRNA with the liquid phase instead of running through a column. After four washes with OW2 buffer as described in batch protocol, the Oligotex:mRNA was resuspended in 400 µl OW2 and then collected by the column as the standard protocol. The mRNA was eluted following standard protocol.

Cy3 and Cy5 labeled cDNA probes were synthesized from mRNA with Superscript Choice System for cDNA synthesis (Gibco BRL). Both oligo-$(dT)_{25}$ primer (Genosys Biotechnologies) and Nonamer primer (Amersham Pharmacia Biotech) were mixed with mRNA to reach a total volume of 20 µl. The mixture was first heated at 70° C. for 10 minutes and then left at room temperature for 15 minutes before transferring to ice. Once the sample is on ice, add 8 µl First Strand Synthesis Buffer, 4 µl 0.1M DTT, 2 µl dNTP (Amersham Pharmacia Biotech), 2 µl Cy3- or Cy5-dCTP (Amersham Pharmacia Biotech), 2 µl RNAse Inhibitor (Gibco BRL) and 2 µl SuperScript II Reverse Transcriptase. The first strand synthesis was performed at 42° C. for 8 hours and the mixture was then heated at 94° C. for three minutes after the reaction.

After the first strand synthesis, 4 µl of 2.5M sodium hydroxide was added to the reaction and the mixture was incubated at 37° C. for ten minutes. 20 µl of 2M MOPS (pH 5.0) and 500 µl of PB buffer (Qiagen Inc.) were then added to each reaction. The probe was then purified by the QIAquick PCR Purification Kit (Qiagen Inc.) with the protocol provided by the manufacturer.

cDNA Microarray Hybridization and Washes

The purified Cy3- and Cy5-labeled probes were mixed and vacuum died to give a final volume of 9 µl. 9 µl Microarray Hybridization Solution (Amersham Pharmacia Biotech) and 18 µl Formamide (Sigma) were then added to the cDNA probes to give a final volume of 36 µl. The mixture was applied to the printed microarray slide that was then covered with a clean dust-free cover slide with no air trapped. The hybridization was performed in a hybridization chamber at 42° C. for 16 to 20 hours. After the hybridization, the slides were washed two times with 0.5×SSC, 0.2% SDS at room temperature for 5 minutes and 15 minutes. Two times of stringent washes were performed with 0.25×SSC, 0.1% SDS at 55° C. for 10 and 30 minutes respectively. After the washes, the slides were briefly rinsed with Millipore water and dried under compressed nitrogen.

Scanning Microarray Data Analysis

The cDNA microarrays were scanned using the microarray GenIII Scanner (Molecular Dynamics) equipped with two laser channels. The scanned images were firstly viewed and adjusted in ImageQuant software (Molecular Dynamics) and then analyzed by ArrayVision software (Molecular Dynamics). The signal intensity for each spot was extracted by ArrayVision software (Molecular Dynamics) and transferred to Excel (Microsoft). The data obtained was normalized by dividing the difference of the intensity value and background and the difference of the control value and background. The ratio was then obtained by dividing the normalized data.

Example 15

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 μg/ml denatured salmon sperm DNA
0.1% nonfat dried milk During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al., 1989, "Molecular Cloning: A Laboratory Manual", Cold Spring Harbor Laboratory Press or Ausubel, F. M. et al., 1994 "Current Protocols in Molecular Biology", John Wiley & Sons.

Example 16

Identification of Homologous Genes by Screening Expression Libraries with Antibodies cDNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al., 1989, "Molecular Cloning: A Laboratory Manual", Cold Spring Harbor Laboratory Press or Ausubel, F. M. et al., 1994 "Current Protocols in Molecular Biology", John Wiley & Sons).

Example 17

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996 DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M., 1994 Strategies 7:32-34. Transfer of mutated DNA molecules into plants is preferably done after selection and testing in microorganisms. Transgenic plants are generated according to various examples within the exemplification of this document.

Example 18

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans:

London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3$^{rd}$ ed. Academic Press: New York; Bisswanger, H., (1994) Enzymkinetik, 2$^{nd}$ ed. VCH: Weinheim (ISBN 3527300325); Bergmeyer, H. U., Bergmeyer, J., Graβ1, M., eds. (1983-1986) Methods of Enzymatic Analysis, 3$^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al., 1995 EMBO J. 14:3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 19

Purification of the Desired Product from Transformed Organisms

Recovery of the desired product from plant material (i.e., *Physcomitrella* patents or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonication. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 Appl. Environ. Microbiol. 60:133-140; Malakhova et al., 1996 Biotekhnologiya 11:27-32; and Schmidt et al., 1998 *Bioprocess Engineer.* 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

We claim:

1. A transgenic plant cell transformed with an isolated polynucleotide selected from the group consisting of:
   a) a polynucleotide having a sequence as set forth in SEQ ID NO:12; and
   b) a polynucleotide encoding a polypeptide having a sequence as set forth in SEQ ID NO:19.

2. The plant cell of claim 1, wherein the polynucleotide has the sequence as set forth in SEQ ID NO:12.

3. The plant cell of claim 1, wherein the polynucleotide encodes the polypeptide having the sequence as set forth in SEQ ID NO:19.

4. A transgenic plant transformed with an isolated polynucleotide selected from the group consisting of:
   a) a polynucleotide having a sequence as set forth in SEQ ID NO:12; and
   b) a polynucleotide encoding a polypeptide having a sequence as set forth in SEQ ID NO:19.

5. The plant of claim 4, wherein the polynucleotide has the sequence as set forth in SEQ ID NO:12.

6. The plant of claim 4, wherein polynucleotide encodes the polypeptide having the sequence as set forth in SEQ ID NO:19.

7. The plant of claim 4, wherein the plant is a monocot.

8. The plant of claim 4, wherein the plant is a dicot.

9. The plant of claim 4, wherein the plant is selected from the group consisting of maize, wheat, rye, oat, triticale, rice, barley, soybean, peanut, cotton, rapeseed, canola, manihot, pepper, sunflower, tagetes, potato, tobacco, eggplant, tomato, *Vicia* species, pea, alfalfa, coffee, cacao, tea, *Salix* species, oil palm, coconut, perennial grasses, and a forage crop plant.

10. A seed which is true breeding for a transgene comprising a polynucleotide selected from the group consisting of:
    a) a polynucleotide having a sequence as set forth in SEQ ID NO:12; and
    b) a polynucleotide encoding a polypeptide having a sequence as set forth in SEQ ID NO:19.

11. The seed of claim 10, wherein the polynucleotide has the sequence as set forth in SEQ ID NO:12.

12. The seed of claim 10, wherein the polynucleotide encodes the polypeptide having the sequence as set forth in SEQ ID NO:19.

13. An isolated nucleic acid comprising a polynucleotide selected from the group consisting of:
    a) a polynucleotide having a sequence as set forth in SEQ ID NO:12; and
    b) a polynucleotide encoding a polypeptide having a sequence as set forth in SEQ ID NO:19.

14. The isolated nucleic acid of claim 13, wherein the polynucleotide has the sequence as set forth in SEQ ID NO:12.

15. The isolated nucleic acid of claim 13, wherein the polynucleotide encodes the polypeptide having the sequence as set forth in SEQ ID NO:19.

16. A method of producing a drought-tolerant transgenic plant, the method comprising the steps of:
    a) transforming a plant cell with an expression vector comprising a polynucleotide encoding a polypeptide having a sequence as set forth in SEQ ID NO:19;
    b) growing the transformed plant cell to generate transgenic plants; and
    c) screening the transgenic plants generated in step b) to identify a transgenic plant that expresses the polypeptide and exhibits increased tolerance to drought stress as compared to a wild type variety of the plant.

17. The method of claim 16, wherein the polynucleotide has a sequence as set forth in SEQ ID NO:12.

* * * * *